United States Patent
Szabo et al.

(10) Patent No.: US 11,207,426 B2
(45) Date of Patent: Dec. 28, 2021

(54) COMPOSITIONS AND METHODS FOR SELECTIVE INHIBITION OF GRAINYHEAD-LIKE PROTEIN EXPRESSION

(71) Applicant: University of Massachusetts, Boston, MA (US)

(72) Inventors: Gyongyi Szabo, Worcester, MA (US); Guangping Gao, Westborough, MA (US); Abhishek Satishchandran, Worcester, MA (US)

(73) Assignee: University of Massachusetts, Boston, MA (US)

( * ) Notice: Subject to any disclaimer, the term of this patent is extended or adjusted under 35 U.S.C. 154(b) by 296 days.

(21) Appl. No.: 16/091,675

(22) PCT Filed: Apr. 5, 2017

(86) PCT No.: PCT/US2017/026217
§ 371 (c)(1),
(2) Date: Oct. 5, 2018

(87) PCT Pub. No.: WO2017/176929
PCT Pub. Date: Oct. 12, 2017

(65) Prior Publication Data
US 2019/0142968 A1    May 16, 2019

Related U.S. Application Data

(60) Provisional application No. 62/400,583, filed on Sep. 27, 2016, provisional application No. 62/319,169, filed on Apr. 6, 2016, provisional application No. 62/318,728, filed on Apr. 5, 2016.

(51) Int. Cl.
| | |
|---|---|
| *C12N 15/11* | (2006.01) |
| *A61K 48/00* | (2006.01) |
| *A61K 31/7105* | (2006.01) |
| *A61K 9/00* | (2006.01) |
| *C12N 15/113* | (2010.01) |
| *A61K 31/713* | (2006.01) |
| *A61K 47/68* | (2017.01) |
| *A61P 1/16* | (2006.01) |
| *C12N 5/071* | (2010.01) |

(52) U.S. Cl.
CPC ........ *A61K 48/0058* (2013.01); *A61K 9/0019* (2013.01); *A61K 31/713* (2013.01); *A61K 31/7105* (2013.01); *A61K 47/6807* (2017.08); *A61K 48/0016* (2013.01); *A61K 48/0075* (2013.01); *A61P 1/16* (2018.01); *C12N 5/067* (2013.01); *C12N 15/113* (2013.01); *C12N 2310/113* (2013.01); *C12N 2310/141* (2013.01); *C12N 2750/14143* (2013.01); *Y02A 50/30* (2018.01)

(58) Field of Classification Search
CPC .................................................... C12N 15/113
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,251,677 B1 | 6/2001 | Wilson et al. |
| 6,485,966 B2 | 11/2002 | Gao et al. |
| 6,544,786 B1 | 4/2003 | Xiao et al. |
| 6,953,690 B1 | 10/2005 | Gao et al. |
| 7,022,519 B2 | 4/2006 | Gao et al. |
| 7,198,951 B2 | 4/2007 | Gao et al. |
| 7,235,393 B2 | 6/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,249,424 B2 | 2/2016 | Wolf et al. |
| 9,701,984 B2 | 7/2017 | Gao et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |
| 2003/0110526 A1 | 6/2003 | Brown et al. |

(Continued)

FOREIGN PATENT DOCUMENTS

| | | |
|---|---|---|
| EP | 2261242 A1 | 12/2010 |
| EP | 2468891 A2 | 6/2012 |

(Continued)

OTHER PUBLICATIONS

Satishchandran et al, Therapeutic overexpression of miR-122 protects mice from chronic alcoholic liver injury through regulation of hypoxia-inducible factor-1α, Hepatology, Oct. 2015, vol. 62, Suppl. 1, Abstract 496, p. 458A-459A). (Year: 2015).*

(Continued)

*Primary Examiner* — Ekaterina Poliakova-Georgantas
*Assistant Examiner* — Ekaterina Poliakova
(74) *Attorney, Agent, or Firm* — Wolf, Greenfield & Sacks, P.C.

(57) ABSTRACT

In some aspects, the disclosure relates to methods and compositions for modulation of miR-122 expression in a cell or a subject. In some embodiments, methods and compositions described by the disclosure are useful for the treatment of liver-associated diseases (e.g., chronic liver disease, alcoholic liver disease).

10 Claims, 44 Drawing Sheets
Specification includes a Sequence Listing.

(56) References Cited

U.S. PATENT DOCUMENTS

| | | |
|---|---|---|
| 2003/0138772 A1 | 7/2003 | Gao et al. |
| 2004/0101514 A1 | 5/2004 | Liu et al. |
| 2005/0014262 A1 | 1/2005 | Gao et al. |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0215879 A1 | 8/2009 | DiPrimio et al. |
| 2010/0186103 A1 | 7/2010 | Gao et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0053429 A1* | 2/2013 | Schrum ............... A61K 31/713 514/44 A |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2015/0065560 A1 | 3/2015 | Bjorklund et al. |
| 2015/0258180 A1 | 9/2015 | Mahuran et al. |
| 2015/0299702 A1* | 10/2015 | Kjems ............... A61K 31/7088 514/44 A |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0114340 A1 | 4/2017 | Mueller et al. |
| 2017/0165377 A1 | 6/2017 | Gao et al. |

FOREIGN PATENT DOCUMENTS

| | | |
|---|---|---|
| WO | WO 2003/042397 | 5/2003 |
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2008/125846 A2 | 10/2008 |
| WO | WO 2009/043936 | 4/2009 |
| WO | WO 2009/109665 A1 | 9/2009 |
| WO | WO 2009/146178 A1 | 12/2009 |
| WO | WO 2010/027446 A2 | 3/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 11/2014 |
| WO | WO 2015/121501 A1 | 8/2015 |
| WO | WO 2015/164786 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Tanaka et al, Gain of GRHL2 is associated with early recurrence of hepatocellular carcinoma, Journal of Hepatology, 2008, 49: 746-757 (Year: 2008).*

Adachi et al., Drawing a high-resolution functional map of adeno-associated virus capsid by massively parallel sequencing. Nat Commun. 2014;5:3075. doi: 10.1038/ncomms4075.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Borel et al., Recombinant AAV as a platform for translating the therapeutic potential of RNA interference. Mol Ther. Apr. 2014;22(4):692-701. doi:10.1038/mt.2013.285. Epub Dec. 19, 2013.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Buning et al., Receptor targeting of adeno-associated virus vectors. Gene Ther. Jul. 2003;10(14):1142-51.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses". ed., P. Tijsser, CRC Press. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.

Chadderton et al., Improved retinal function in a mouse model of dominant retinitis pigmentosa following AAV-delivered gene therapy. Mol Ther. Apr. 2009;17(4):593-9. Epub Jan. 27, 2009.

(56) References Cited

OTHER PUBLICATIONS

Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.

Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.

Cheng et al., Development of optimized AAV3 serotype vectors: mechanism of high-efficiency transduction of human liver cancer cells. Gene Ther. Apr. 2012;19(4):375-84. doi: 10.1038/gt.2011. 105. Epub Jul. 21, 2011.

Chiorini et al., Cloning and characterization of adeno-associated virus type 5. J Virol. Feb. 1999;73(2):1309-19.

Choudhury et al., Identification of Novel vectors capable of CNS transduction in adult mice after single round selection using DNA shuffled AAV capsid library. Mol Ther. May 1, 2013;21(1):S1/.

Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.

Conlon et al., Ribozyme Approaches towards Down-Regulation of Pi*Z Mutant Human a-1 Anti-Trypsin. Mol. Therapy. 2004;9:S333. Abstract 875.

Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.

Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.

Cruz et al., The promise of gene therapy for the treatment of alpha-1 antitrypsin deficiency. Pharmacogenomics. Sep. 2007;8(9):1191-8.

Csak et al., microRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.

Davidoff et al., Sex significantly influences transduction of murine liver by recombinant adeno-associated viral vectors through an androgen-dependent pathway. Blood. Jul. 15, 2003; 102(2):480-8. Epub Mar. 13, 2003.

Daya et al., Gene therapy using adeno-associated virus vectors. Clin Microbiol Rev. Oct. 2008;21(4):583-93. doi: 10.1128/CMR.00008-08.

Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

Fisher et al., Transduction with recombinant adeno-associated virus for gene therapy is limited by leading-strand synthesis. J Virol. Jan. 1996;70(1):520-32.

Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.

Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

Foust et al., Intravascular AAV9 preferentially targets neonatal-neurons and adult-astrocytes. Nature Biotechnology, 27; 59-65 2009.

Foust et al., Over the barrier and through the blood: to CNS delivery we go. Cell Cycle. Dec. 15, 2009;8(24):4017-8.

Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

Gao et al., Biology of AAV serotype vectors in liver-directed gene transfer to nonhuman primates. Mol Ther. Jan. 2006;13(1):77-87. Epub Oct. 10, 2005.

Gao et al., Inadvertent gene transfer of co-packaged rep and cap sequences during the production of AAV vector and its potential impact on vector performance. Molecular Therapy. May 2008; 16(Suppl. 1):S105-S106. Abstract 279.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., RAAV-mediated targeting in adult mice and its potential in generating animal models of tissue-specific somatic transgenics or knock down. Molecular Therapy. May 2008;16(1):S118-S119. Abstract 316.

GENBANK Submission; NCBI, Accession No. AAS99264; Gao et al.; Jun. 24, 2004.

GENBANK Submission; NCBI, Accession No. AY530579.10; 2004.

Girard et al., miR-122, a paradigm for the role of microRNAs in the liver. J Hepatol. Apr. 2008;48(4):648-56. doi: 10.1016/j.jhep.2008.01.019. Epub Feb. 12, 2008.

Gramantieri et al., Cyclin G1 is a target of miR-122a, a microRNA frequently down-regulated in human hepatocellular carcinoma. Cancer Res. Jul. 1, 2007;67(13):6092-9.

Grimm et al., Fatality in mice due to oversaturation of cellular microRNA/short hairpin RNA pathways. Nature. May 25, 2006;441(7092):537-41.

Grimm, Small silencing RNAs: state-of-the-art. Adv Drug Deliv Rev. Jul. 25, 2009;61(9):672-703. doi: 10.1016/j.addr.2009.05.002. Epub May 7, 2009.

Haussecker et al., miR-122 continues to blaze the trail for microRNA therapeutics. Mol Ther. Feb. 2010;18(2):240-2. doi: 10.1038/mt.2009.313.

Hsu et al., Essential metabolic, anti-inflammatory, and anti-tumorigenic functions of miR-122 in liver. J Clin Invest. Aug. 2012;122(8):2871-83. doi:10.1172/JCI63539. Epub Jul. 23, 2012.

Iida et al., Systemic Delivery of Tyrosine-Mutant AAV Vectors Results in Robust Transduction of Neurons in Adult Mice. BioMed Res Int. 2013;2013.

Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.

Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.

Kota et al., Therapeutic microRNA delivery suppresses tumorigenesis in a murine liver cancer model. Cell. Jun. 12, 2009;137(6):1005-17. doi: 10.1016/j.cell.2009.04.021.

Kotin et al., Organization of adeno-associated virus DNA in latently infected Detroit 6 cells. Virology. Jun. 1989; 170(2):460-7.

Kotin et al., Site-specific integration by adeno-associated virus. Proc Natl Acad Sci U S A. Mar. 1990;87(6):2211-5.

Lanford et al., Therapeutic silencing of microRNA-122 in primates with chronic hepatitis C virus infection. Science. Jan. 8, 2010;327(5962):198-201. Epub Dec. 3, 2009.

Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.

Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].

(56) References Cited

OTHER PUBLICATIONS

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Ex vivo transduction and transplantation of bone marrow cells for liver gene delivery of alpha1-antitrypsin. Mol Ther. Aug. 2010;18(8):1553-8. Epub Jun. 15, 2010.
Li et al., Protein trans-splicing as a means for viral vector-mediated in vivo gene therapy. Hum Gene Ther. Sep. 2008;19(9):958-64. doi: 10.1089/hum.2008.009.
Lowenstein, Crossing the rubicon. Nat Biotechnol. Jan. 2009;27(1):42-4.
Lux et al., Green fluorescent protein-tagged adeno-associated virus particles allow the study of cytosolic and nuclear trafficking. J Virol. Sep. 2005;79(18):11776-87.
Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.
Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Malinkevich et al., 1002. rAAV Mediated Delivery of Target Specific Micro RNA Sponges for Study of Micro RNA Function in Mouse Models. Gene regulation. May 1, 2009;17(1):S382.
Manfredsson et al., AAV9: a potential blood-brain barrier buster. Mol Ther. Mar. 2009;17(3):403-5.
Matalon et al., Adeno-associated virus-mediated aspartoacylase gene transfer to the brain of knockout mouse for canavan disease. Mol Ther. May 2003;7(5 Pt 1):580-7.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
McLean et al., Gene targeted therapeutics for liver disease in alpha-1 antitrypsin deficiency. Biologies. 2009;3:63-75. Epub Jul. 13, 2009.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
Mueller et al., Development of Simultaneous Gene Augmentation and Reduction of Mutant Gene Expression with a Single Recombinant AAV for Alpha-1 Antitrypsin Disease. Molecular Therapy May 2009;17(l):S391-S392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., Using rAAV Delivered miRNAs To Knockdown Misfolded Human Alpha 1 Antitrypsin in a Transgenic Mouse Model. Molecular Therapy May 2010;18(1):S21. Abstract 51.
NCBI Blast Protein Sequence. RID-09JSKF33114. Alignment of Seq ID Nos. 87, 179. 2016.

O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pfeifer et al., Pharmacological potential of RNAi—focus on miRNA. Pharmacol Ther. Jun. 2010;126(3):217-27. doi: 10.1016/j.pharmthera.2010.03.006. Epub Apr. 11, 2010.
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Stoica et al., Targeting Human SOD1 Using AAV mediated RNAi in a mouse model of amyotrophic lateral sclerosis. Mol ther. Jun. 2013;21(1):S149.
Tanimizu et al., Downregulation of miR122 by grainyhead-like 2 restricts the hepatocytic differentiation potential of adult liver progenitor cells. Development. Dec. 2014;141(23):4448-56. doi:10.1242/dev.113654. Epub Nov. 18, 2014.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

(56) References Cited

OTHER PUBLICATIONS

Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knock-down of cognate micro RNAs, upregulation of their natural target genes and phenotypic changes in mice. Molecular Therapy. May 2010; 18(1): S140. Abstract 362.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

Xu et al., Delivery of MDR1 small interfering RNA by self-complementary recombinant adeno-associated virus vector. Mol Ther. Apr. 2005;11(4):523-30.

Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

Extended European Search Report for Application No. EP 17779777.6, dated Oct. 24, 2019.

Ambade et al., Alcoholic hepatitis accelerates early hepatobiliary cancer by increasing sternness and miR-122-mediated HIF-1a activation. Scientific Reports. 2016;6(21340). doi: 10.1038/scirep21340. 15 pages.

Satishchandran et al., 655 Grainyhead-Like 2, a Novel Hepatic Transcription Factor, Promotes Alcohol-induced Liver Injury, Steatosis and Inflammation via miR-122 Down-regulation. Gastroenterology. Apr. 2016;150(4):S1044. doi: 10.1016/S0016-5085(16)33527-2.

Satishchandran et al., MicroRNA 122, Regulated by GRTH2, Protects Livers of Mice and Patients From Ethanol-Induced Liver Disease. Gastroenterology. Jan. 2018;154(1):238-252.e7. doi: 10.1053/j.gastro.2017.09.022. Epub Oct. 4, 2017.

Xie et al., AAV-mediated miRNA Delivery and Therapeutics. Semin Liver Dis. Feb. 2015; 35(1): 81-88. EPub Jan. 29, 2015. doi: 10.1055/s-0034-1397352.

Xie et al., Long-term, efficient inhibition of microRNA function in mice using rAAV vectors. Nat Methods. Mar. 4, 2012;9(4):403-9. doi: 10.1038/nmeth.1903.

PCT/US2017/026217, dated Jul. 5, 2017, International Search Report and Written Opinion.

PCT/US2017/026217, dated Oct. 18, 2018, International Preliminary Report on Patentability.

\* cited by examiner

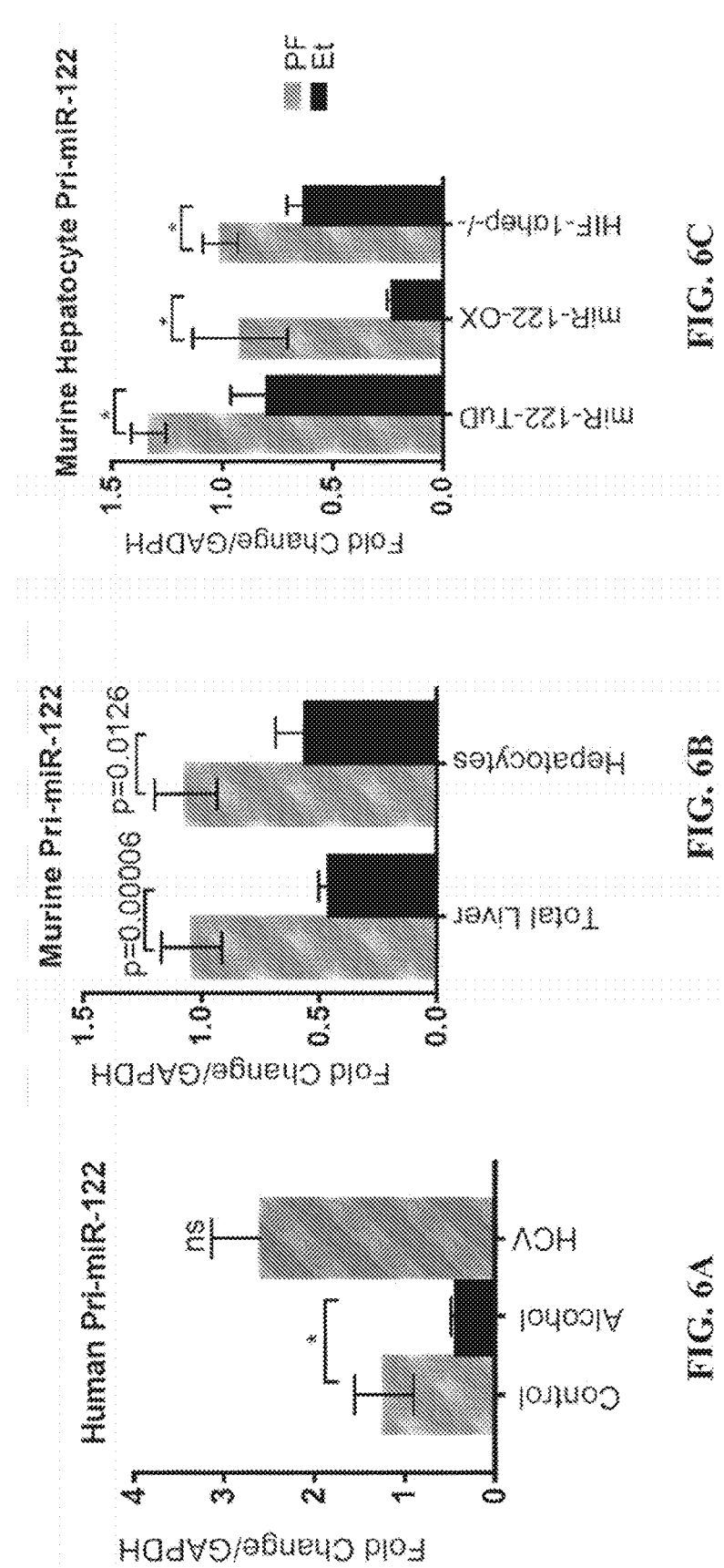

Histology scoring and cytokines in WT and HIFKO mice

SEQUENCE LISTING

<160> NUMBER OF SEQ ID NOS: 33

<210> SEQ ID NO 1
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 1
gcgggatccg actgcagttt cagcgtttgg          30

<210> SEQ ID NO 2
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 2
cgcggatcca aaaagactc tagggcccga ctttaca          37

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
caccaccatc aaggactcaa          20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
caggtccctg tcatgcttct          20

<210> SEQ ID NO 5
<211> LENGTH: 21
<212> TYPE: DNA
<213> ORGANISM: Artificial Sequence
<220> FEATURE:

<223> OTHER INFORMATION: Synthetic polynucleotide

<400> SEQUENCE: 5
gtcccagaca tcagggagta a                                    21

<210> SEQ ID NO 6
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 6
attcctggcg ttaccttg                                        18

<210> SEQ ID NO 7
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 7
gctcctctta ggggccat                                        18

<210> SEQ ID NO 8
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 8
caagatctcg gcgaagcaa                                       19

<210> SEQ ID NO 9
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 9
agctcgaggc tccgtagtgt tt                                   22

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
tgcatctagc aatggacagc                                      20

<210> SEQ ID NO 11
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 11
cccacagggc agcacagtgg ac                                   22

```
<210> SEQ ID NO 12
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 12
ctttgaagtt gacggaccc                                              19

<210> SEQ ID NO 13
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 13
ttccagcgca tgtcggcgct c                                           21

<210> SEQ ID NO 14
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 14
ggaagaccac tcgcattcct t                                           21

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
gtaacccgtt gaaccccatt                                             20

<210> SEQ ID NO 16
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 16
gaaagtccag tttcaccaga gg                                          22

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
aggcaacctg accactctcc                                             20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide
```

<400> SEQUENCE: 18
caggtccctg tcatgcttct                                              20

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 19
tcggatactt cagcgtcagg a                                            21

<210> SEQ ID NO 20
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 20
ctgtattccg tctccttggt t                                            21

<210> SEQ ID NO 21
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 21
ccacgtctca ccattggg                                                18

<210> SEQ ID NO 22
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 22
ggtgagcctc ataacagaag cttt                                         24

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 23
gaaaatgtgc aggtgttgac ca                                           22

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24
gccttctgga tccatttgaa                                              20

<210> SEQ ID NO 25
<211> LENGTH: 22

<210> SEQ ID NO 25
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 25
tccacagcag aagctttggc cc                                          22

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
tgagtgatac tgcctgcctg                                             20

<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 27
ggtactagtc cgtggttctt c                                           21

<210> SEQ ID NO 28
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 28
tcgcactttg gtattcttgg ag                                          22

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
ccatccaatc ggtagtagcg                                             20

<210> SEQ ID NO 30
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 30
ggcactaagg ccactagtct ttt                                         23

<210> SEQ ID NO 31
<211> LENGTH: 618
<212> TYPE: PRT
<213> ORGANISM: Homo sapiens

<400> SEQUENCE: 31

Met Thr Gln Glu Tyr Asp Asn Lys Arg Pro Val Leu Val Leu Gln Asn
1               5                   10                  15

```
Glu Ala Leu Tyr Pro Gln Arg Arg Ser Tyr Thr Ser Glu Asp Glu Ala
             20                  25                  30

Trp Lys Ser Phe Leu Glu Asn Pro Leu Thr Ala Ala Thr Lys Ala Met
         35                  40                  45

Met Ser Ile Asn Gly Asp Glu Asp Ser Ala Ala Ala Leu Gly Leu Leu
     50                  55                  60

Tyr Asp Tyr Tyr Lys Val Pro Arg Glu Arg Ser Ser Thr Ala Lys
 65                  70                  75                  80

Pro Glu Val Glu His Pro Glu Pro Asp His Ser Lys Arg Asn Ser Ile
                 85                  90                  95

Pro Ile Val Thr Glu Gln Pro Leu Ile Ser Ala Gly Glu Asn Arg Val
             100                 105                 110

Gln Val Leu Lys Asn Val Pro Phe Asn Ile Val Leu Pro His Gly Asn
         115                 120                 125

Gln Leu Gly Ile Asp Lys Arg Gly His Leu Thr Ala Pro Asp Thr Thr
     130                 135                 140

Val Thr Val Ser Ile Ala Thr Met Pro Thr His Ser Ile Lys Thr Glu
145                 150                 155                 160

Thr Gln Pro His Gly Phe Ala Val Gly Ile Pro Pro Ala Val Tyr His
                 165                 170                 175

Pro Glu Pro Thr Glu Arg Val Val Phe Asp Arg Asn Leu Asn Thr
             180                 185                 190

Asp Gln Phe Ser Ser Gly Ala Gln Ala Pro Asn Ala Gln Arg Arg Thr
         195                 200                 205

Pro Asp Ser Thr Phe Ser Glu Thr Phe Lys Glu Gly Val Gln Glu Val
     210                 215                 220

Phe Phe Pro Ser Asp Leu Ser Leu Arg Met Pro Gly Met Asn Ser Glu
225                 230                 235                 240

Asp Tyr Val Phe Asp Ser Val Ser Gly Asn Asn Phe Glu Tyr Thr Leu
                 245                 250                 255

Glu Ala Ser Lys Ser Leu Arg Gln Lys Pro Gly Asp Ser Thr Met Thr
         260                 265                 270

Tyr Leu Asn Lys Gly Gln Phe Tyr Pro Ile Thr Leu Lys Glu Val Ser
     275                 280                 285

Ser Ser Glu Gly Ile His His Pro Ile Ser Lys Val Arg Ser Val Ile
290                 295                 300

Met Val Val Phe Ala Glu Asp Lys Ser Arg Glu Asp Gln Leu Arg His
305                 310                 315                 320

Trp Lys Tyr Trp His Ser Arg Gln His Thr Ala Lys Gln Arg Cys Ile
                 325                 330                 335

Asp Ile Ala Asp Tyr Lys Glu Ser Phe Asn Thr Ile Ser Asn Ile Glu
         340                 345                 350

Glu Ile Ala Tyr Asn Ala Ile Ser Phe Thr Trp Asp Ile Asn Asp Glu
     355                 360                 365

Ala Lys Val Phe Ile Ser Val Asn Cys Leu Ser Thr Asp Phe Ser Ser
         370                 375                 380

Gln Lys Gly Val Lys Gly Leu Pro Leu Asn Ile Gln Val Asp Thr Tyr
385                 390                 395                 400

Ser Tyr Asn Asn Arg Ser Asn Lys Pro Val His Arg Ala Tyr Cys Gln
                 405                 410                 415

Ile Lys Val Phe Cys Asp Lys Gly Ala Glu Arg Lys Ile Arg Asp Glu
             420                 425                 430
```

```
Glu Arg Lys Gln Ser Lys Arg Val Ser Asp Val Lys Val Pro Leu
        435                 440                 445

Leu Pro Ser His Lys Arg Met Asp Ile Thr Val Phe Lys Pro Phe Ile
450                 455                 460

Asp Leu Asp Thr Gln Pro Val Leu Phe Ile Pro Asp Val His Phe Ala
465                 470                 475                 480

Asn Leu Gln Arg Gly Thr His Val Leu Pro Ile Ala Ser Glu Glu Leu
                485                 490                 495

Glu Gly Glu Gly Ser Val Leu Lys Arg Gly Pro Tyr Gly Thr Glu Asp
            500                 505                 510

Asp Phe Ala Val Pro Pro Ser Thr Lys Leu Ala Arg Ile Glu Glu Pro
        515                 520                 525

Lys Arg Val Leu Leu Tyr Val Arg Lys Glu Ser Glu Glu Val Phe Asp
530                 535                 540

Ala Leu Met Leu Lys Thr Pro Ser Leu Lys Gly Leu Met Glu Ala Ile
545                 550                 555                 560

Ser Asp Lys Tyr Asp Val Pro His Asp Lys Ile Gly Lys Ile Phe Lys
                565                 570                 575

Lys Cys Lys Lys Gly Ile Leu Val Asn Met Asp Asp Asn Ile Val Lys
            580                 585                 590

His Tyr Ser Asn Glu Asp Thr Phe Gln Leu Gln Ile Glu Glu Ala Gly
        595                 600                 605

Gly Ser Tyr Lys Leu Thr Leu Thr Glu Ile
    610                 615

<210> SEQ ID NO 32
<211> LENGTH: 625
<212> TYPE: PRT
<213> ORGANISM: Homo sapiens

<400> SEQUENCE: 32

Met Ser Gln Glu Ser Asp Asn Asn Lys Arg Leu Val Ala Leu Val Pro
1               5                   10                  15

Met Pro Ser Asp Pro Pro Phe Asn Thr Arg Arg Ala Tyr Thr Ser Glu
            20                  25                  30

Asp Glu Ala Trp Lys Ser Tyr Leu Glu Asn Pro Leu Thr Ala Ala Thr
        35                  40                  45

Lys Ala Met Met Ser Ile Asn Gly Asp Glu Asp Ser Ala Ala Ala Leu
    50                  55                  60

Gly Leu Leu Tyr Asp Tyr Tyr Lys Val Pro Arg Asp Lys Arg Leu Leu
65                  70                  75                  80

Ser Val Ser Lys Ala Ser Asp Ser Gln Glu Asp Gln Glu Lys Arg Asn
                85                  90                  95

Cys Leu Gly Thr Ser Glu Ala Gln Ser Asn Leu Ser Gly Gly Glu Asn
            100                 105                 110

Arg Val Gln Val Leu Lys Thr Val Pro Val Asn Leu Ser Leu Asn Gln
        115                 120                 125

Asp His Leu Glu Asn Ser Lys Arg Glu Gln Tyr Ser Ile Ser Phe Pro
    130                 135                 140

Glu Ser Ser Ala Ile Ile Pro Val Ser Gly Ile Thr Val Val Lys Ala
145                 150                 155                 160

Glu Asp Phe Thr Pro Val Phe Met Ala Pro Pro Val His Tyr Pro Arg
                165                 170                 175

Gly Asp Gly Glu Glu Gln Arg Val Val Ile Phe Glu Gln Thr Gln Tyr
            180                 185                 190
```

```
Asp Val Pro Ser Leu Ala Thr His Ser Ala Tyr Leu Lys Asp Gln
        195                 200                 205

Arg Ser Thr Pro Asp Ser Thr Tyr Ser Glu Ser Phe Lys Asp Ala Ala
    210                 215                 220

Thr Glu Lys Phe Arg Ser Ala Ser Val Gly Ala Glu Glu Tyr Met Tyr
225                 230                 235                 240

Asp Gln Thr Ser Ser Gly Thr Phe Gln Tyr Thr Leu Glu Ala Thr Lys
                245                 250                 255

Ser Leu Arg Gln Lys Gln Gly Glu Gly Pro Met Thr Tyr Leu Asn Lys
            260                 265                 270

Gly Gln Phe Tyr Ala Ile Thr Leu Ser Glu Thr Gly Asp Asn Lys Cys
        275                 280                 285

Phe Arg His Pro Ile Ser Lys Val Arg Ser Val Val Met Val Val Phe
    290                 295                 300

Ser Glu Asp Lys Asn Arg Asp Glu Gln Leu Lys Tyr Trp Lys Tyr Trp
305                 310                 315                 320

His Ser Arg Gln His Thr Ala Lys Gln Arg Val Leu Asp Ile Ala Asp
                325                 330                 335

Tyr Lys Glu Ser Phe Asn Thr Ile Gly Asn Ile Glu Glu Ile Ala Tyr
            340                 345                 350

Asn Ala Val Ser Phe Thr Trp Asp Val Asn Glu Glu Ala Lys Ile Phe
        355                 360                 365

Ile Thr Val Asn Cys Leu Ser Thr Asp Phe Ser Ser Gln Lys Gly Val
    370                 375                 380

Lys Gly Leu Pro Leu Met Ile Gln Ile Asp Thr Tyr Ser Tyr Asn Asn
385                 390                 395                 400

Arg Ser Asn Lys Pro Ile His Arg Ala Tyr Cys Gln Ile Lys Val Phe
                405                 410                 415

Cys Asp Lys Gly Ala Glu Arg Lys Ile Arg Asp Glu Arg Lys Gln
            420                 425                 430

Asn Arg Lys Lys Gly Lys Gly Gln Ala Ser Gln Thr Gln Cys Asn Ser
        435                 440                 445

Ser Ser Asp Gly Lys Leu Ala Ala Ile Pro Leu Gln Lys Lys Ser Asp
    450                 455                 460

Ile Thr Tyr Phe Lys Thr Met Pro Asp Leu His Ser Gln Pro Val Leu
465                 470                 475                 480

Phe Ile Pro Asp Val His Phe Ala Asn Leu Gln Arg Thr Gly Gln Val
                485                 490                 495

Tyr Tyr Asn Thr Asp Asp Glu Arg Glu Gly Ser Val Leu Val Lys
            500                 505                 510

Arg Met Phe Arg Pro Met Glu Glu Phe Gly Pro Val Pro Ser Lys
        515                 520                 525

Gln Met Lys Glu Glu Gly Thr Lys Arg Val Leu Leu Tyr Val Arg Lys
    530                 535                 540

Glu Thr Asp Asp Val Phe Asp Ala Leu Met Leu Lys Ser Pro Thr Val
545                 550                 555                 560

Lys Gly Leu Met Glu Ala Ile Ser Glu Lys Tyr Gly Leu Pro Val Glu
                565                 570                 575

Lys Ile Ala Lys Leu Tyr Lys Lys Ser Lys Lys Gly Ile Leu Val Asn
            580                 585                 590

Met Asp Asp Asn Ile Ile Glu His Tyr Ser Asn Glu Asp Thr Phe Ile
        595                 600                 605
```

```
Leu Asn Met Glu Ser Met Val Glu Gly Phe Lys Val Thr Leu Met Glu
    610                 615                 620

Ile
625

<210> SEQ ID NO 33
<211> LENGTH: 607
<212> TYPE: PRT
<213> ORGANISM: Homo sapiens

<400> SEQUENCE: 33

Met Trp Met Asn Ser Ile Leu Pro Ile Phe Leu Phe Arg Ser Val Arg
1               5                   10                  15

Leu Leu Lys Asn Asp Pro Val Asn Leu Gln Lys Phe Ser Tyr Thr Ser
            20                  25                  30

Glu Asp Glu Ala Trp Lys Thr Tyr Leu Glu Asn Pro Leu Thr Ala Ala
        35                  40                  45

Thr Lys Ala Met Met Arg Val Asn Gly Asp Asp Ser Val Ala Ala
    50                  55                  60

Leu Ser Phe Leu Tyr Asp Tyr Met Gly Pro Lys Glu Lys Arg Ile
65              70                  75                  80

Leu Ser Ser Ser Thr Gly Gly Arg Asn Asp Gln Gly Lys Arg Tyr Tyr
                85                  90                  95

His Gly Met Glu Tyr Glu Thr Asp Leu Thr Pro Leu Ser Pro Thr
            100                 105                 110

His Leu Met Lys Phe Leu Thr Glu Asn Val Ser Gly Thr Pro Glu Tyr
            115                 120                 125

Pro Asp Leu Leu Lys Lys Asn Asn Leu Met Ser Leu Glu Gly Ala Leu
130                 135                 140

Pro Thr Pro Gly Lys Ala Ala Pro Leu Pro Ala Gly Pro Ser Lys Leu
145                 150                 155                 160

Glu Ala Gly Ser Val Asp Ser Tyr Leu Leu Pro Thr Thr Asp Met Tyr
                165                 170                 175

Asp Asn Gly Ser Leu Asn Ser Leu Phe Glu Ser Ile His Gly Val Pro
            180                 185                 190

Pro Thr Gln Arg Trp Gln Pro Asp Ser Thr Phe Lys Asp Asp Pro Gln
        195                 200                 205

Glu Ser Met Leu Phe Pro Asp Ile Leu Lys Thr Ser Pro Glu Pro Pro
    210                 215                 220

Cys Pro Glu Asp Tyr Pro Ser Leu Lys Ser Asp Phe Glu Tyr Thr Leu
225                 230                 235                 240

Gly Ser Pro Lys Ala Ile His Ile Lys Ser Gly Glu Ser Pro Met Ala
                245                 250                 255

Tyr Leu Asn Lys Gly Gln Phe Tyr Pro Val Thr Leu Arg Thr Pro Ala
            260                 265                 270

Gly Gly Lys Gly Leu Ala Leu Ser Ser Asn Lys Val Lys Ser Val Val
        275                 280                 285

Met Val Val Phe Asp Asn Glu Lys Val Pro Val Glu Gln Leu Arg Phe
    290                 295                 300

Trp Lys His Trp His Ser Arg Gln Pro Thr Ala Lys Gln Arg Val Ile
305                 310                 315                 320

Asp Val Ala Asp Cys Lys Glu Asn Phe Asn Thr Val Glu His Ile Glu
                325                 330                 335

Glu Val Ala Tyr Asn Ala Leu Ser Phe Val Trp Asn Val Asn Glu Glu
            340                 345                 350
```

-continued

```
Ala Lys Val Phe Ile Gly Val Asn Cys Leu Ser Thr Asp Phe Ser Ser
            355                 360                 365

Gln Lys Gly Val Lys Gly Val Pro Leu Asn Leu Gln Ile Asp Thr Tyr
            370                 375                 380

Asp Cys Gly Leu Gly Thr Glu Arg Leu Val His Arg Ala Val Cys Gln
385                 390                 395                 400

Ile Lys Ile Phe Cys Asp Lys Gly Ala Glu Arg Lys Met Arg Asp Asp
                405                 410                 415

Glu Arg Lys Gln Phe Arg Arg Lys Val Lys Cys Pro Asp Ser Ser Asn
            420                 425                 430

Ser Gly Val Lys Gly Cys Leu Leu Ser Gly Phe Arg Gly Asn Glu Thr
            435                 440                 445

Thr Tyr Leu Arg Pro Glu Thr Asp Leu Glu Thr Pro Pro Val Leu Phe
            450                 455                 460

Ile Pro Asn Val His Phe Ser Ser Leu Gln Arg Ser Gly Gly Ala Ala
465                 470                 475                 480

Pro Ser Ala Gly Pro Ser Ser Ser Asn Arg Leu Pro Leu Lys Arg Thr
                485                 490                 495

Cys Ser Pro Phe Thr Glu Glu Phe Glu Pro Leu Pro Ser Lys Gln Ala
                500                 505                 510

Lys Glu Gly Asp Leu Gln Arg Val Leu Leu Tyr Val Arg Arg Glu Thr
            515                 520                 525

Glu Glu Val Phe Asp Ala Leu Met Leu Lys Thr Pro Asp Leu Lys Gly
            530                 535                 540

Leu Arg Asn Ala Ile Ser Glu Lys Tyr Gly Phe Pro Glu Glu Asn Ile
545                 550                 555                 560

Tyr Lys Val Tyr Lys Lys Cys Lys Arg Gly Ile Leu Val Asn Met Asp
                565                 570                 575

Asn Asn Ile Ile Gln His Tyr Ser Asn His Val Ala Phe Leu Leu Asp
                580                 585                 590

Met Gly Glu Leu Asp Gly Lys Ile Gln Ile Ile Leu Lys Glu Leu
            595                 600                 605
```

US 11,207,426 B2

COMPOSITIONS AND METHODS FOR SELECTIVE INHIBITION OF GRAINYHEAD-LIKE PROTEIN EXPRESSION

RELATED APPLICATIONS

This application is a national stage filing under 35 U.S.C. § 371 of International Application No. PCT/US2017/026217, filed Apr. 5, 2017, and claims the benefit of the filing date of U.S. Provisional Application No. 62/318,728, entitled "COMPOSITIONS AND METHODS FOR SELECTIVE INHIBITION OF GRAINYHEAD-LIKE 2 PROTEIN EXPRESSION," filed Apr. 5, 2016; U.S. Provisional Application No. 62/319,169, entitled "COMPOSITIONS AND METHODS FOR SELECTIVE INHIBITION OF GRAINYHEAD-LIKE 2 PROTEIN EXPRESSION," filed Apr. 6, 2016; and U.S. Provisional Application No. 62/400,583, entitled "COMPOSITIONS AND METHODS FOR SELECTIVE INHIBITION OF GRAINYHEAD-LIKE 2 PROTEIN EXPRESSION," filed Sep. 27, 2016, the contents of each which are incorporated herein by reference in their entireties.

FEDERALLY SPONSORED RESEARCH

This invention was made with government support under grant numbers AA020744 and AA022283, awarded by the National Institutes of Health. The government has certain rights in the invention.

BACKGROUND OF INVENTION

Chronic, excessive alcohol consumption accounts for nearly 50% of all chronic liver disease deaths in the western world. Generally, chronic liver disease involves a process of progressive destruction and regeneration of the liver parenchyma leading to fibrosis and cirrhosis. Examples of chronic liver disease include inflammation (chronic hepatitis), liver cirrhosis, and hepatocellular carcinoma. Treatment of chronic liver disease may involve complex and expensive treatment regimens and, in certain cases, requires liver transplantation. Improved methods and compositions for treatment of liver diseases are needed.

SUMMARY OF INVENTION

In some aspects, the disclosure relates to methods and compositions for the treatment of liver-associated diseases (e.g., chronic liver disease, alcoholic liver disease, etc.). The disclosure is based, in part, on the discovery that certain forms of grainyhead-like transcriptional regulators (GRHL) (e.g., spliced form of GRHL2) modulate (e.g., inhibit) expression of miR-122 in liver cells. In some embodiments, miR-122 expression is reduced in cells, or subjects, having (e.g., characterized by) chronic liver disease. Accordingly, in some aspects, the disclosure provides a method for modulating miR-122 expression in a cell, the method comprising: contacting a cell with an effective amount of a grainyhead-like transcriptional regulator (GRHL) modulating agent. In some embodiments, the GRHL modulating agent is an inhibitory nucleic acid that inhibits expression of a grainyhead-like transcriptional regulator (GRHL). In some embodiments, inhibition of a GRHL results in an increase in expression of miR-122 in the cell.

The disclosure relates, in part, to the discovery that grainyhead-like transcriptional regulator (GRHL) (e.g., the spliced form of GRHL2) modulates (e.g., inhibits) expression of miR-122, which modulates expression of hypoxia-inducible factor 1α (HIF1α). For example, in some embodiments, expression of grainyhead-like regulator (e.g., spliced form of GRHL2) inhibits expression of miR-122 and results in increased expression of HIF-1α. Thus, in some aspects, the disclosure provides a method for inhibiting hypoxia-inducible factor 1α (HIF-1α) expression in a cell (e.g., a liver cell of a subject having a liver-associated disease), the method comprising: increasing expression of miR-122 in the cell. In some embodiments, expression of miR-122 is increased in the cell by delivering to the cell a nucleic acid engineered to express miR-122. In some embodiments, inhibition of a GRHL, or expression of miR-122, results in a decrease in expression of HIF-1α in the cell.

In some aspects, the disclosure relates to methods and compositions for treatment of liver-associated diseases (e.g., chronic liver disease). In some embodiments, the liver-associated disease is alcoholic liver disease (ALD), cirrhosis, hepatitis A, hepatitis B, hepatitis C, hepatocellular carcinoma (HCC), or fibrosis of the liver. In some embodiments, the liver-associated disease results in hepatic lipid accumulation in the subject. Accordingly, in some aspects, the disclosure provides a method for treating a liver-associated disease, the method comprising administering to a subject having or suspected of having a liver-associated disease an effective amount of a grainyhead-like (GRHL) transcriptional regulator modulating agent.

In some aspects, the disclosure provides a method for treating a liver-associated disease, the method comprising: administering to a subject having or suspected of having a liver-associated disease an effective amount of an agent the increases expression of miR-122 in liver cells of the subject. In some embodiments, the agent is an inhibitor of a grainyhead-like (GRHL) transcriptional regulator (e.g., an inhibitory RNA targeting GRHL). In some embodiments, the agent inhibits expression of grainyhead-like 2 (GRHL2) transcriptional regulator, optionally spliced GRHL2. In some embodiments, the agent is a nucleic acid engineered to express miR-122.

Generally, a grainyhead-like (GRHL) transcriptional regulator modulating agent or a nucleic acid engineered to express miR-122 can be delivered to a cell or a subject by any suitable means known in the art. However, in some embodiments of methods described by the disclosure, a grainyhead-like (GRHL) transcriptional regulator modulating agent or a nucleic acid engineered to express miR-122 is delivered as a component (e.g., as a transgene encoded by) a recombinant AAV (rAAV). In some embodiments, the disclosure provides a method for treating a liver-associated disease, the method comprising: administering to a subject having or suspected of having a liver-associated disease an effective amount of a recombinant adeno-associated virus (rAAV) comprising a transgene encoding miR-122.

BRIEF DESCRIPTION OF DRAWINGS

(FIG. 1D) Hepatic miR-122 expression (FIG. 1C), serum ALT (FIG. 1E) and H&E histology and triglyceride concentrations (FIG. 1F) from the total livers of scrambled or miR-122-TuD treated WT mice after 5 weeks of control (PF) or alcohol (Et) diet. *P<0.05, P<0.005, *P<0.0005 by Student's t test or two-way ANOVA (n=6-14). Scale bars; 100 μm.

(FIG. 2C) The effect of miR-122-5p or scrambled oligonucleotide on luciferase activity from pmirCHECK-transfected HEK293T cells expressing the WT (3'UTR) of HIF-1 a (n=8). (FIG. 2D) HIF-1α mRNA in the total livers, (FIG. 2E) HIF-1α Electro-Mobility Shift Assay (EMSA) of hepatocyte nuclei, and (FIG. 2F) PPARγ mRNA in total livers isolated from Scr or miR-122-TuD treated WT mice after 5 weeks of PF or Et diet. *P<0.05, P<0.005, *P<0.0005 by Student's t test or two-way ANOVA (n=8-14).

(FIG. 4C) Scoring of collagen deposition, qPCR analysis of stellate cell activation markers Collagen1a1 (col1a1) and α-smooth muscle actin (Acta2). *P<0.05, P<0.005, *P<0.0005 by Student's t test or two-way ANOVA (n=6-14). Scale bars: 100 μm.

(FIG. 5A) miR-122, (FIG. 5B) serum ALT, (FIG. 5C) H&E histology and hepatic triglycerides, (FIG. 5D) hepatocyte HIF-1α expression and activity, (FIG. 5E) MCP-1 and IL-1ß protein treated from liver of either Et-fed WT mice treated with scAAV8-Scr or scAAV8-miR-122-OX vectors. (n=8-12) Scale bars; 100 μm.

FIGS. 6A-6F show grainyhead-like 2 inversely correlates with miR-122 expression in human livers. Pri-miR-122 expression in (FIG. 6A) human livers (n=10-12), alcohol-fed WT murine (FIG. 6B) livers (n=8-12) and hepatocytes (n=5). Pri-miR-122 expression in hepatocytes from pair-fed and alcohol-fed treated with either (FIG. 6C) miR-122-TuD, or miR-122-OX treated mice, and HIF-1α$^{hep-/-}$ mice. Chromosome immunoprecipitation-qPCR (ChIP-qPCR) of the GRHL binding results presented as % input of (FIG. 6D) GRHL2 and respective IgG controls. (FIG. 6E) GRHL2 mRNA expression in murine livers. (FIG. 6F) GRHL2 mRNA expression and correlation with miR-122 expression in human livers. *P<0.05, P<0.005, *P<0.0005 by Student's t test or two-way ANOVA (n=6-14).

(FIG. 7C) Immunostaining staining of isolated primary hepatocytes from PF- and Et-fed mice. Scale bars; PF=10 μm, Et=10 μm, Et+IgG=7.5 μm. Representative immunoblots for (FIG. 7D) murine (n=8) and (FIG. 7E) human (n=10) GRHL2 from total liver lysate. (FIG. 7F) The effect of GRHL2-FL or GRHL2-S miR-122 promoter activity (n=4). *P<0.05, P<0.005, *P<0.0005 by Student's t test.

(FIG. 11B) Gaussia Luciferase (Gluc) activity measured weekly from (n=3-5) alcohol-fed mice given 6×10$^{11}$ viral particles by tail vein injection. (FIG. 11C) Schematic representation of scAAV8-miR-122-OX treatment model. Liver (FIG. 11D) TNFa protein, (FIG. 11E) Mcp1, and (FIG. 11F) IL-1ß expression. *P<0.05, P<0.005, *P<0.0005 by Student's t test or two-way ANOVA.

FIGS. 13A-3B show a (FIG. 13A) a schematic representation of miR-122 promoter, transcription start site (TSS), Grainyhead (GRHL) dimer binding site and location of pre-miR-122 stem-loop.

(FIG. 14C) Immunostaining of FFPE liver sections from PF- and Et-fed mice. Scale bars; full-size=100 μm, inset=50 μm.

(FIG. 16A) Firefly luciferase activity driven by either a WT, Mut (mutated GRHL site, or truncated human miR-122 promoter in HUH7 cells. Each promoter was co-transfected with human cDNA clones of either the GRHL1-FL, GRHL2-FL, or GRHL2-S alone, or in combination. (FIG. 16B) expression of pri-miR-122 in primary human hepatocytes containing ectopically expressed either GRHL proteins as described above. Cells were incubated for 48 hours, then harvested for luciferase assay (FIG.

Figure 16A:
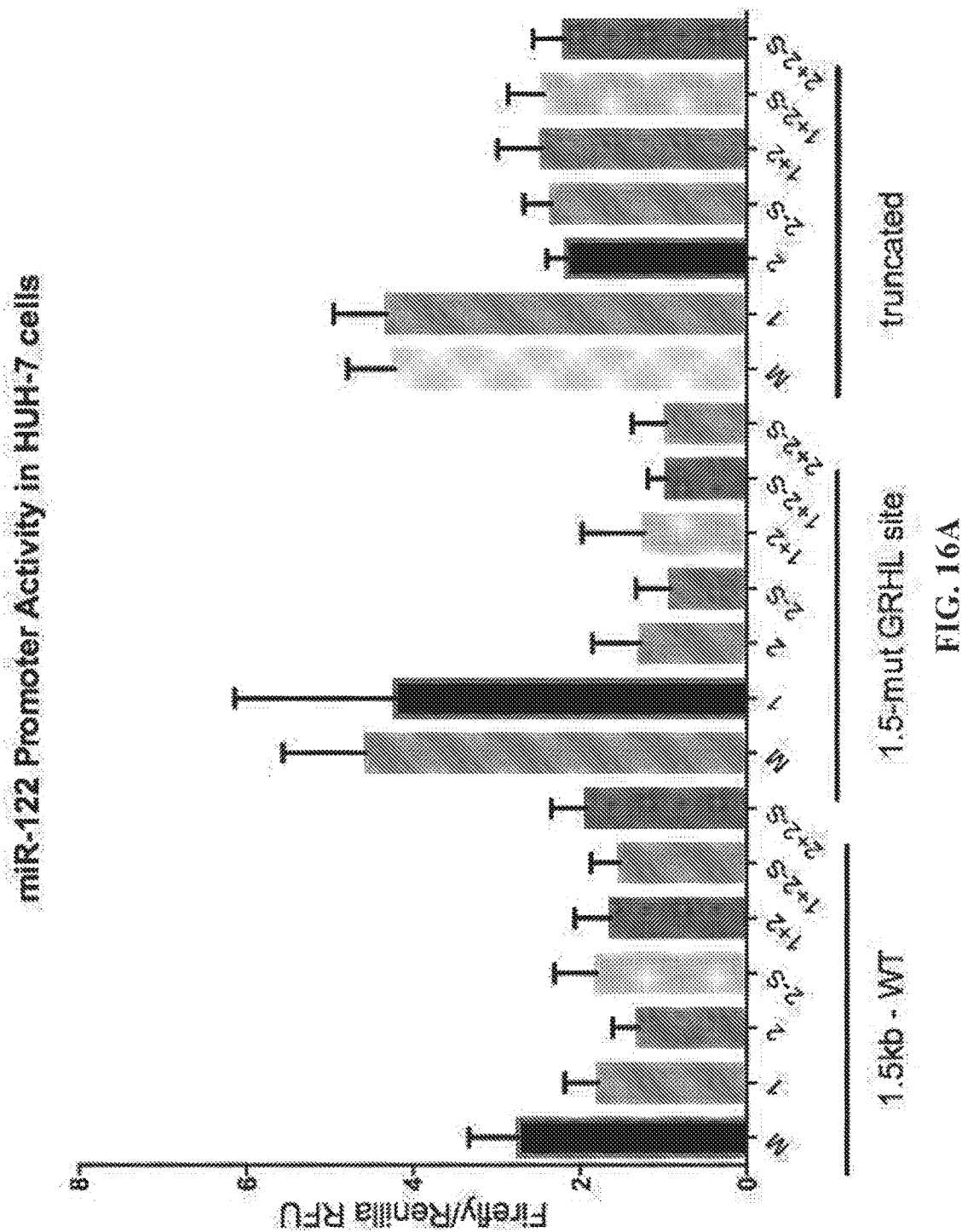
FIGS. 16A-16B show the role of grainyhead isoforms on miR-122 expression.
Figure 16B:
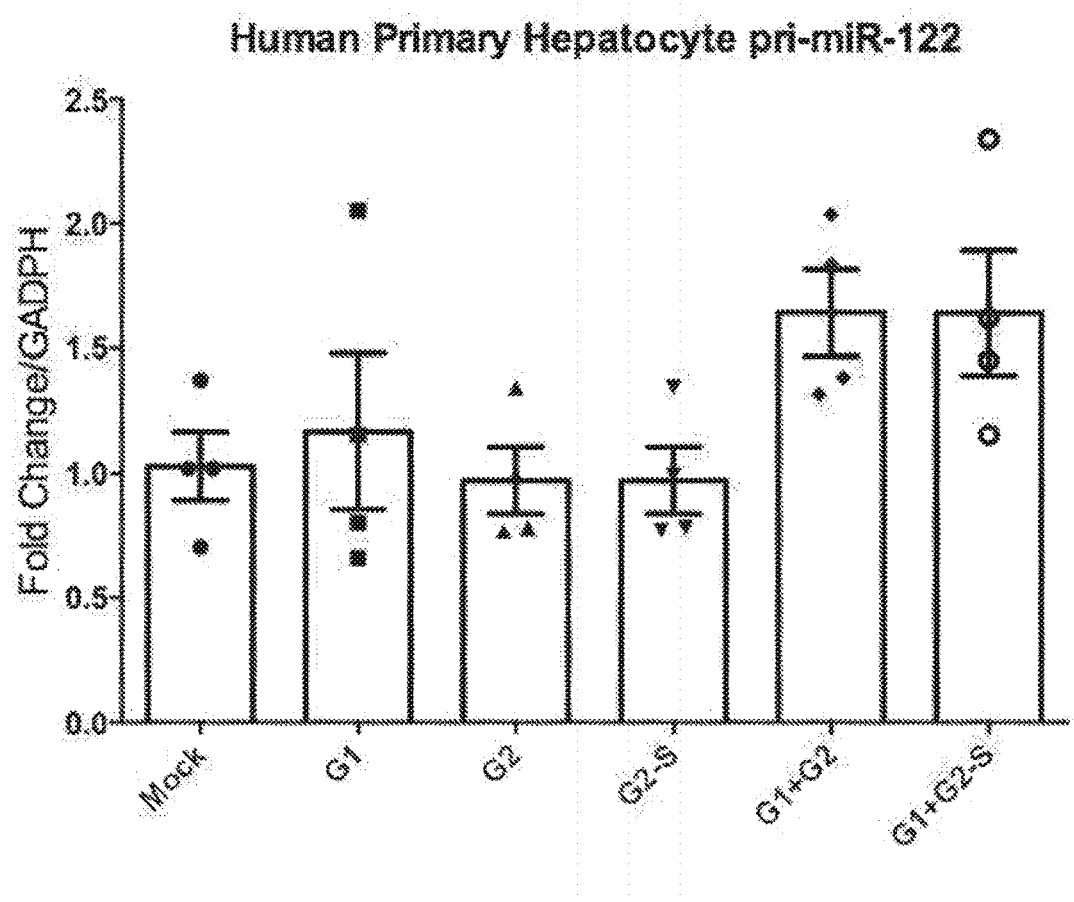

16A) or total RNA extracted for qPCR analysis (FIG. 16B). M=Mock, G1=GRHL1-FL, G2=GRHL2-FL, G2-S=GRHL2-Spliced.

DETAILED DESCRIPTION OF INVENTION

The present disclosure, in some aspects, includes a method for modulating miR-122 expression in a cell. In some embodiments, the methods involve contacting a cell with an effective amount of a grainyhead-like transcriptional regulator (GRHL) modulating agent. In some embodiments, the GRHL modulating agent modulates grainyhead-like 1 (GRHL1), grainyhead-like 2 (GRHL2), and/or grainyhead-like 3 (GRHL3) transcriptional regulator. In other embodiments, the GRHL modulating agent modulates grainyhead-like 2 (GRHL2) transcriptional regulator, optionally spliced GRHL2. In another embodiment, the cell is a hepatocyte. In some embodiments, the cell is a parenchymal hepatocyte, non-parenchymal hepatocyte, sinusoidal endothelial cell, Kupffer cell, hepatic stellate cell, or intrahepatic lymphocyte. In another embodiment, the grainyhead-like (e.g., GRHL2) modulating agent is a protein or a nucleic acid. In other embodiments, the grainyhead-like (e.g., GRHL2) modulating agent is an inhibitory nucleic acid. In another embodiment, the inhibitory nucleic acid is selected from the group consisting of dsRNA, siRNA, shRNA, pri-miRNA, miRNA, and artificial miRNA (amiRNA). In some embodiments, the miRNA or amiRNA is a tough decoy (TUD) miRNA. In another embodiment, the nucleic acid is flanked by adeno-associated virus (AAV) inverted terminal repeats (ITRs). In some embodiments, the nucleic acid is encapsidated by one or more adeno-associated virus (AAV) capsid protein. In other embodiments, the one or more capsid protein is a liver-trophic capsid protein. In some embodiments, the one or more capsid protein is an AAV2, AAV3, AAV3b, AAV7, AAV8, or AAV9 capsid protein.

The present disclosure, in some aspects, includes a method for modulating hypoxia-inducible factor 1α (HIF-1α) expression in a liver cell of a subject having a liver-associated disease, the method comprising increasing expression of miR-122 in the cell. In some embodiments, the expression of miR-122 is increased by delivering to the cell a nucleic acid engineered to express miR-122. For example, in some embodiments, a nucleic acid engineered to express miR-122 comprises a recombinant adeno-associated virus (rAAV) vector comprising a transgene encoding miR-122.

In some embodiments, the nucleic acid engineered to express miR-122 comprises a promoter (e.g. a promoter operably linked to a transgene encoding miR-122). A promoter can be an inducible promoter, a constitutive promoter, a tissue-specific promoter (e.g. a liver-specific promoter, such as the human thyroxine binding globulin (TBG) promoter), or any suitable combination of the foregoing.

In some embodiments, the cell is a hepatocyte. In other embodiments, the hepatic cell is a parenchymal hepatocyte, non-parenchymal hepatocyte, sinusoidal endothelial cell, Kupffer cell, hepatic stellate cell, or intrahepatic lymphocyte. In another embodiment, the hypoxia-inducible factor 1α (HIF-1α) modulating agent is a protein or a nucleic acid. In some embodiments, the hypoxia-inducible factor 1α (HIF-1α) modulating agent is an inhibitory nucleic acid. In another embodiment, the inhibitory nucleic acid is selected from the group consisting of dsRNA, siRNA, shRNA, pri-miRNA, miRNA, and artificial miRNA (amiRNA). In some embodiments, the miRNA or amiRNA is a tough decoy (TUD) miRNA. In other embodiments, the nucleic acid is flanked by adeno-associated virus (AAV) inverted terminal repeats (ITRs). In some embodiments, the nucleic acid is encapsidated by one or more adeno-associated virus (AAV) capsid protein. In other embodiments, the one or more capsid protein is a liver-trophic capsid protein. In another embodiment, the one or more capsid protein is an AAV2, AAV3, AAV3b, AAV7, AAV8, or AAV9 capsid protein.

The present disclosure, in some aspects, includes a method for treating a liver-associated disease, the method comprising: administering to a subject having or suspected of having a liver-associated disease an effective amount of a grainyhead-like (GRHL) transcriptional regulator modulating agent or a nucleic acid engineered to express miR-122. In some embodiments, the GRHL modulating agent modulates grainyhead-like 1 (GRHL1), grainyhead-like 2 (GRHL2), and/or grainyhead-like 3 (GRHL3) transcriptional regulator. In other embodiments, the GRHL modulating agent modulates grainyhead-like 2 (e.g., GRHL2) transcriptional regulator. In another embodiment, the subject is a mammal, optionally a human. In some embodiments, the liver-associated disease is characterized by a decrease in miR-122 expression relative to a subject not having the liver-associated disease. In another embodiment, the liver-associated disease is alcoholic liver disease (ALD), cirrhosis, hepatitis A, hepatitis B, hepatitis C, hepatocellular carcinoma (HCC), or fibrosis of the liver. In another embodiment, the grainyhead-like (e.g., GRHL2) modulating agent increases miR-122 expression in the subject. In some embodiments, the grainyhead-like (e.g., GRHL2) modulating agent decreases miR-122 expression, or decreases HIF-1α expression, in the subject. In another embodiment, the grainyhead-like (e.g., GRHL2) modulating agent is a protein or a nucleic acid. In other embodiments, the nucleic acid is an inhibitory nucleic acid. In another embodiment, the inhibitory nucleic acid is selected from the group consisting of dsRNA, siRNA, shRNA, pri-miRNA, miRNA, and artificial miRNA (amiRNA). In some embodiments, the miRNA or amiRNA is a tough decoy (TUD) miRNA. In another embodiment, the grainyhead-like (e.g., GRHL2) modulating agent nucleic acid engineered to express miR-122 is administered to the subject in a recombinant adeno-associated virus (rAAV). In another embodiment, the rAAV comprises one or more AAV capsid protein. In other embodiments, the one or more capsid protein is a liver-trophic capsid protein. In some embodiments, the one or more capsid protein is an AAV2, AAV3, AAV3b, AAV7, AAV8, or AAV9 capsid protein.

The present disclosure, in some aspects, includes a method for treating a liver-associated disease, the method comprising: administering to a subject having or suspected of having a liver-associated disease an effective amount of a recombinant adeno-associated virus comprising a transgene encoding miR-122. In some embodiments, the subject is a mammal, optionally a human. In other embodiments, the liver-associated disease is alcoholic liver disease (ALD), cirrhosis, hepatitis A, hepatitis B, hepatitis C, hepatocellular carcinoma (HCC), or fibrosis of the liver. In other embodiments, the transgene encoding miR-122 comprises a sequence represented by SEQ ID NO: 1 or SEQ ID NO: 2. In another embodiment, the rAAV comprises a liver-trophic capsid protein. In some embodiments, the capsid protein is an AAV2, AAV3, AAV3b, AAV7, AAV8, or AAV9 capsid protein.

Grainyhead-Like (GRHL) Proteins

Grainyhead-like (GRHL) transcription factors have been observed to play regulatory roles during development, for example by acting as an activator and/or repressor of distinct target genes. The GRHL transcription factor family encompasses GRHL transcription factors GRHL1-3. For example, amino acid sequences of human GRHL1-3 are provided in Table 1.

TABLE 1

Human GRHL1-3.

| Protein | No. of AA | GenBank Accession No. | UniProt ID | SEQ ID NO: |
|---------|-----------|----------------------|------------|------------|
| GRHL1 | 618 | NP_937825.2 | Q9NZI5 | 31 |
| GRHL2 | 625 | NP_079191.2 | Q6ISB3 | 32 |
| GRHL3 | 626 | NP_067003.2 | Q8TE85 | 33 |

GRHL1-3 are structurally similar, each containing an evolutionarily conserved CP2 DNA binding domain flanked by an N-terminal transactivation domain and a C-terminal DNA binding domain. In fact, an amino acid sequence comparison reveals that the human homologue of murine GRHL1 to be 94% identical at the amino acid level. Further, GRHL1 and GRHL2 share 90% sequence homology at the amino acid level. In general, each protein has a N-terminal transactivation domain, a linker region, and a C-terminal dimerization domain.

The GRHL modulating agent to be used in the methods described herein can be a molecule that modulates (e.g., reduces or enhances) the expression level or biological activities of any one of GRHL1-3. In some embodiments, the term "GRHL modulating agent" refers to an agent that modulates GRHL (e.g., GRHL1, GRHL2, or GRHL3) levels and/or activity (including but not limited to its ability to decrease miR-122 expression), e.g., by at least 20%, 50%, 70%, 85%, 90%, 100%, 150%, 200%, 300%, or 500%, or by 10-fold, 20-fold, 50-fold, 100-fold, 1000-fold, or $10^4$-fold.

As shown herein, GRHL inhibits the expression of miR-122, and GRHL and miR-122 levels may vary by cell type. In some embodiments, a hepatocyte refers to a fully or partially differentiated cell of hepatocyte lineage arising from endoderm. In some embodiments, a mature hepatocyte expresses detectable to relatively high levels of albumin. Accordingly, in some embodiments, albumin is a marker for of a mature hepatocyte. The term "biliary cells" refers to hepatic biliary cells which line the bile ducts.

In some embodiments, GRHL1 is expressed (e.g., constitutively) in hepatocytes. In some embodiments, GRHL2 is predominantly expressed in biliary cells. In some embodiments, the expression level of GRHL is inversely proportional to miR-122. In some embodiments, miR-122 expression in biliary cells is low. In some embodiments, miR-122 expression is lower in biliary cells than miR-122 expression in hepatocytes. In some embodiments, miR-122 expression is lower in immature hepatocytes than miR-122 expression in mature hepatocytes.

Recombinant AAVs

In some aspects, the disclosure relates to delivery of a modulator (e.g., grainyhead-like (GRHL) transcriptional regulator modulating agent) or a nucleic acid engineered to express miR-122 (e.g., a rAAV vector comprising a transgene encoding miR-122, such as pri-miR-122). In some embodiments, a composition described by the disclosure is delivered to a cell using an isolated recombinant adeno-associated virus (rAAV).

As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art. The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein.

The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

Administration

In some embodiments, a modulator (e.g., grainyhead-like (GRHL) transcriptional regulator modulating agent or a nucleic acid engineered to express miR-122 (e.g., a rAAV vector comprising a transgene encoding miR-122, such as pri-miR-122) is delivered to a cell (e.g., administered to a patient in need thereof) as a recombinant adeno-associated virus (rAAV). The component can be fused to the capsid protein (e.g., VP2) of the rAAV, encoded as a transgene in an rAAV vector, or a combination of the foregoing.

rAAVs may be delivered to a subject in compositions according to any appropriate methods known in the art. The rAAV, preferably suspended in a physiologically compatible carrier (e.g., in a composition), may be administered to a subject, e.g., host animal, such as a human, mouse, rat, cat, dog, sheep, rabbit, horse, cow, goat, pig, guinea pig, hamster, chicken, turkey, or a non-human primate (e.g., Macaque). In some embodiments, a host animal is a human. In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the liver of a subject (e.g., deliver a transgene using a rAAV having a liver-trophic AAV capsid protein).

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{12}$ or $10^{13}$ rAAV genome copies is effective to target heart, liver, and pancreas tissues. In some cases, stable transgenic animals are produced by multiple doses of an rAAV.

GRHL Modulating Agents

Grainyhead-like transcriptional regulator (GRHL) modulating agents can be used in methods described herein. In some embodiments, a GRHL modulating agent (e.g., a small molecule inhibitor or a peptide inhibitor) inhibits binding of GRHL to a miR-122 promoter or other regulatory element thereby inhibiting expressing of miR-122. In some embodiments the GRHL modulating agent inhibits expression of GRHL (e.g., an interfering RNA that targets GRHL mRNA).

In other embodiments, the GRHL modulating agent comprises at least one GRHL inhibitory compound. As used herein, "GRHL inhibitory compound" refers to a compound that directly or indirectly reduces, inhibits, neutralizes, or abolishes GRHL biological activity. In some embodiments, a GRHL inhibitory compound exhibits any one or more of the following characteristics: (a) binds to GRHL mRNA or protein and inhibits its biological activity and/or downstream pathways mediated by GRHL; (b) increases expression of miR-122; (c) decreases expression of HIF-1α; and/or (d) reduces liver damage, steatosis, and/or inflammation. One skilled in the art can prepare other small molecules inhibitory compounds.

In some embodiments, the GRHL inhibitory compounds described herein are small molecules, which can have a molecular weight of about any of 100 to 20,000 Daltons, 500 to 15,000 Daltons, or 1000 to 10,000 Daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the GRHL modulating agent according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The small molecules referred to herein can be obtained from compound libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

Alternatively, the GRHL modulating agent may be an agent that decreases GRHL expression, for example, morpholino oligonucleotides, small interfering RNA (siRNA or RNAi), antisense nucleic acids, or ribozymes (e.g., that specifically target GRHL mRNA and inhibit its translation and/or brings about its degradation). RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene (e.g., a mRNA sequence encoding an amino acid sequence as set forth in SEQ ID NO: 31-33).

In some embodiments, the GRHL modulating agent may be a nucleic acid aptamer that binds to GRHL and inhibits its activity (anti-GRHL aptamers), thereby increasing levels of miR-122. A nucleic acid aptamer as used herein refers to a nucleic acid molecule (DNA or RNA) having a binding activity for a particular target molecule (e.g., GRHL). The aptamer can inhibit the activity of a particular target molecule by binding to the particular target molecule. The anti-GRHL aptamer of the present disclosure, in linear or circular form, may be an RNA, a DNA (e.g., a single-stranded DNA), a modified nucleic acid, or a mixture thereof. The anti-GRHL aptamers may be non-naturally occurring molecules (e.g., containing a nucleotide sequence not existing in native genes or containing modified nucleotides not existing in nature). Alternatively or in addition, the anti-GRHL aptamers may contain a nucleotide sequence that encodes a functional peptide.

In some embodiments, the GRHL modulating agent increases expression of GRHL (e.g., nucleic acids encoding GRHL). Plasmid vectors for expression of GRHL, or a fragment thereof, include conventional control elements which are operably linked to the nucleic acids encoding GRHL in a manner which permits its transcription, translation and/or expression in a cell transfected with the plasmid vector. As used herein, "operably linked" sequences include both expression control sequences that are contiguous with the gene of interest and expression control sequences that act in trans or at a distance to control the gene of interest. However, in some embodiments, the GRHL modulating agent is a synthetic GRHL mRNA that may be delivered to cells to increase expression of a GRHL protein.

In some embodiments, the GRHL modulating agent increases expression of a mutated GRHL. In some embodiments, the mutated GRHL comprises one or more mutations in the DNA binding domain. In some embodiments, the mutated GRHL comprises one or more mutations in the transactivation domain. In some embodiments, the one or more mutations is at least one, at least two, at least three, at least four, at least five, at least six, at least seven, at least eight, at least nine, at least ten, at least fifteen, at least twenty, or at least twenty five mutations in the DNA binding domain and/or the transactivation domain.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promotors which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA).

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and 0-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

Methods of Use

In some embodiments, to practice methods disclosed herein, an effective amount of a GRHL modulating agent, a HIF-1α modulating agent, or a transgene encoding miR-122 described herein can be administered to a subject (e.g., a human) in need of the treatment via a suitable route (e.g., intravenous administration).

In some embodiments, the subject to be treated by the methods described herein can be a human patient having, suspected of having, or at risk for a liver associated disease. Examples of a liver associated disease include, but are not limited to, alcoholic liver disease (ALD), cirrhosis, hepatitis A, hepatitis B, hepatitis C, hepatocellular carcinoma (HCC), liver cancer, and fibrosis of the liver. Examples of liver cancer include, but are not limited to, hepatocellular carcinoma (HCC), fibrolamellar HCC, cholangiocarcinoma, angiosarcoma, or secondary liver cancer.

In some embodiments, the subject to be treated by the methods described herein can be a human patient having, suspected of having, or at risk for cancer. Examples of cancer include, but are not limited to, squamous cell carcinoma of the skin, breast cancer, gastric cancer, hepatocellular carcinoma, colorectal cancer, clear cell renal cell carcinoma, neuroblastoma, prostate cancer, and cervical cancer.

In some embodiments, the subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a liver-associated disease (e.g., ALD). In some embodiments, a subject having a liver-associated disease can be identified by routine medical examination, e.g., laboratory tests, biopsy, CT scans, or ultrasounds. In some embodiments, a subject suspected of having a liver-associated disease might show one or more symptoms of the disorder, e.g., unexplained weight loss, fever, fatigue, pain, nausea, and/or jaundice. In some embodiments, a subject at risk for a liver-associated disease can be a subject having one or more of the risk factors for that disorder. For example, risk factors associated with a liver-associated disease include (a) viral infection (e.g., hepatitis virus infection), (b) age, (c) family history, (d) heavy alcohol consumption, (e) drug use, and (f) iron overload.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a liver-associated disease. Alternatively, sustained continuous release formulations of a GRHL modulating agent, a HIF-1α modulating agent, or a transgene encoding miR-122 may be appropriate. Various formulations and devices for achieving sustained release are known in the art.

In one example, dosages for a GRHL modulating agent, a HIF-1α modulating agent, or a transgene encoding miR-122 as described herein may be determined empirically in individuals who have been given one or more administration(s) of GRHL modulating agent, HIF-1α modulating agent, or transgene encoding miR-122. Individuals are given incremental dosages of the GRHL modulating agent, the HIF-1α modulating agent, or the transgene encoding miR-122. To assess efficacy of the agents, an indicator of a liver-associated disease (miR-122 expression levels) can be followed.

As used herein, the term "treating" refers to the application or administration of a composition including one or more active agents to a subject, who has a liver-associated disease, a symptom of a liver-associated disease, or a predisposition toward a liver-associated disease, with the purpose to cure, heal, alleviate, relieve, alter, remedy, ameliorate, improve, or affect the disorder, the symptom of the disease, or the predisposition toward a liver-associated disease.

Alleviating a liver-associated disease includes delaying the development or progression of the disease, or reducing disease severity. Alleviating the disease does not necessarily require curative results. As used herein, "delaying" the development of a disease (such as ALD) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a liver-associated disease includes initial onset and/or recurrence.

In some embodiments, it is also apparent that a therapeutic effect of a GRHL modulating agent, a HIF-1α modulating agent, or a transgene encoding miR-122 as described herein may be to stimulate hepatocyte growth. Thus, in some embodiments, the therapeutic effect is improvement of liver function. In some embodiments, the therapeutic effect is replication of hepatocytes, biliary epithelial cells, and/or sinusoidal endothelial cells. Alternatively or in addition, the therapeutic effect is liver regeneration. In some embodiments, liver regeneration comprises regeneration of liver tissue following a liver resection. In some embodiments, liver regeneration comprises regeneration of liver tissue following a liver transplantation.

In other aspects, the methods described herein are based, at least in part, on the identification of biomarkers that were found to be differentially present in liver-associated disease (e.g., alcoholic liver disease) as compared to a non-disease. As used herein, the term "biomarker" or "biomarker set" indicative of a specific population of cells (e.g., hepatocytes) refers to a biological molecule (e.g., GRHL) or set of such biological molecules that are present at a level in that specific population of cells that deviates from a level of the same molecule in a different population of cells. For example, a biomarker that is indicative of a liver-associated disease may have an elevated level or a reduced level in liver-associated disease as relative to the level of the same marker in non-liver-associated-disease. The liver-associated disease biomarkers described herein may have a level in liver-associated disease that deviate from (enhanced or reduced) the level of the same marker in non-liver-associated disease by at least 10% (e.g., 15%, 30%, 50%, 75%, 100%, 2-fold, 5-fold, 10-fold, 20-fold, 50-fold, 100-fold or more). Such biomarker/biomarker sets may be used in both diagnostic/prognostic applications and non-clinical applications (e.g., for research purposes).

EXAMPLE

Inhibition Of MiRNA-122 Expression by Grainyhead-Like 2 Promotes Alcoholic Liver Disease through HIF-1α Activation in Hepatocytes Chronic alcohol consumption accounts for nearly 50% of liver-related death in the United States, however, no effective therapies exist for patients. While early steatosis in ALD is reversible, chronic, excessive alcohol consumption leads to cirrhosis and it is the single greatest cause of hepatocellular cancer (HCC). Acute alcoholic hepatitis has a 30%-50% 30-day mortality and the standard of care with steroids has limited benefits and significant side effects. Thus, identification of novel therapeutic targets is a major clinical need in ALD.

Alcoholic liver disease is characterized by liver steatosis, inflammation and progressive fibrosis with prolonged alcohol use. Alcohol-triggered hepatocyte steatosis and cell death results in the activation and infiltration of immune cells within the liver leading to advanced hepatic injury. The subsequent release of inflammatory cytokines causes further hepatocyte cell death resulting in perpetuation of liver injury.

Hepatic microRNAs (miRNAs) have crucial roles in maintaining liver homeostasis, mitochondrial function, and regulating oncogenesis. miR-122 constitutes 70% of all miRNAs in mature hepatocytes, or approximately 130,000 copies per cell, with negligible expression in other cells and tissues. Germ line deletions of miR-122 display steatosis at birth, spontaneous progression to fibrosis, and HCC. In humans, liver miR-122 expression inversely correlates with HCC survival and metastasis, while miR-122 inhibition reduces HCV viremia, serum triglycerides, and cholesterol.

Encoded on chromosome 18 in mice and humans, miR-122 is transcribed as a ~4.7 kb noncoding pri-miRNA transcript by RNA polymerase II which is then rapidly processed into a 66-nucleotide (nt) pre-miR-122 by Drosha. Subsequently, the pre-miRNA is shuttled into the cytoplasm where it is processed into its mature 23-nt form. In the liver, its abundance and specificity to hepatocytes is regulated at the transcriptional level by a host of liver-specific transcription factors including hepatocyte nuclear factors (HNFs) 1α, 3β, 4α, and 6α. While factors which maintain the high level of expression of miR-122 in the healthy liver have been well studied, little is known about the epigenetic regulation of its expression in disease states.

Figures 1A, 1B, 1C:
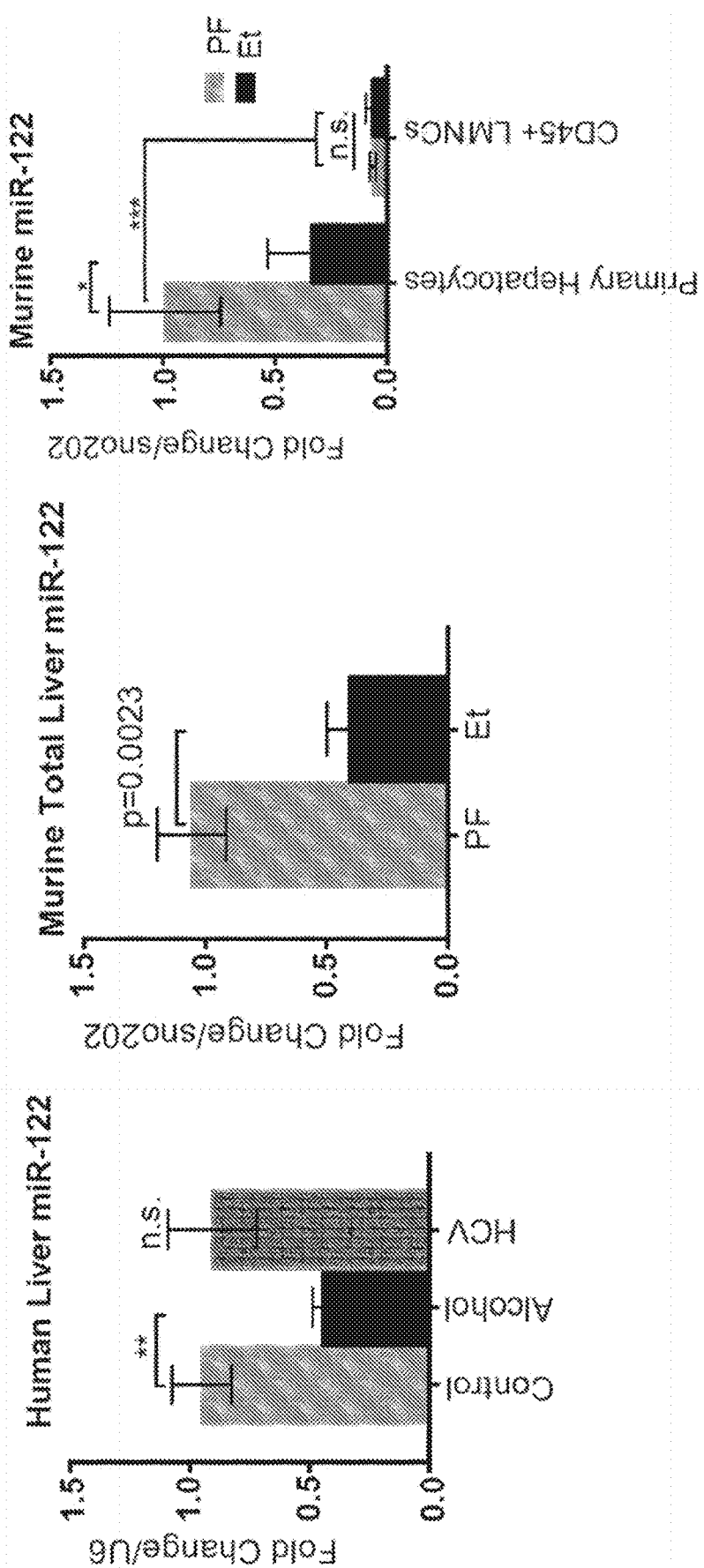
FIGS. 1A-1F show chronic alcohol use is associated with reduced miR-122 expression. Expression of miR-122 in (FIG. 1A) total human liver (n=9-12), murine (FIG. 1B) total liver (n=8-14), (FIG. 1C) murine hepatocytes and CD45+ liver mononuclear cells (LMNCs) of pair-fed and alcohol-fed mice (n=5).

In this example, effects alcohol use on modulation of miR-122 in the liver was examined. The significant reduction of miR-122 expression in hepatocytes due to epigenetic inhibition of transcription by chronic alcohol-induced grainyhead family of transcription factors is demonstrated. Data indicate that reduction of miR-122 regulates the pathogenesis of ALD through its primary target, HIF-1α, in hepatocytes. Therapeutic benefit of miR-122 restoration in hepatocytes is demonstrated using viral vector-mediated gene therapy.

miR-122 Expression is Decreased in Livers and Hepatocytes After Chronic Alcohol use in Humans and Mice Investigation of diseased livers revealed that miR-122 expression was significantly reduced (by 2-fold) in patients with alcoholic cirrhosis when compared to HCV cirrhosis or healthy controls, (FIG. 1A, Table 1) suggesting that chronic alcohol may promote liver injury by inhibiting miR-122. To further dissect the role of miR-122, a chronic alcohol feeding model of ALD in mice was used. miR-122 expression was significantly reduced in the livers of alcohol-fed mice compared to pair-fed controls (FIG. 1B) and the extent of reduction was equivalent to that seen in human patients.

To determine the cell specificity of the miR-122 reduction, primary hepatocytes and liver mononuclear cells (LMNCs) were isolated. miR-122 was selectively decreased in hepatocytes and not in CD45+ LMNCs from alcohol-fed mice (FIG. 1C) when compared to pair-fed controls. This data indicates that alcohol-induced changes in miR-122 in the total liver are hepatocyte-specific.

miR-122 Reduction in Hepatocytes Mimics Alcoholic Liver Disease

Given the miR-122 reduction observed after chronic alcohol in murine hepatocytes, the ability of inhibition of miR-122 in vivo to mimic features of alcoholic liver disease was investigated. To inhibit miR-122 in vivo, a self-complimentary adeno-associated virus 8 (scAAV8) vector system expressing an anti-miR-122 Tough Decoy (TuD) was produced. This scAAV8 has tropism for hepatocytes and maintains sustained inhibition of miR-122 in murine livers.

Figure 10A:
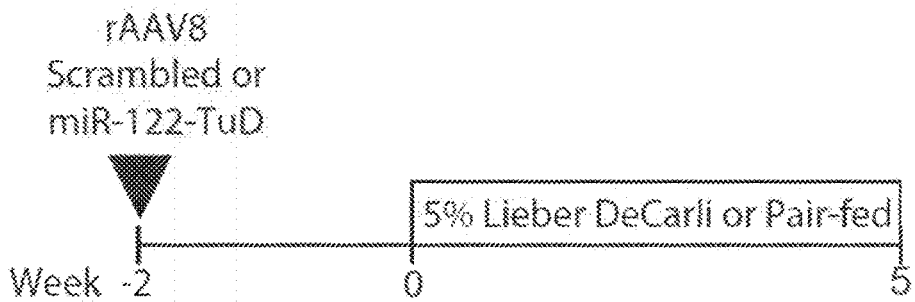
FIGS. 10A-10G show (FIG. 10A) 5-week Lieber Di-Carli chronic alcohol feeding model. Hepatic expression of (FIG. 10B) miR-122, (FIG. 10C) Serum ALT F4/80, (FIG. 10D) CD68, (FIG. 10E) pro-IL1ß, (FIG. 10F) MCP1, and (FIG. 10G) Tgfß1 in scrambled or miR-122-TuD treated WT or HIF-1α$^{hep-/-}$ mice after 5 weeks of control (PF) or alcohol (Et) diet. *P<0.05, P<0.005, *P<0.0005 by Student's t test or two-way ANOVA (n=6-14).

Wild type (WT) mice were treated with scAAV8-scrambled (Scr) or scAAV8-anti-miR-122-TuD (miR-122 TuD) 2-weeks prior to initiation of the chronic alcohol feeding to permit full vector expression (FIG. 10A).

Figure 1D:
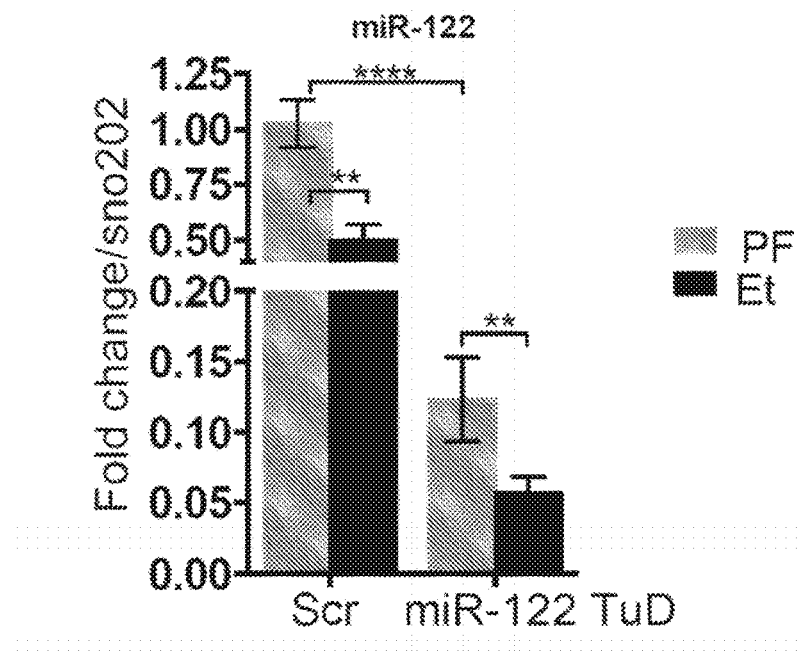
Figure 1E:
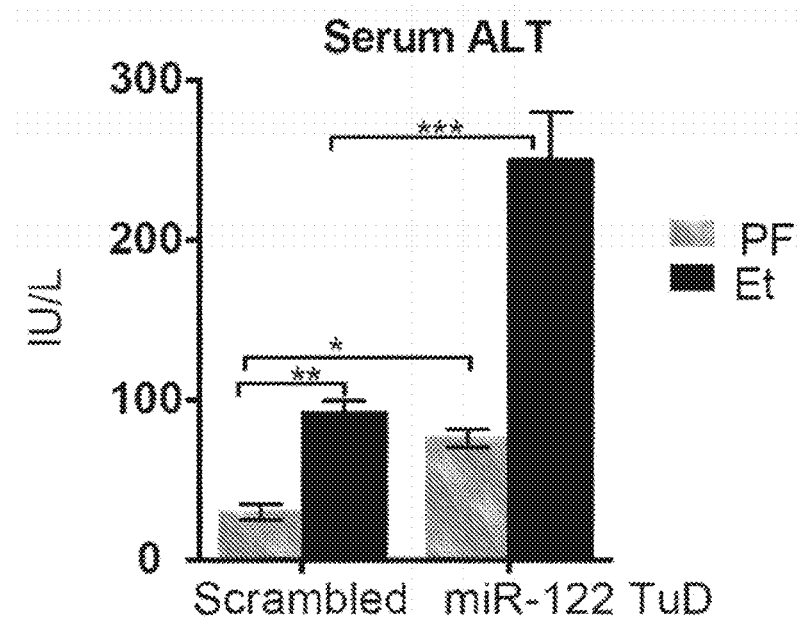
Figure 1F:
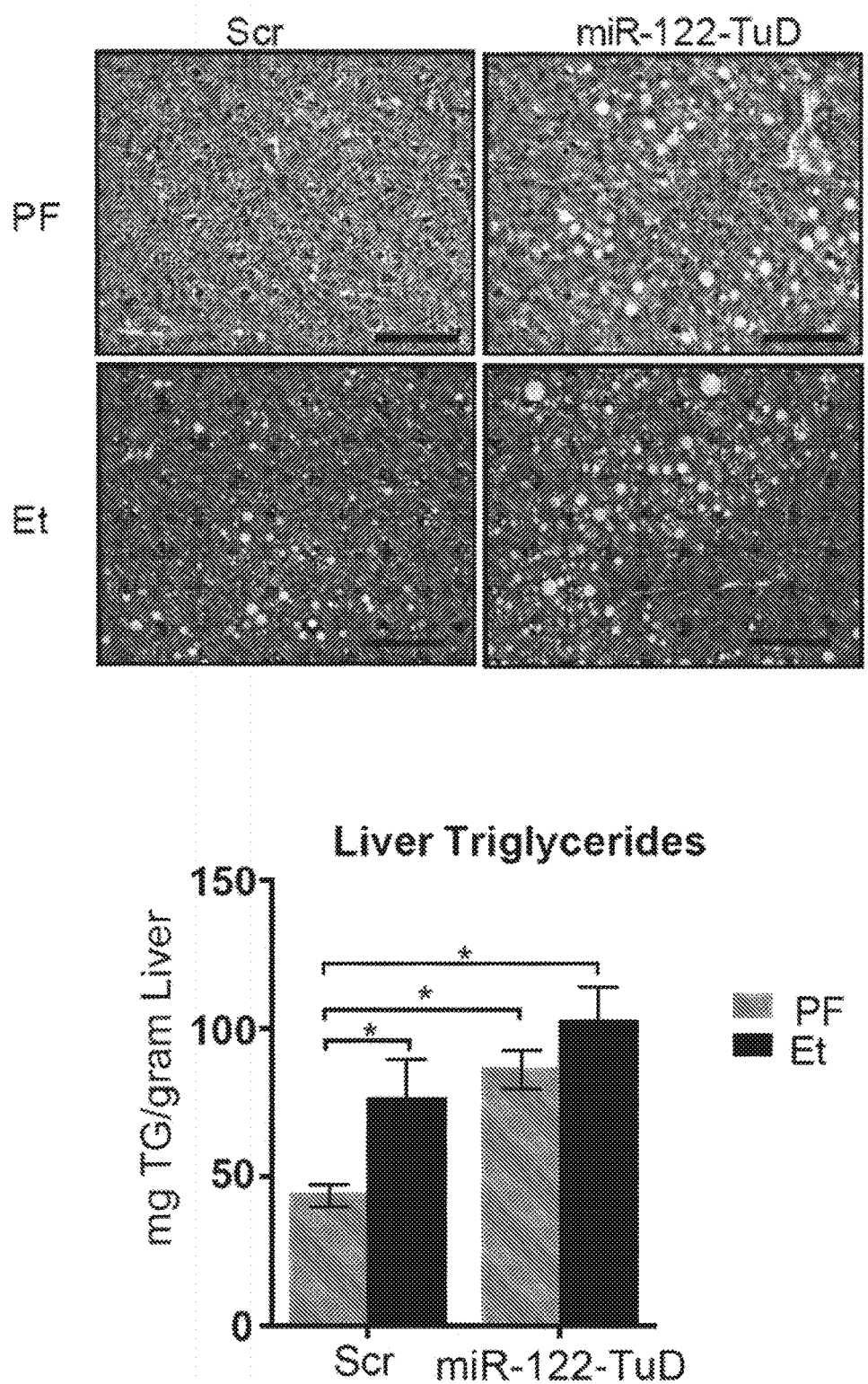

In WT mice, scAAV8 miR-122 TuD achieved a robust and sustained knockdown of miR-122 in both pair-fed and alcohol-fed mice (FIG. 1D). Interestingly, in addition to the scAAV8 miR-122 TuD-induced reduction, liver miR-122 levels were further decreased by ethanol feeding compared to pair-fed TuD treated mice (FIG. 1D). TuD-mediated inhibition of miR-122 alone resulted in a significant increase in serum ALT (FIG. 1E) and hepatic steatosis (FIG. 1F) that was equivalent to that induced by the alcohol-diet. The combination of alcohol plus miR-122-TuD treatment resulted in a synergistic effect further increasing serum ALT (FIG. 1E) hepatic lipid accumulation (FIG. 1F) and this correlated with decreasing miR-122 expression in hepatocytes (FIG. 1D).

miR-122 Directly Regulates HIF-1α in Hepatocytes

Figure 2A:
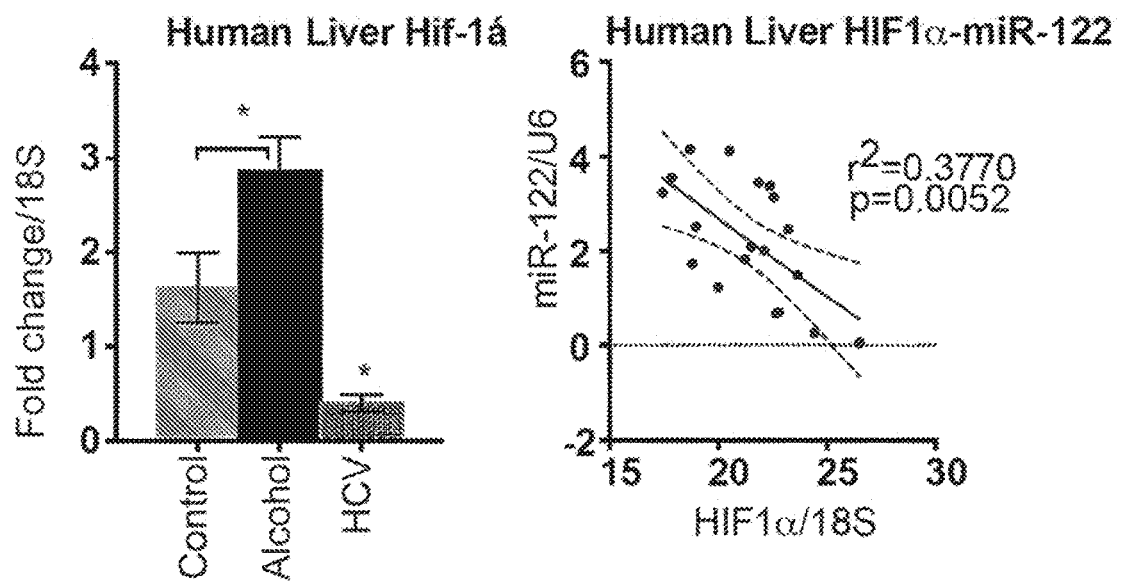
FIGS. 2A-2F show chronic alcohol is associated with increased HIF-1α expression. Expression of HIF-1α and correlation to miR-122 expression in (FIG. 2A) human livers (n=9-12), and (FIG. 2B) murine hepatocytes (n=8-14).
Figure 2B:
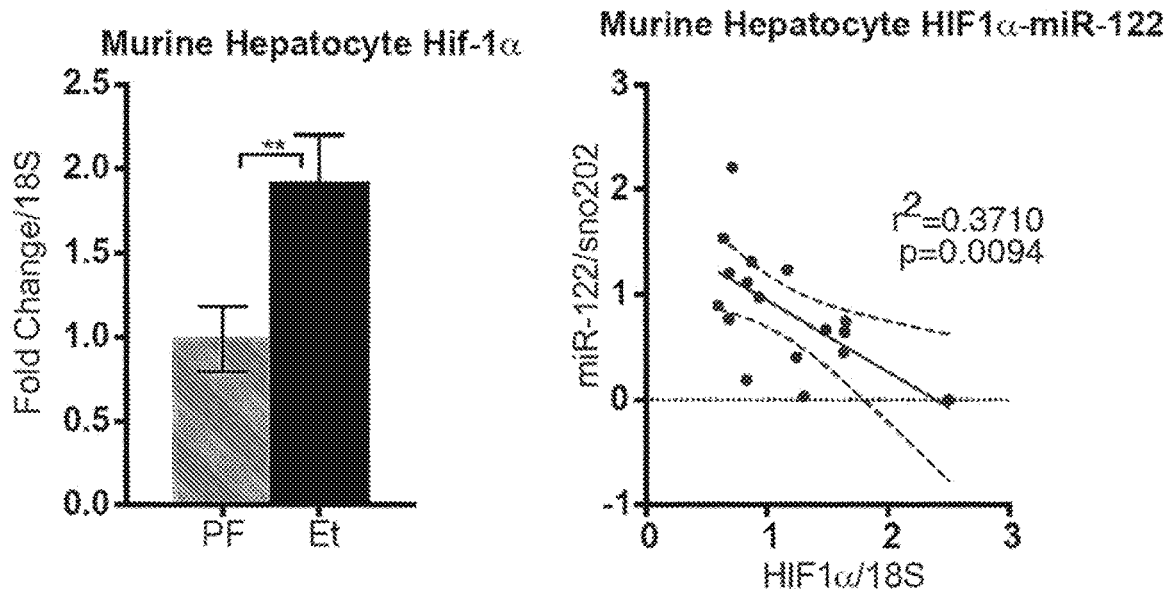

To assess mechanism by which miR-122 decrease could mediate liver injury and steatosis, potential miR-122 targets that may contribute to the development of ALD were examined. Using the TargetScan algorithm, based on seed recognition, HIF-1α was identified as a putative target of miR-122. Generally, alcohol increases HIF-1α expression in hepatocytes and hepatocyte-specific HIF-1α knockout mice (HIF1α$^{hep-/-}$) were protected from chronic alcohol, while transgenic mice, expressing a constitutively active form of HIF1α (HIF1dPA) in hepatocytes, had augmented alcohol-induced liver injury. However, a direct relationship between miR-122 and HIF-1α is yet to be explored. This analysis of the livers of alcoholic cirrhosis patients and hepatocytes of alcohol-fed mice revealed an increase of HIF-1α mRNA that showed a significant inverse correlation with miR-122 expression (FIGS. 2A-2B; p=0.0052, r$^2$=0.3770 and p=0.0094, r$^2$=0.3710 respectively). This correlation indicated that HIF-1α regulation by miR-122 in hepatocytes may be a key element in the pathogenesis of ALD.

Figure 2C:
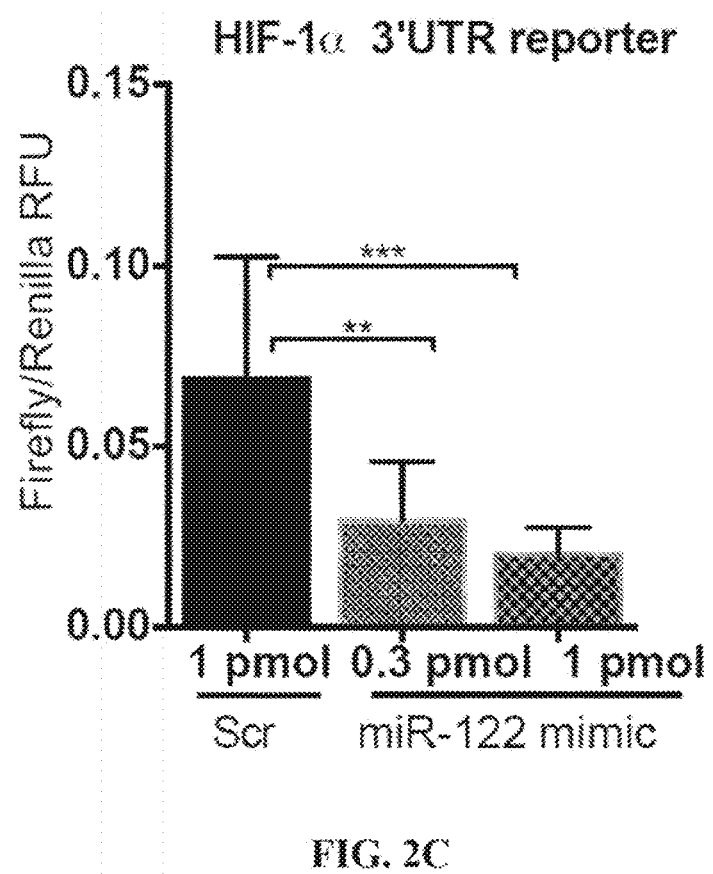
Figure 9A:
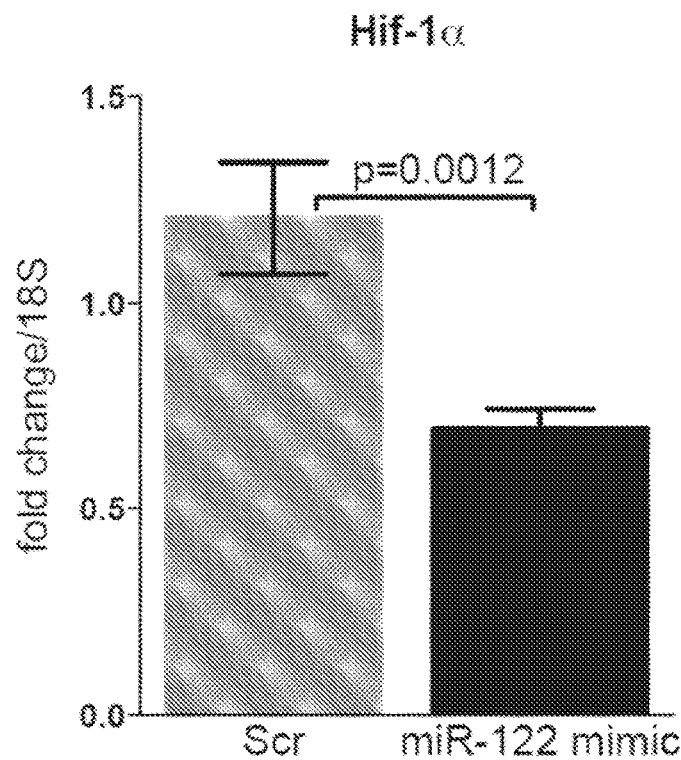
FIGS. 9A-9B show HIF-1α mRNA expression in human hepatocytes treated with either (FIG. 9A) miR-122 mimic or (FIG. 9B) anti-miR-122 inhibitor. P value calculated by Student's t test (n=12).
Figure 9B:
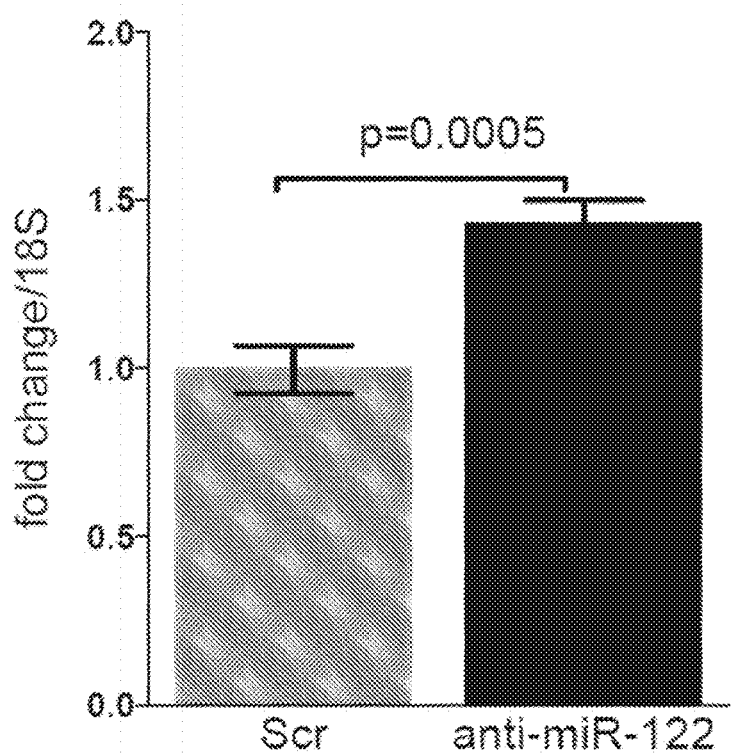

To establish that miR-122 directly regulates HIF-1α through canonical miRNA pathways, a plasmid containing the HIF-1α 3'UTR-luciferase reporter (HIF-3'luc, Origene) was cotransfected with scrambled or miR-122 mimic into HEK293T cells. The miR-122 mimic strongly repressed HIF-3'luc activity in a dose-dependent manner (FIG. 2C). As further evidence of the miR-122/HIF-1α regulatory pathway, it was found that transfection of a miR-122 mimic or an inhibitor into primary murine hepatocytes results in decreased or increased HIF-1α mRNA, respectively (FIGS. 9A-9B). These results confirmed that miR-122 directly inhibits HIF-1α expression in hepatocytes.

miR-122 Regulates HIF-1α In Vivo

Figure 2D:
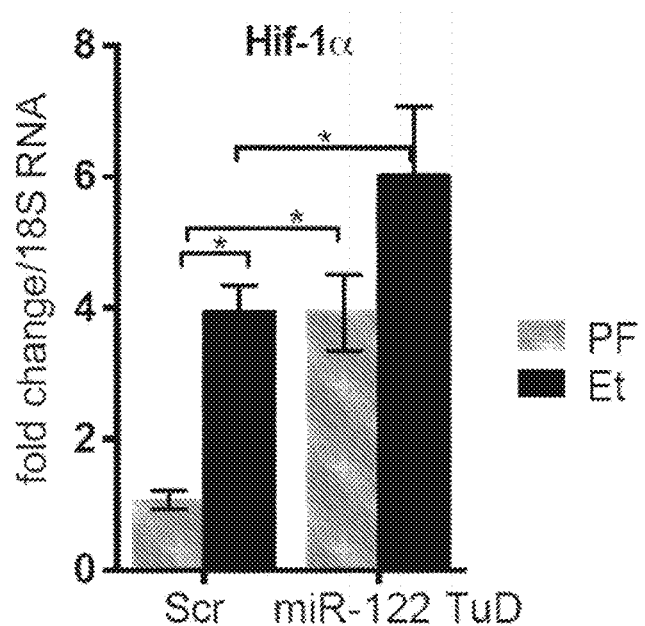
Figure 2D:
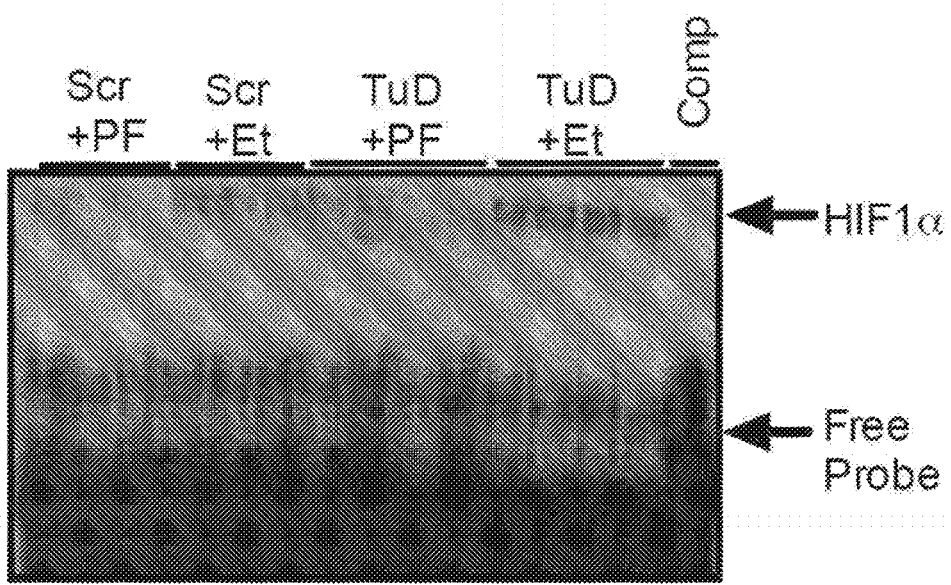
Figure 2E:
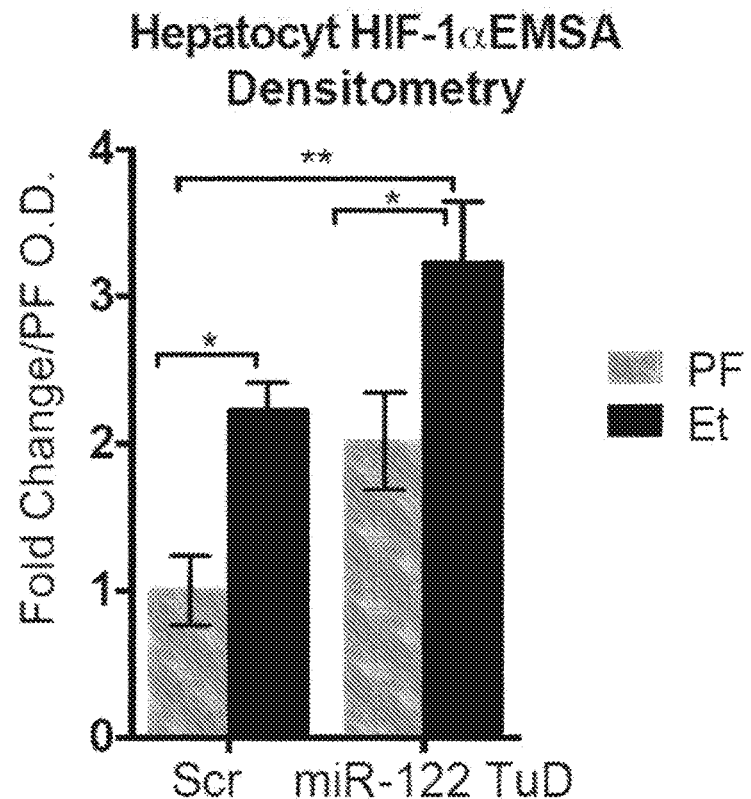
Figure 2F:
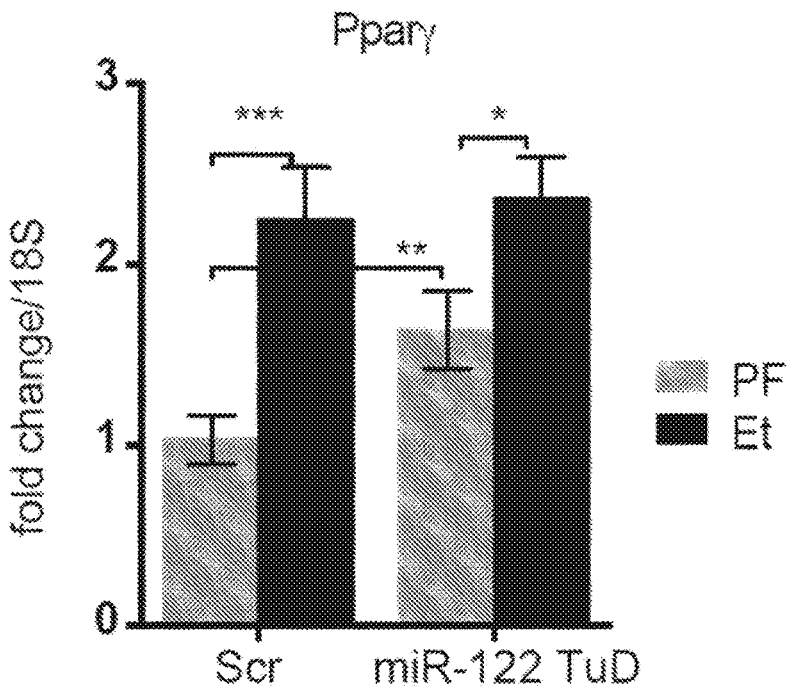

Alcohol and knockdown of miR-122 in the livers of WT mice increased HIF-1α mRNA individually and additively (FIG. 2D). To confirm that the increase in HIF-1α mRNA represents increased transcriptional activity, an EMSA using a HIF-1α consensus binding oligonucleotide was performed on hepatocyte nuclear extracts. Results indicate that TuD-mediated inhibition of miR-122 resulted in increased HIF-1α DNA binding at baseline, equivalent to alcohol-feeding alone (FIG. 2D). Furthermore, the combination of alcohol and miR-122-TuD-inhibition yielded in a synergistic increase of HIF-1α mRNA (FIG. 2D) and DNA-binding activity suggesting that alcohol directly and via miR-122 regulates HIF-1a (FIG. 2D). HIf-1α has numerous target genes and of those PPARγ is important in affecting liver steatosis. Indeed, it was found that the increase in HIF-1α activity also translated to an increase in PPARγ expression (FIG. 2E), a direct target of HIF-1α activation and a key factor in driving steatosis.

Hepatocyte-Specific Knockout of HIF-1α Protects from Liver Injury, Steatosis, Inflammation, and Fibrosis Induced by Alcohol or miR-122 Reduction Based on the discovery that miR-122 is decreased by alcohol and that miR-122 inhibits HIF-1α in hepatocytes, the ability of miR-122 to regulate HIF-1α in vivo was investigated. It was examined whether mice with a hepatocyte-specific knockout of HIF-1α (HIF1α$^{hep-/-}$) are protected from the miR-122-TuD and/or alcohol-induced liver injury.

Figure 3A:
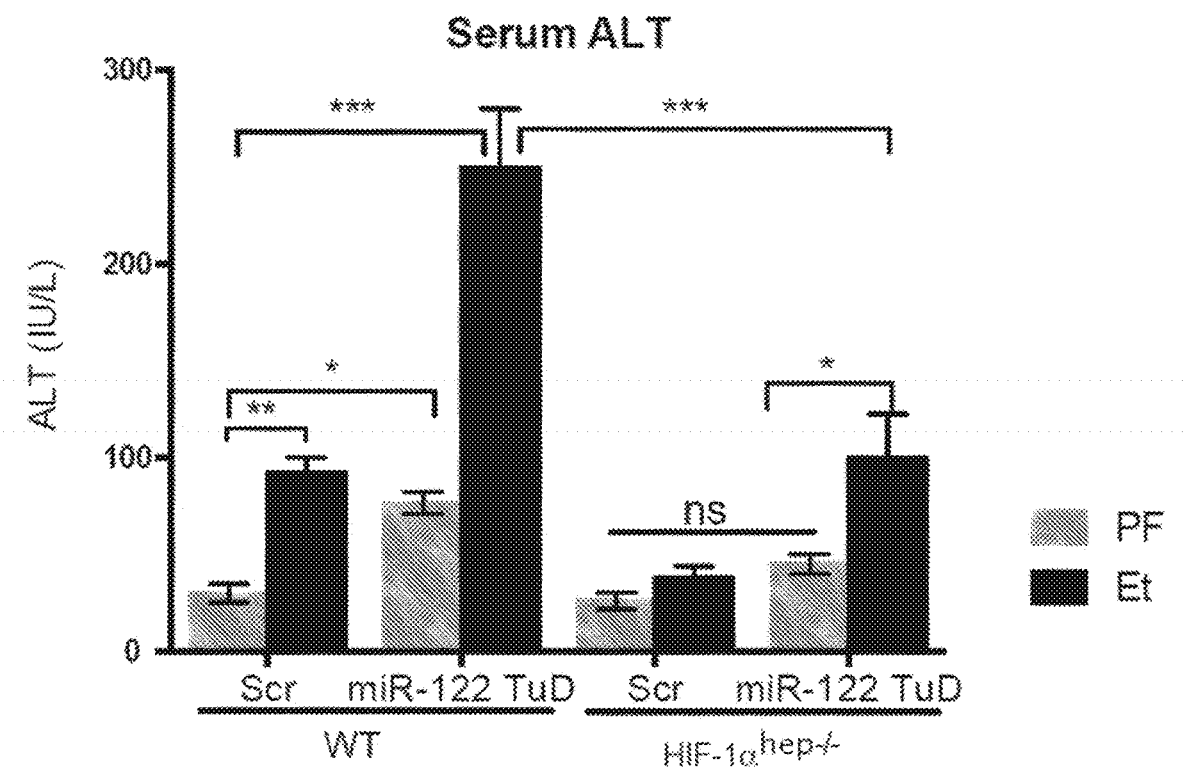
FIGS. 3A-3E show miR-122 mediates HIF-1α steatosis and liver injury through HIF-1α in vivo assessment of (FIG. 3B) H&E histology, (FIG. 3C) steatosis score, (FIG. 3D) triglyceride concentrations, (FIG. 3E) PPARγ and (FIG. 3A) serum ALT levels, in WT or HIF-1α$^{hep-/-}$ mice. *P<0.05, P<0.005, *P<0.0005 by Student's t test or two-way ANOVA (n=6-14). Scale bars; 100 μm.

It was found that in contrast to WT mice, HIF1α$^{hep-/-}$ mice were protected from liver injury (FIG. 3A) and steatosis (FIGS. 3B-3D) whether induced by alcohol or miR-122 inhibition alone, and their combination. Furthermore, HIF1α$^{hep-/-}$ also displayed no increase in PPARγ (FIG. 3E) associated with the knockdown of miR-122 and alcohol in WT mice. These data suggested first, that the loss of miR-122 in hepatocytes directly triggers an increase of HIF-1α, resulting in steatosis and hepatocyte injury in the liver. Second, alcohol and exogenous miR-122 inhibition synergistically decrease in miR-122 and induce HIF-1α, and subsequently PPARγ.

Analysis of H&E sections and qPCR evaluation of immune cell markers revealed increased macrophage infiltration, CD68 and F4/80 (FIG. 3B, FIG. 4A, FIGS. 10C-10D) in anti-miR-122 TuD-treated, or alcohol-fed mice with an even greater increase in mice treated with both TuD and alcohol. Increased levels of IL-1ß and MCP-1 protein (FIG. 4A, FIGS. 10E-10F) were also found in the livers of alcohol and miR-122 TuD-treated mice. HIF1α$^{hep-/-}$ mice treated with either miR-122 inhibition or chronic alcohol showed a reduction in inflammatory cell infiltration and activation compared to WT mice. (FIG. 4A, FIG. 3B, FIGS. 10C-10F), indicating that in addition to steatosis, liver inflammation induced by miR-122 decrease is also attenuated by hepatocyte-specific HIF-1α deficiency.

Figure 3B:
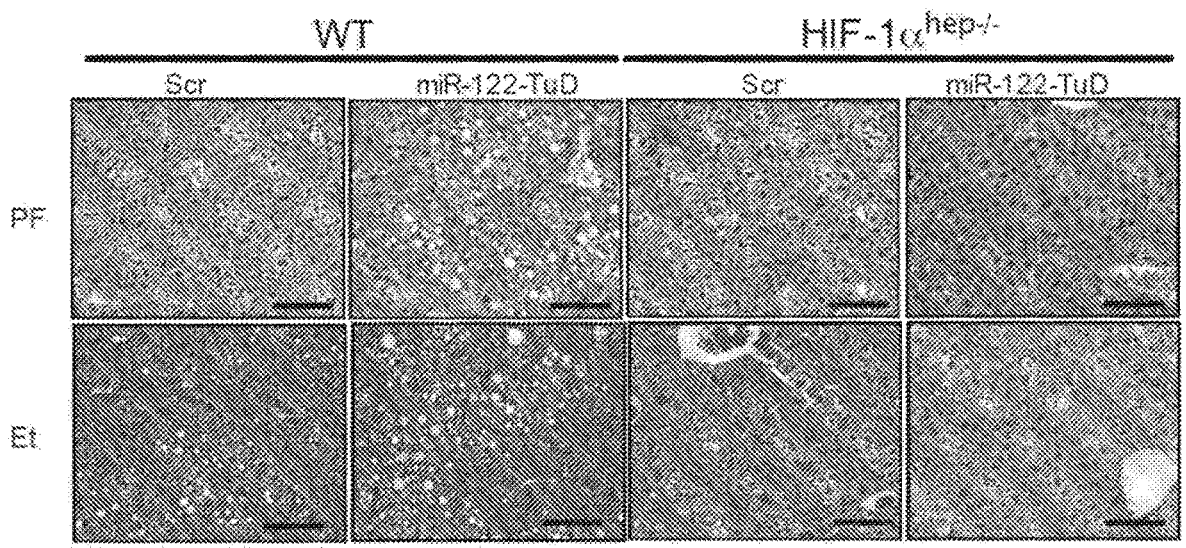
Figure 3C:
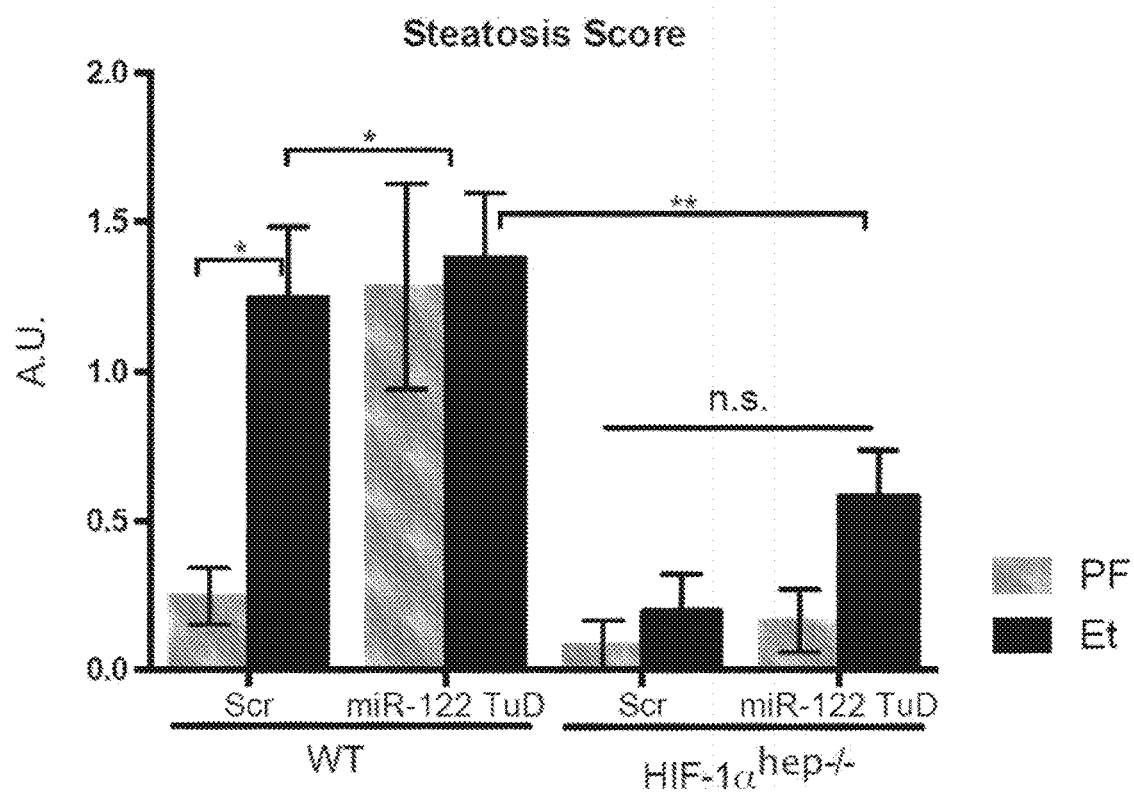
Figure 3D:
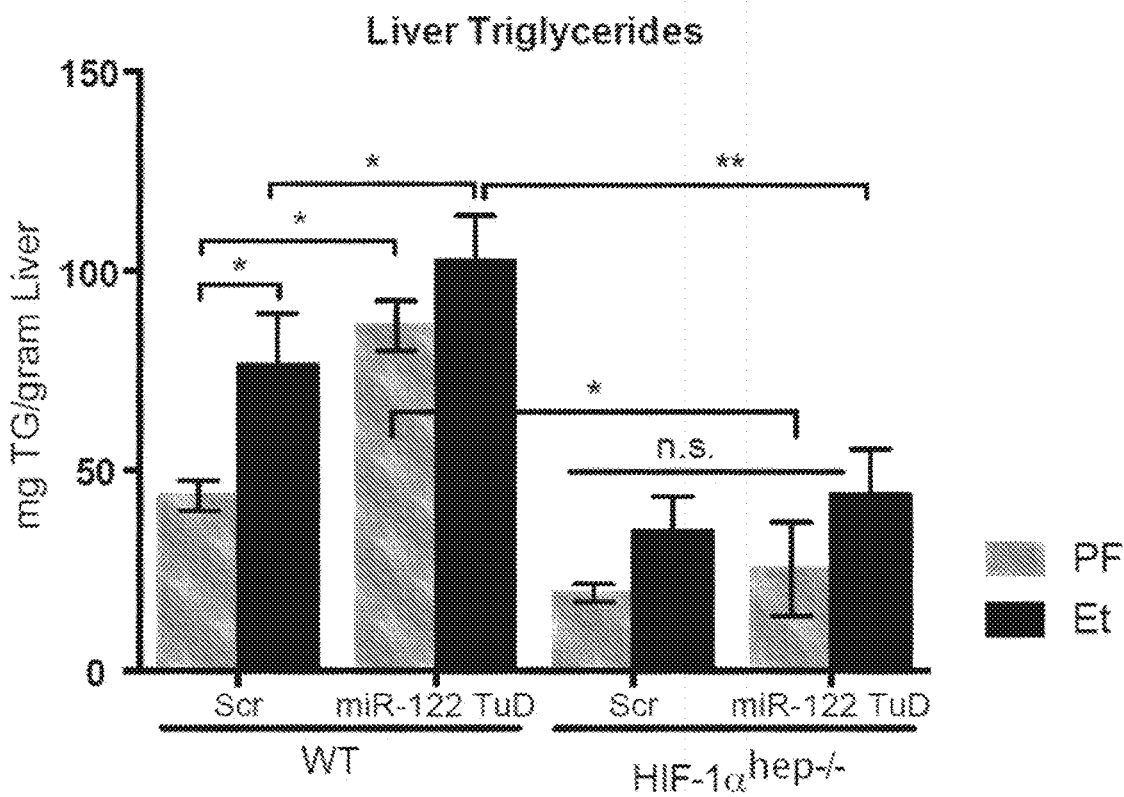
Figure 3E:
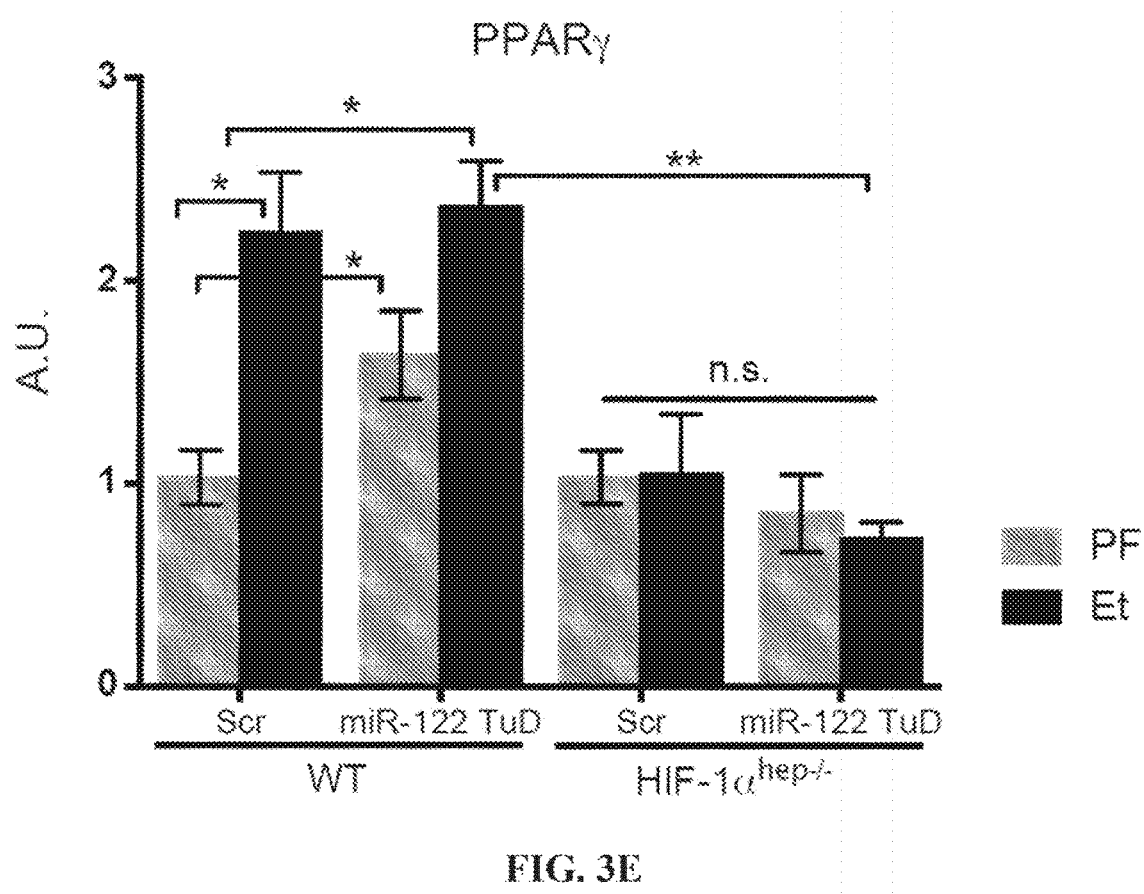
Figure 4A:
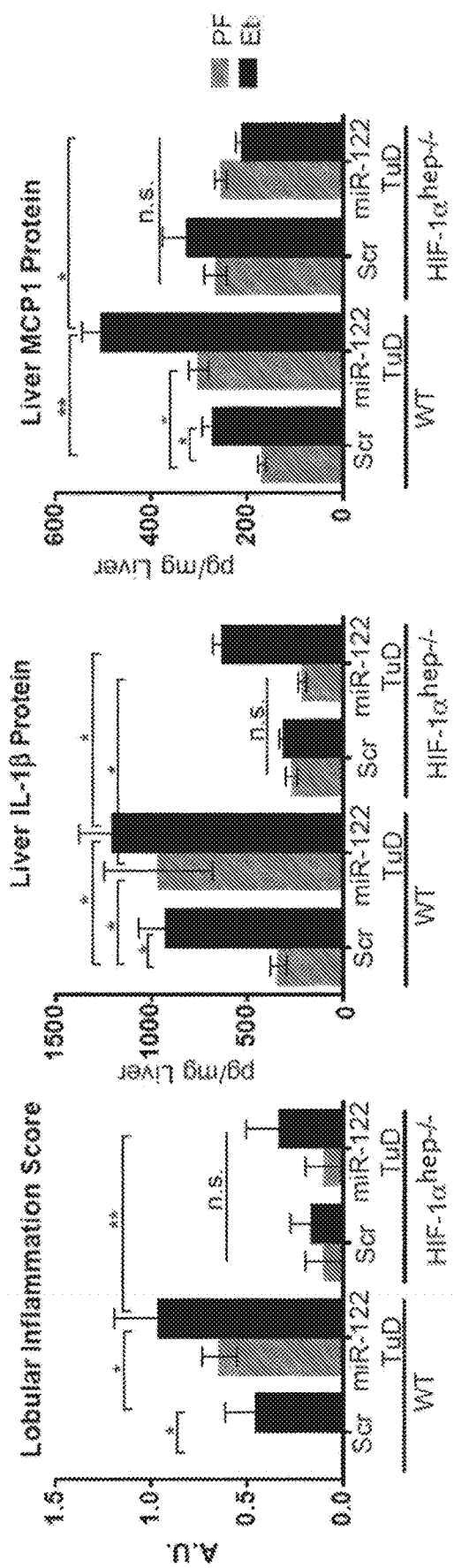
FIGS. 4A-4C show miR-122 loss mediates hepatic inflammation and fibrosis through HIF-1α. Assessment of hepatic inflammation by (FIG. 4A) scoring of inflammatory cell infiltration, liver IL-1ß and MCP-1 protein from total liver lysates. Histological assessment of fibrosis by Sirius Red (FIG. 4B) staining.
Figure 4B:
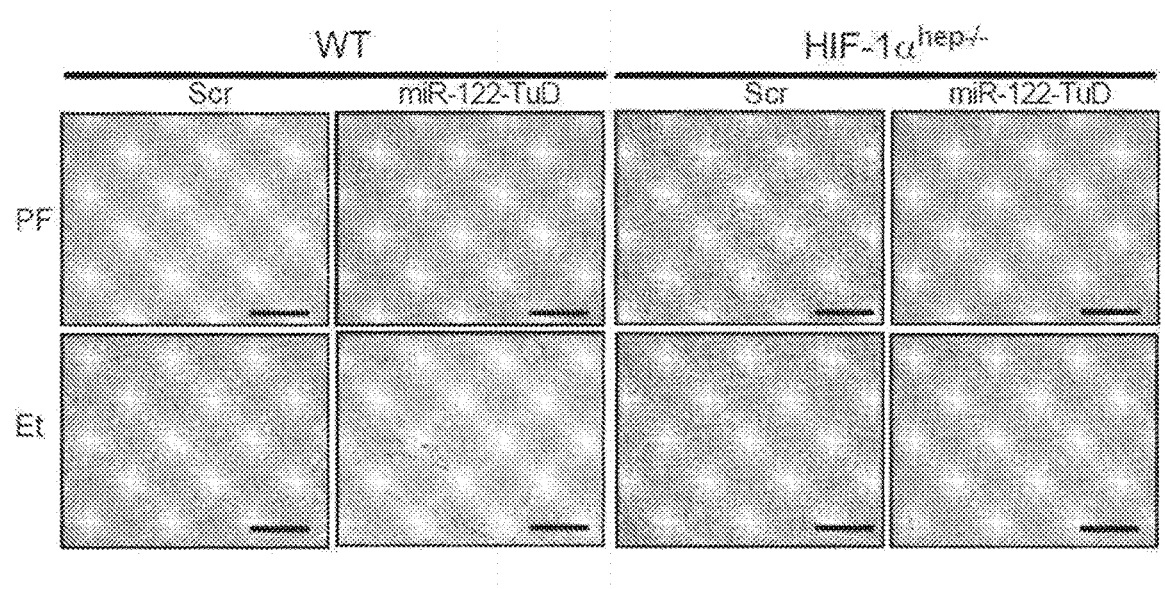
Figure 4C:
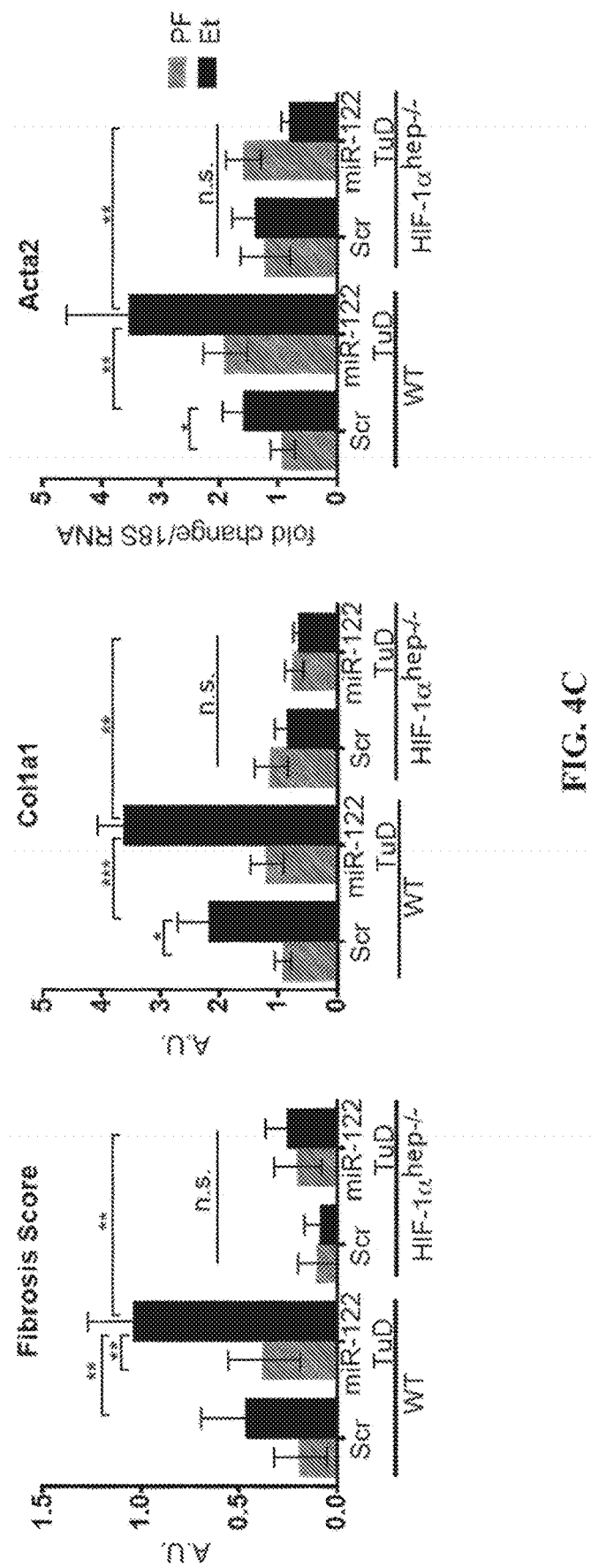

The development of fibrosis indicates progression of ALD as a result of sustained hepatocyte injury, inflammation, and stellate cell activation. Increases in fibrosis markers were found after alcohol feeding indicated by Sirius Red staining (FIG. 4B) and expression of pro-collagen-1α and Acta2 (FIG. 4C). Furthermore, the highest expression of pro-collagen-1α and Acta2 (FIG. 4C) expression, and Sirius Red staining was found in miR-122 TuD mice treated with alcohol, compared to pair-fed controls (FIG. 3B). The increase in fibrosis in the miR-122 TuD+Et group was abrogated in the HIF1α$^{hep-/-}$ mice (FIGS. 3B-3C). Together, these data indicate that the increased pro-inflammatory and pro-fibrotic state are secondary to HIF-1α-mediated hepatocyte injury due to the reduction of miR-122.

Figure 11A:
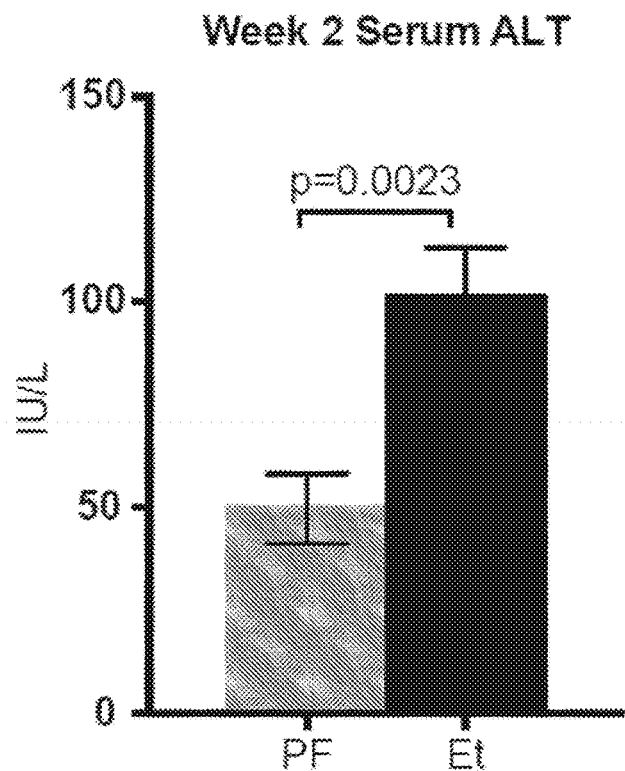
FIGS. 11A-11F shows (FIG. 11A) Serum ALT from week 2, of a Liber DeCarli chronic alcohol feeding model.
Figure 11B:
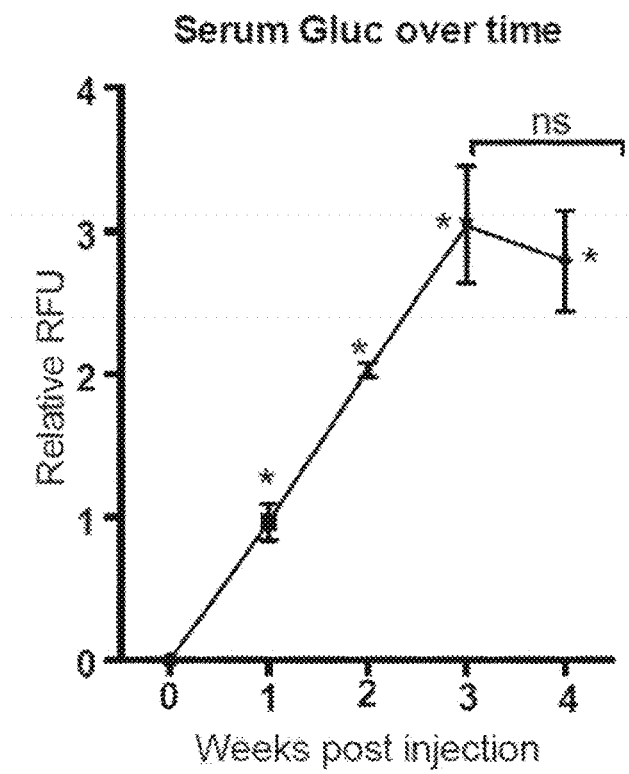
Figure 11C:
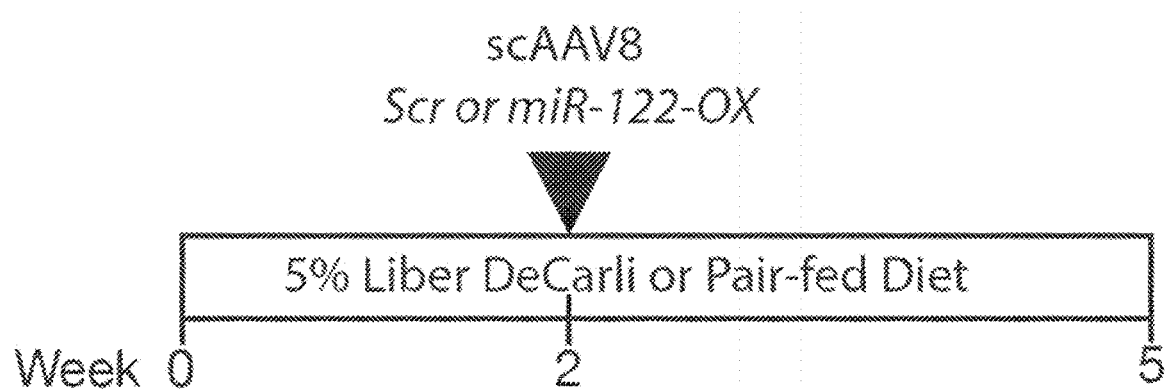
Figure 11D:
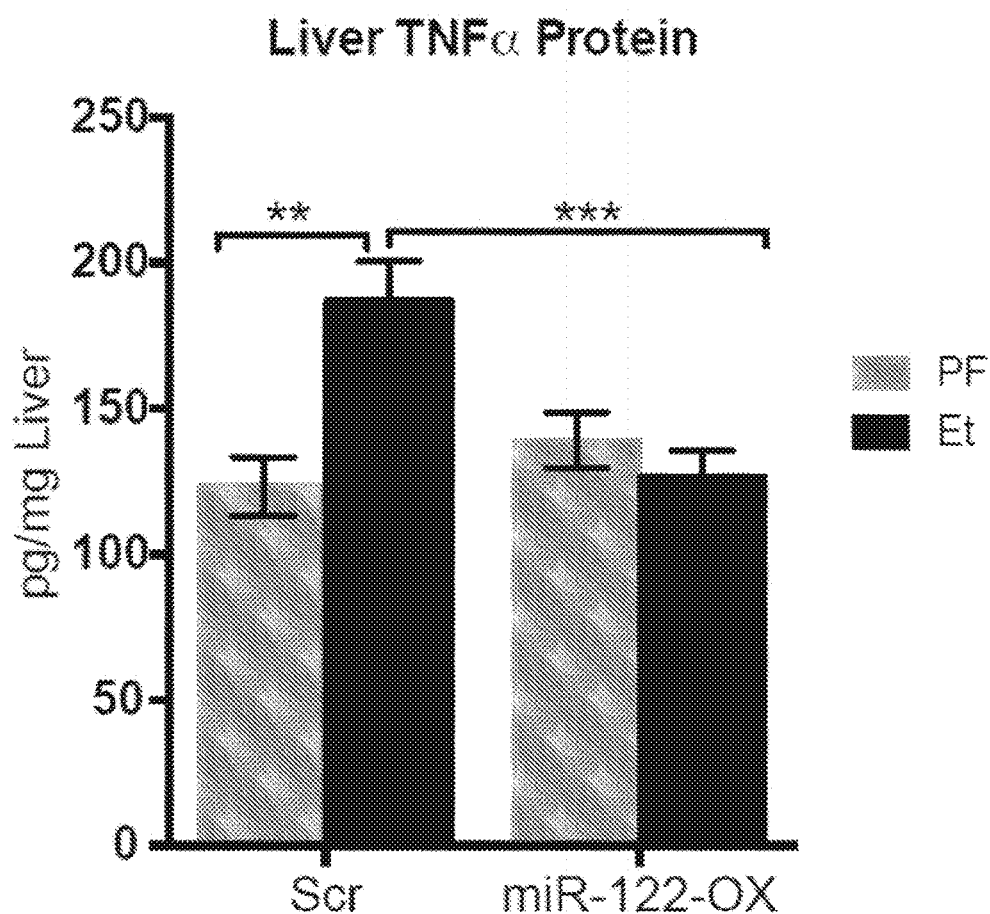
Figure 11E:
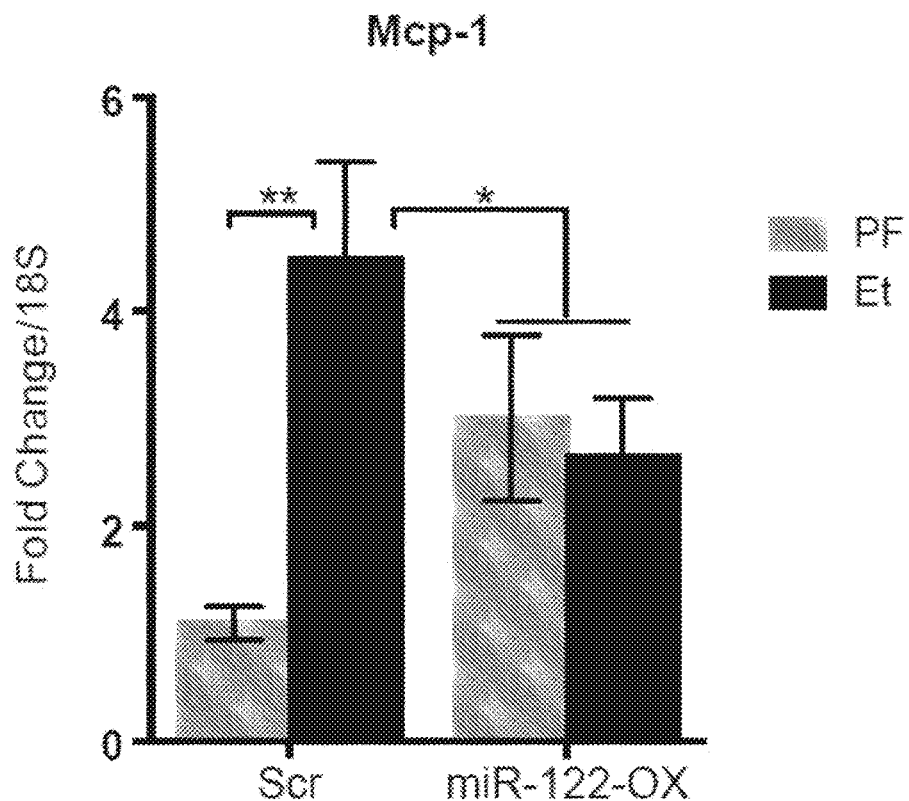
Figure 11F:
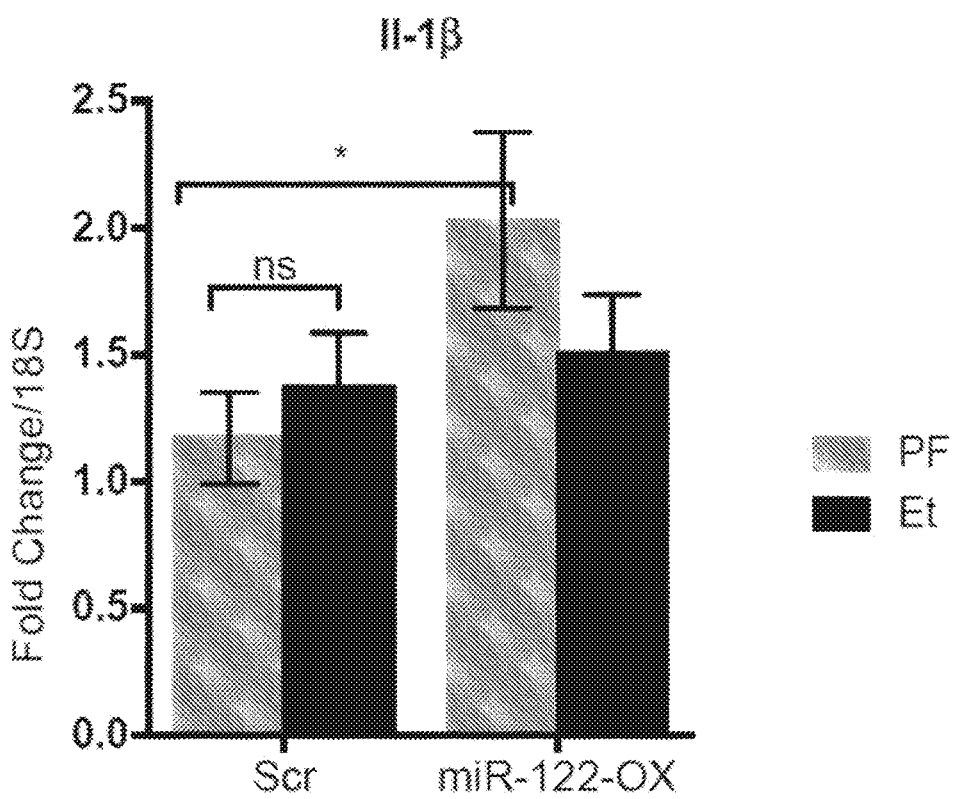

Therapeutic Restoration of miR-122 in Hepatocytes rescues Mice from Alcohol-Induced Liver Injury In Vivo To assess the therapeutic potential of miR-122 restoration on the pathogenesis of alcoholic liver disease, an scAAV8 vector expressing miR-122 (miR-122-OX) and a scrambled (scr) were produced. In a preliminary experiment, it was established that wild-type alcohol-fed mice develop significant liver injury by week 2 of the 5-week alcohol feeding (FIG. 11A). It was also determined that scAAV8 miR-122-OX construct requires 3 weeks for full expression in the liver (FIG. 11B). Therefore, pair-fed and alcohol-fed mice were treated with 6×10$^{11}$ viral particles containing Scr or miR-122-OX construct via tail-vein injection on week 2 of a 5-week alcohol feeding model (FIG. 11C).

Figure 5A:
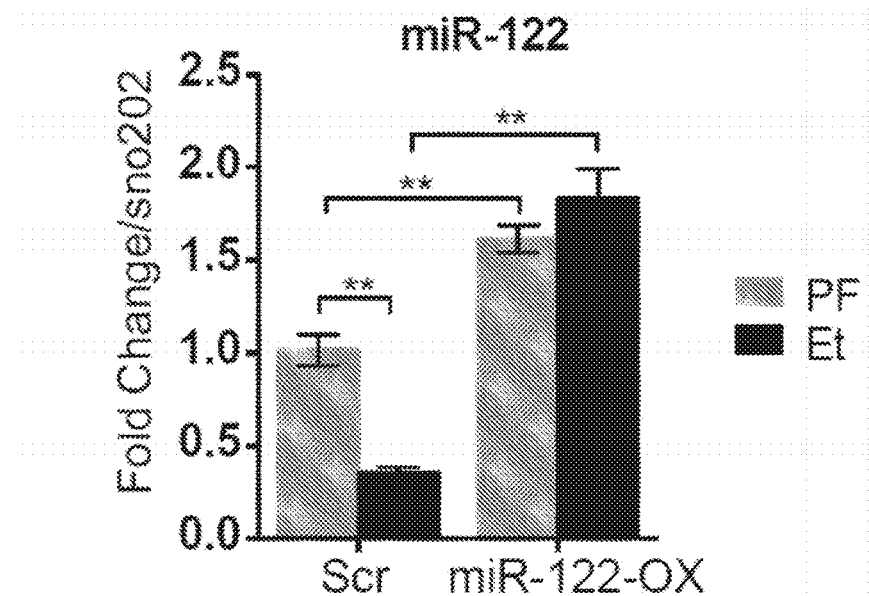
FIGS. 5A-5E show treatment with scAAV8-miR-122-OX protects from ALD via inhibition of HIF-1α expression.
Figure 5B:
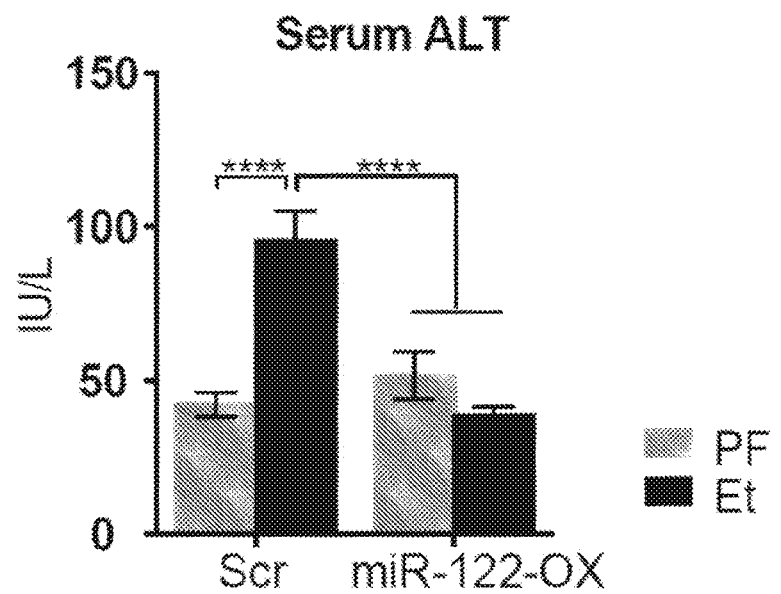
Figure 5C:
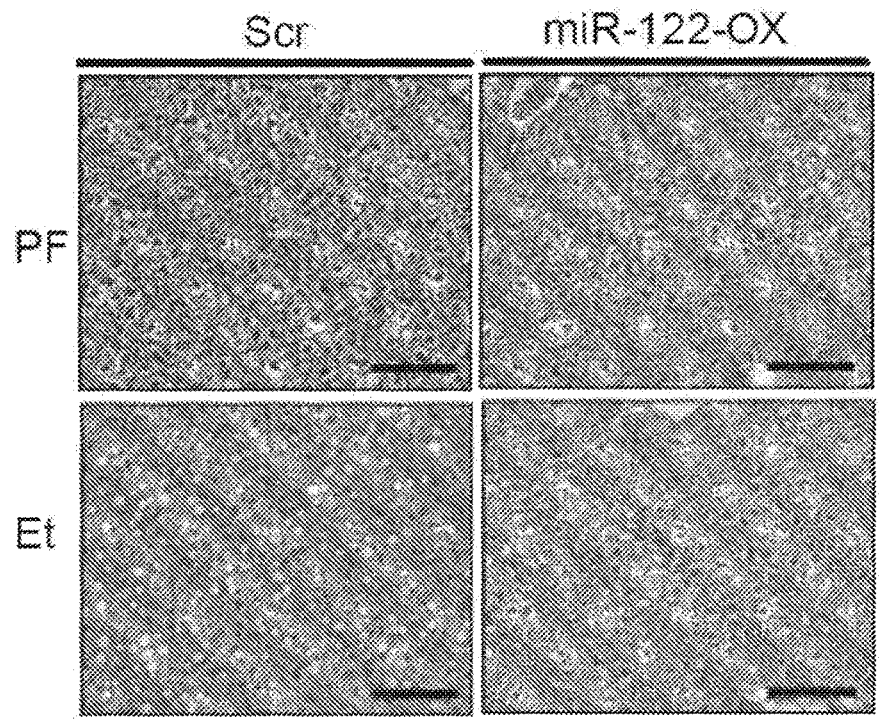
Figure 5C:
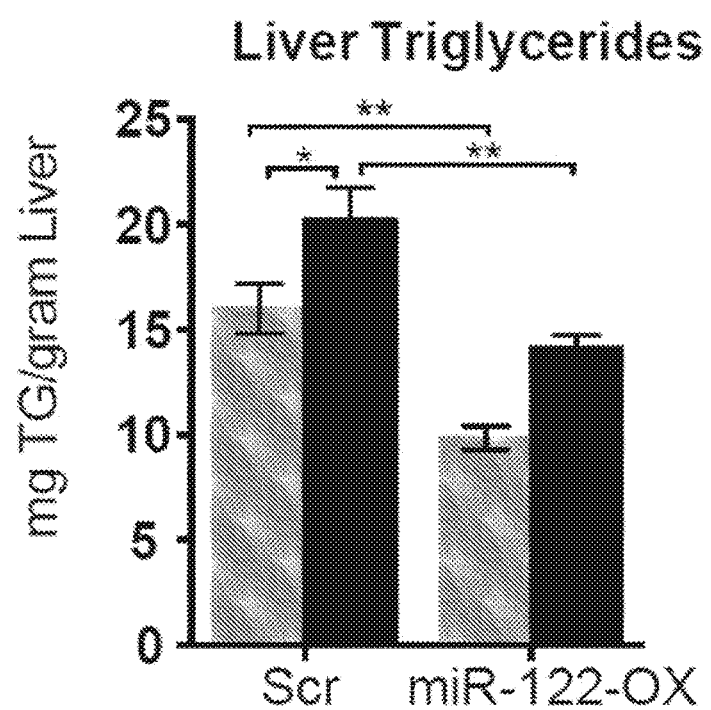
Figure 5D:
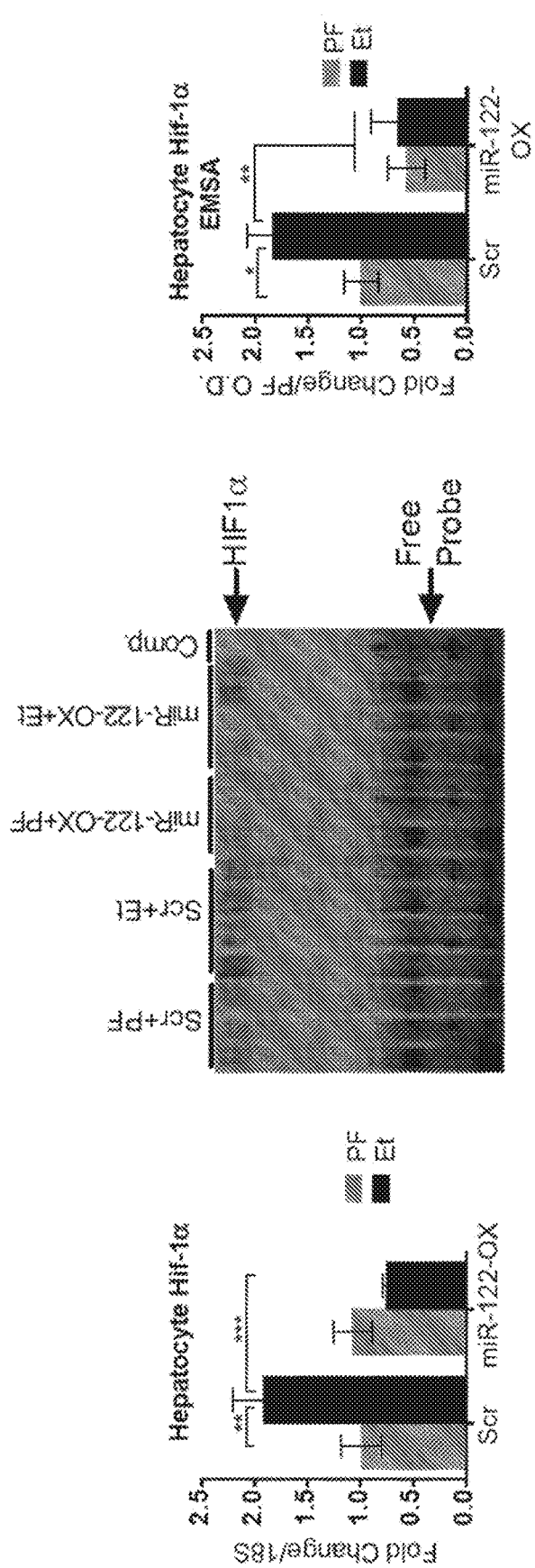
Figure 5E:
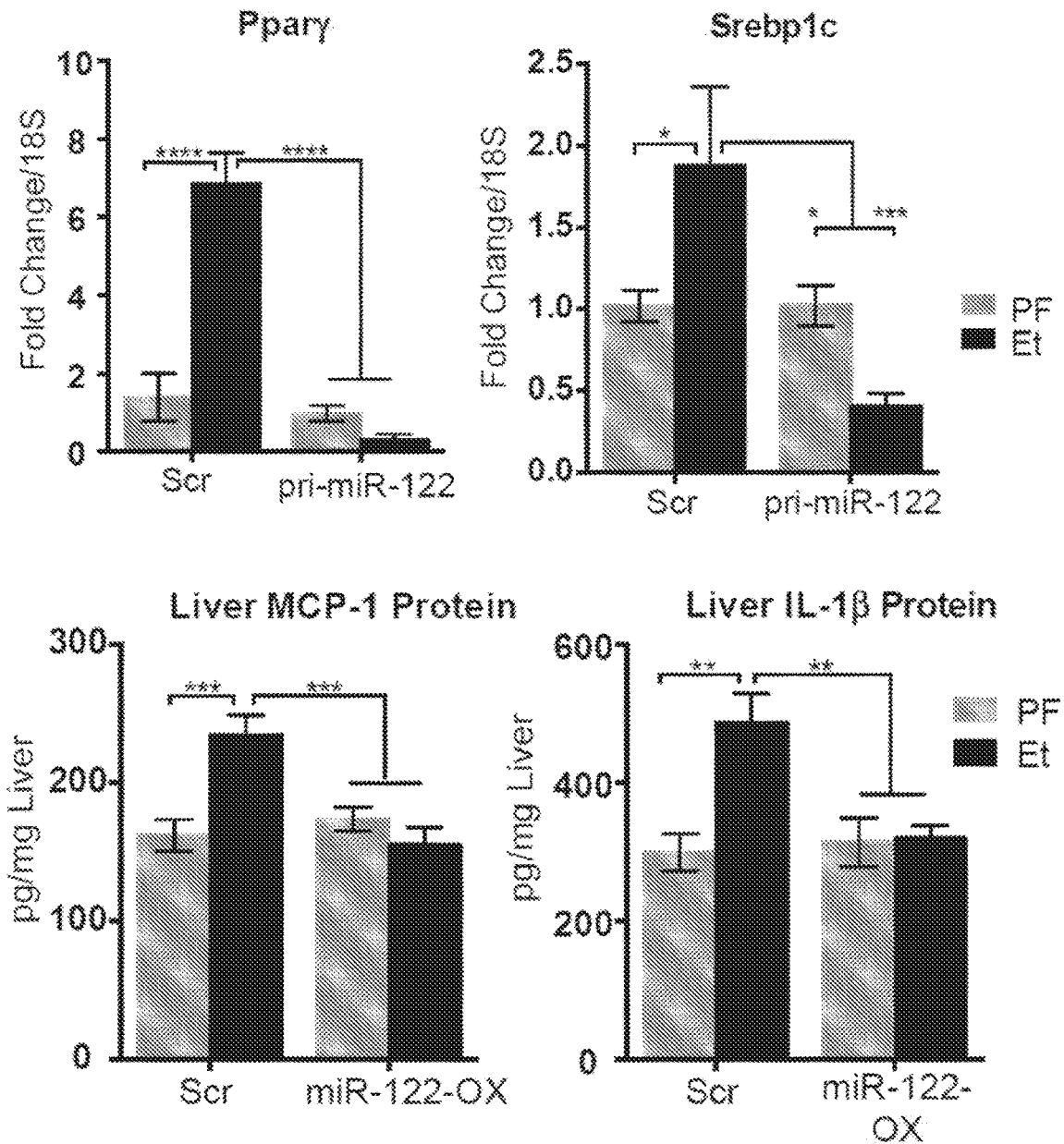

Treatment with the scAAV8-miR-122-OX effectively increased mature miR-122 levels in the livers of pair-fed and alcohol-treated mice (FIG. 5A). Overexpression of miR-122 in hepatocytes resulted in dramatic reductions in alcohol-induced increases in serum ALT (FIG. 5B), and steatosis indicated by histology and liver triglyceride levels (FIG. 5C). Consistent with in vitro data (FIG. 9A-9B), in vivo restoration of miR-122 in hepatocytes prevented the alcohol-induced increase in HIF-1α mRNA, DNA binding activity, and the HIF-1α target gene driving lipogenesis, PPARγ (FIGS. 5D-5E). Furthermore, miR-122-OX treatment prevented induction of inflammatory cytokines in ALD including MCP1 and IL-1ß at the protein (FIG. 5E) and mRNA levels (FIGS. 5D-5F). Overall, these data demonstrate that restoration of miR-122 in hepatocytes can suppress the pathogenic features of ALD via inhibition of HIF-1α in vivo and indicates that hepatocyte-specific miR-122 delivery could be a therapeutic consideration in ALD.

Figure 10B:
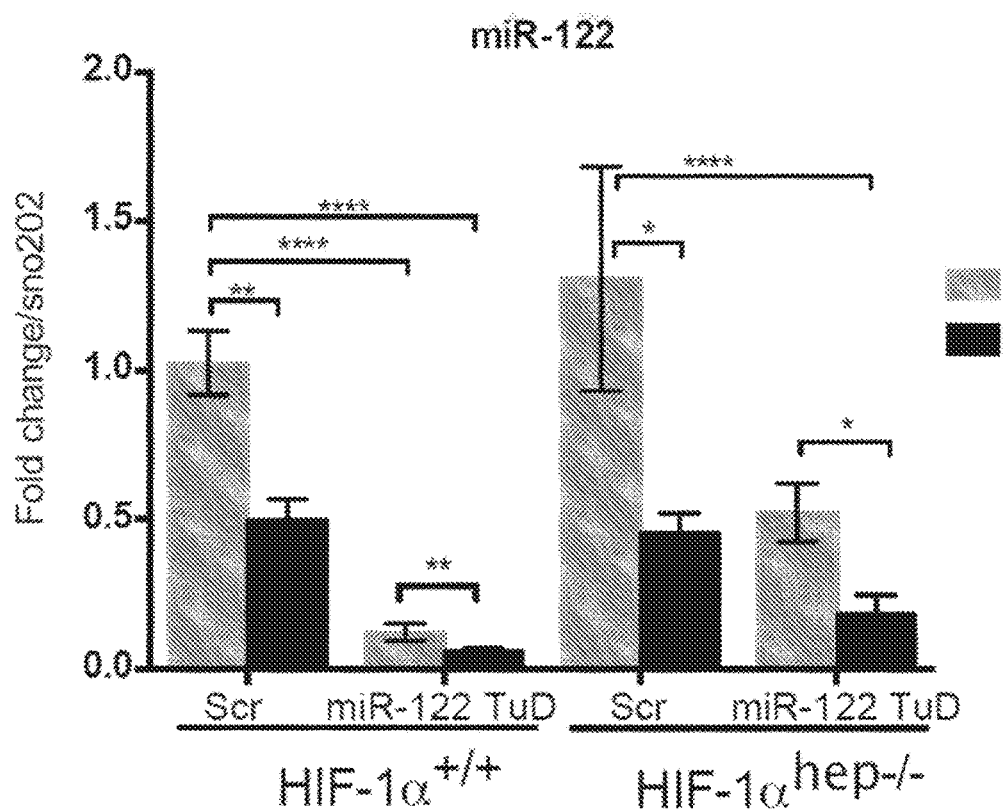
Figure 10C:
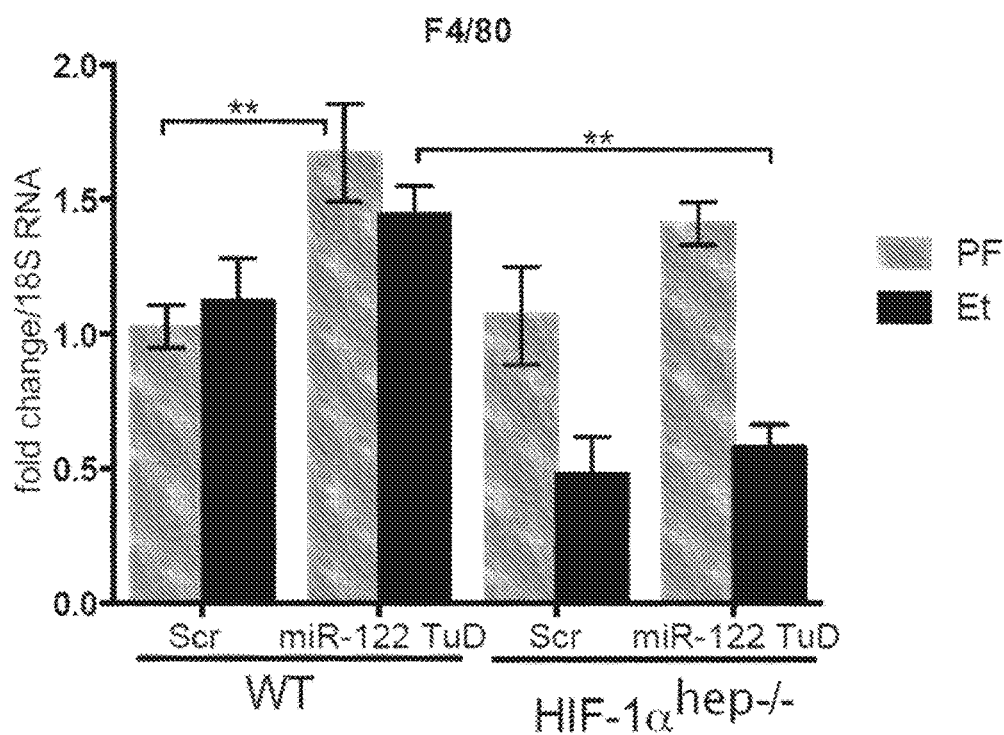
Figure 10D:
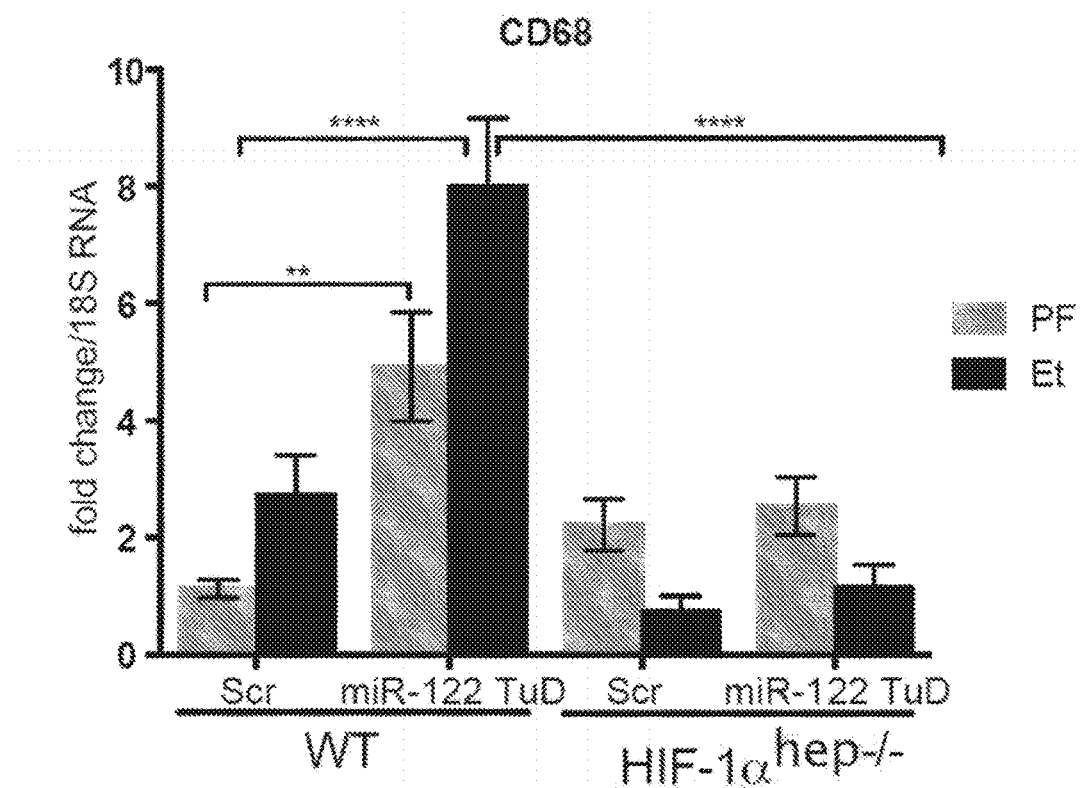
Figure 10E:
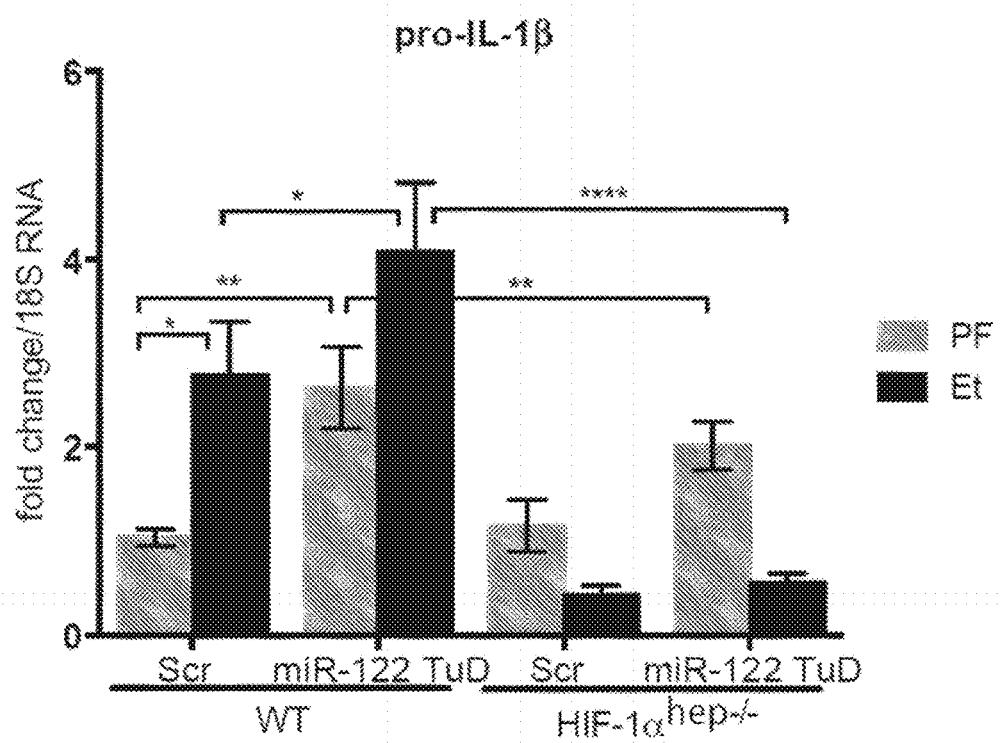
Figure 10F:
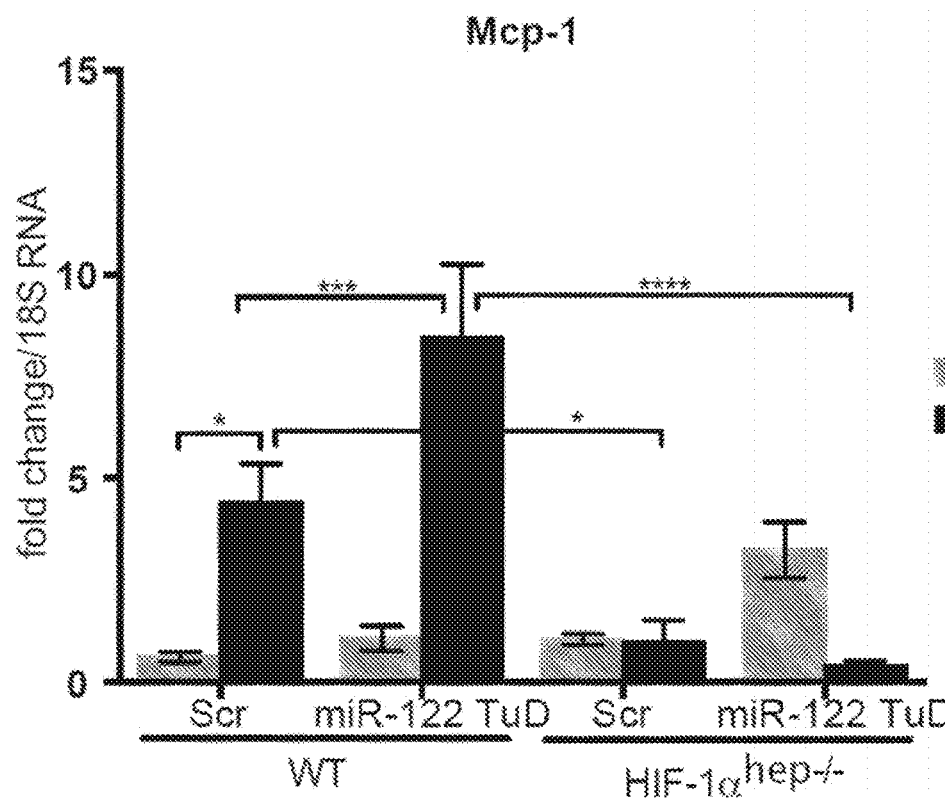
Figure 10G:
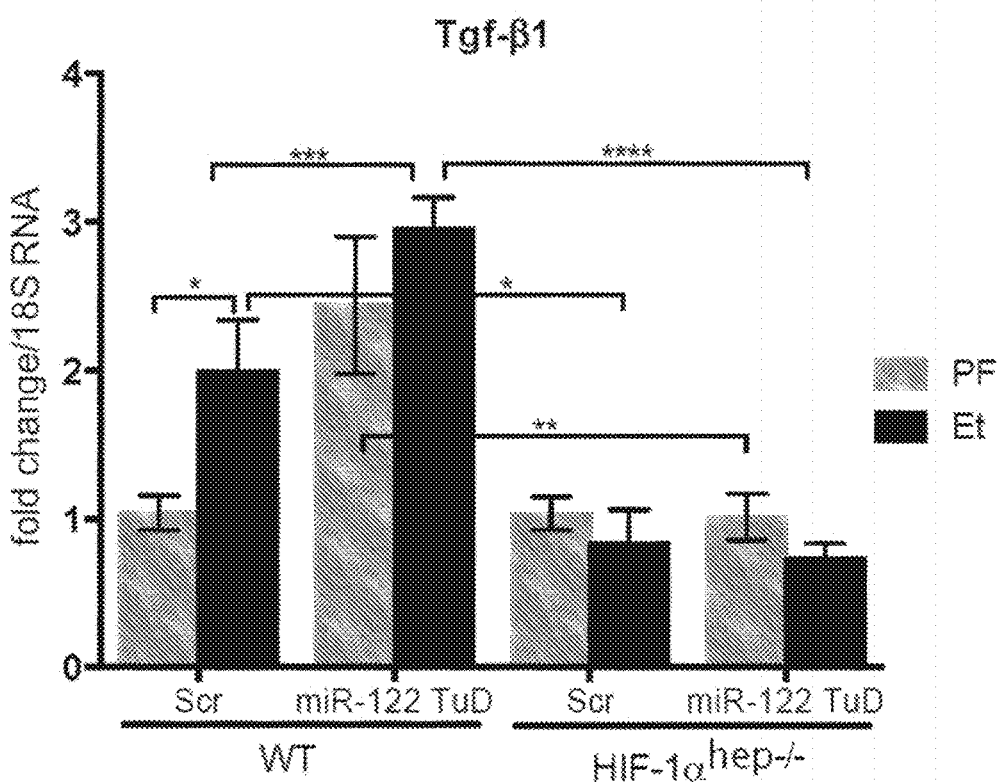

Alcohol inhibits miR-122 Transcription via Alternate Splicing of Grainyhead-Like 2 Transcription Factor MicroRNAs are encoded by their own genes and regulated transcriptionally. Surprisingly, both PF and Et mice treated with scAAV8-miR-122-OX achieved similar expression levels of mature miR-122 (FIG. 5A). It was observed that alcohol administration could reduce miR-122 levels beyond the reduction achieved by the miR-122TuD in WT and HIF1α$^{hep-/-}$ mice (FIG. 10B). Utilizing TaqMan probes specific for the endogenous miR-122 primary transcript (pri-miR-122), it was found that alcohol reduces pri-miR-122 expression, not only mature miR-122, expression was decreased in livers of in human alcoholic cirrhosis patients (approximately 2-fold) while there was no change in pri-miR-122 in patients with HCV cirrhosis (FIG. 6A). Livers of alcohol-fed mice, and specifically, isolated hepatocytes also showed a significant reduction in pri-miR-122 expression (FIG. 6B) similar to the reduction of mature miR-122 (FIGS. 1A-1B) suggesting transcriptional regulation. Of note, it was found reduced pri-miR-122 expression in hepatocytes of mice treated with either miR-122-TuD, or miR-122-OX, as well as HIF1α$^{hep-/-}$ (FIG. 6C) indicating that the effect of chronic alcohol on miR-122 transcription is independent of liver injury, or mature miR-122 levels.

Figure 12A:
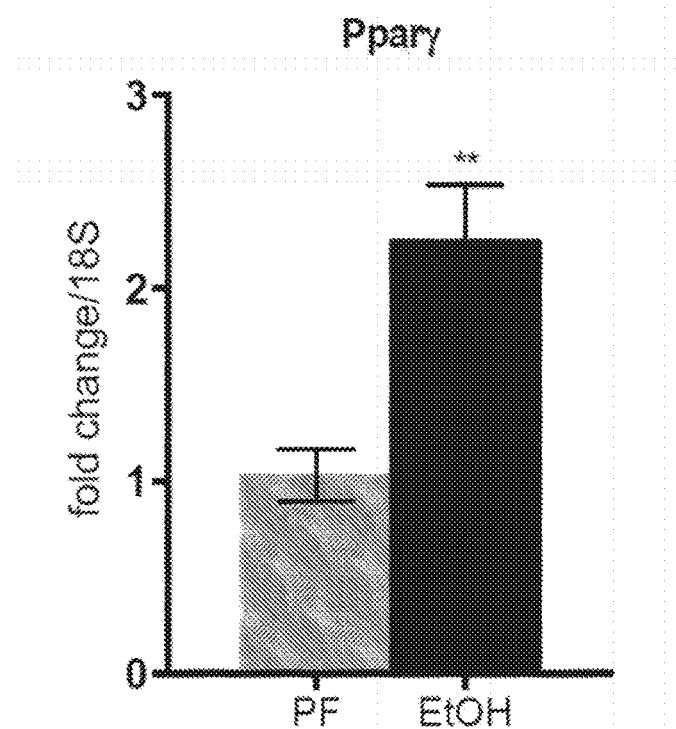
FIGS. 12A-12C show expression of (FIG. 12A) Pparγ, (FIG. 12B) HNF4α, and (FIG. 12C) HNF6 in the livers of PF and Et-fed mice.
Figure 12B:
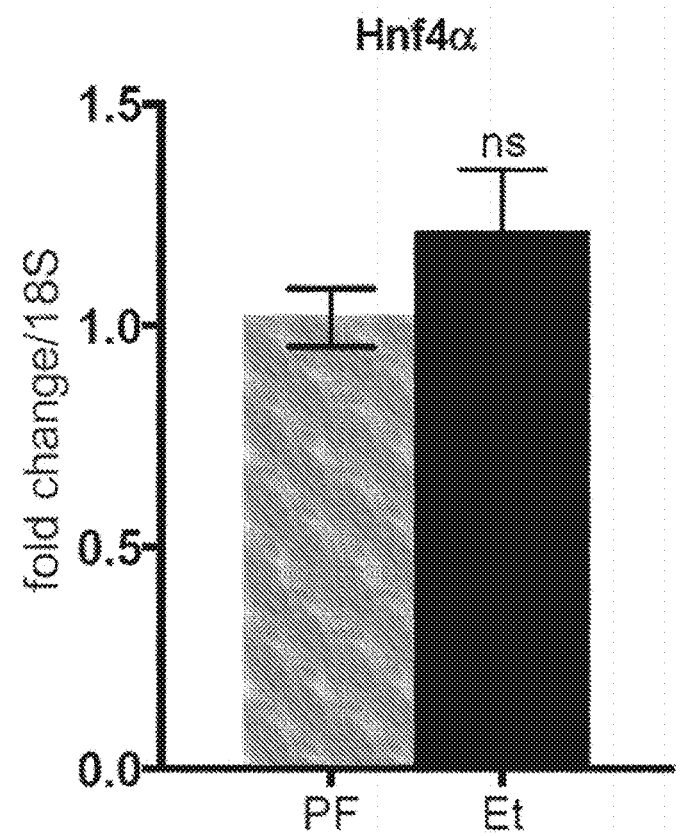
Figure 12C:
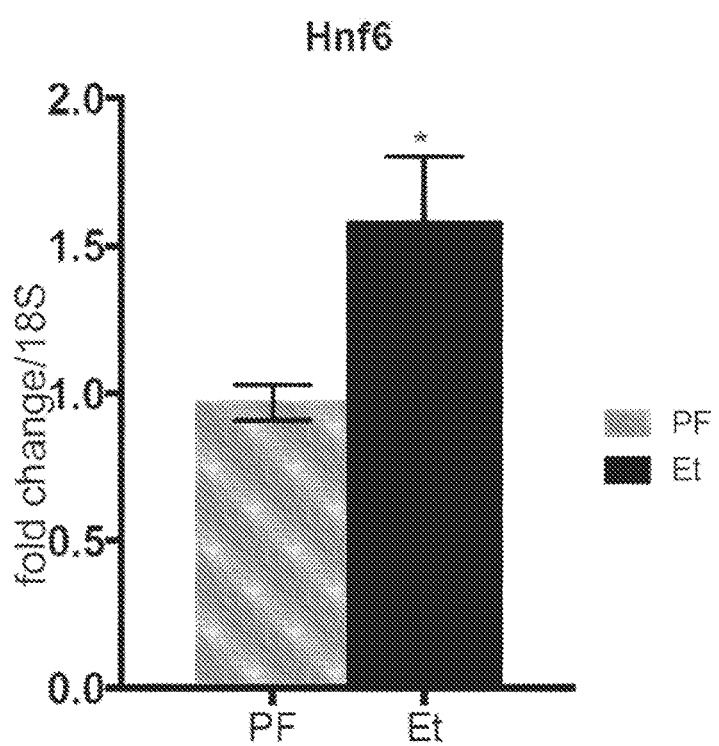

The high baseline level of miR-122 in hepatocytes is maintained by transcription factors including HNF4 and HNF6. However, data indicate that none of these transcription factors showed changes in the livers of alcohol-fed mice compared to control mice (FIGS. 12A-12C). Grainyhead like-2 (GRHL2), a homolog of the drosophila grainyhead transcriptional regulator, was investigated.

Figures 6D, 6E:
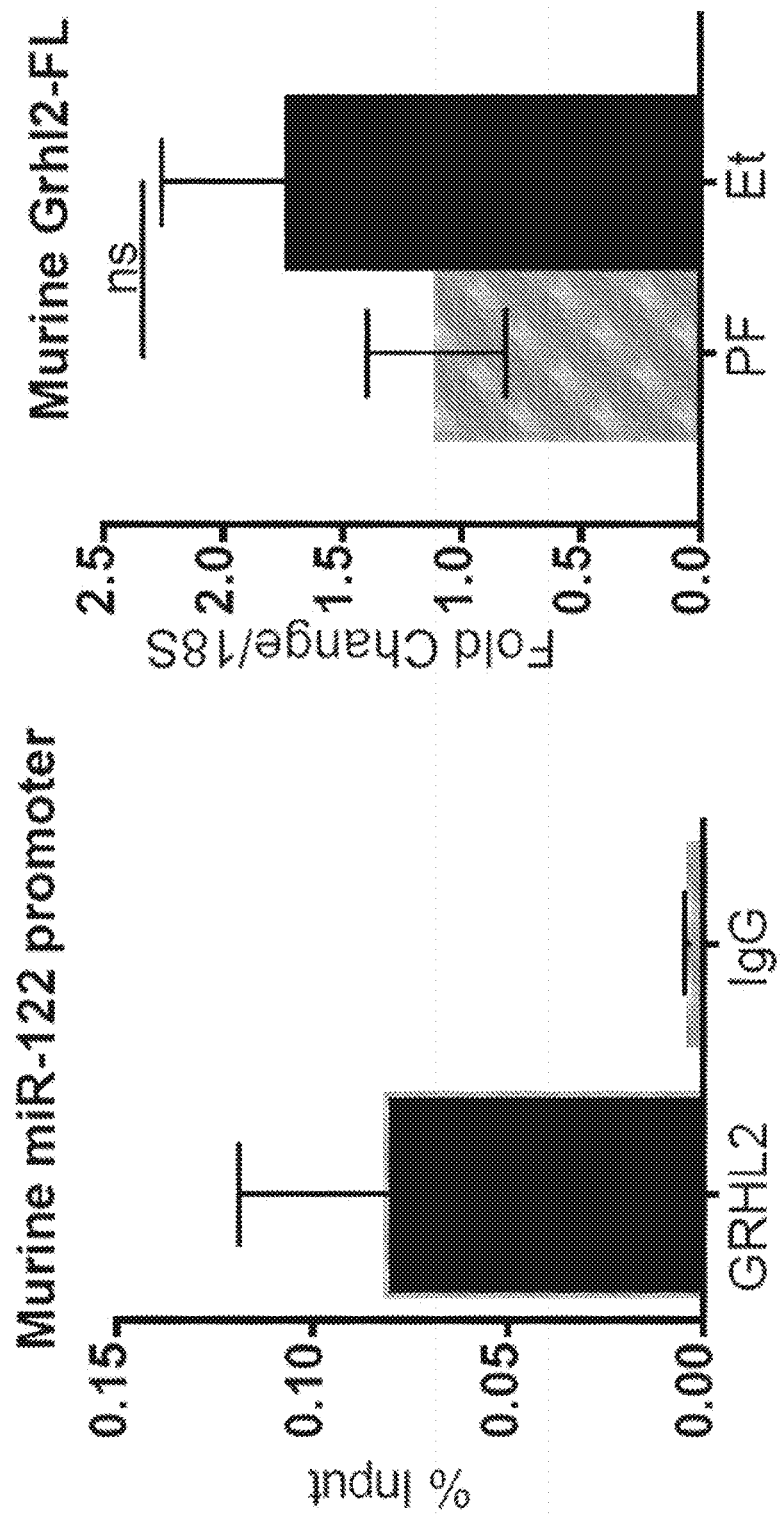
Figure 6F:
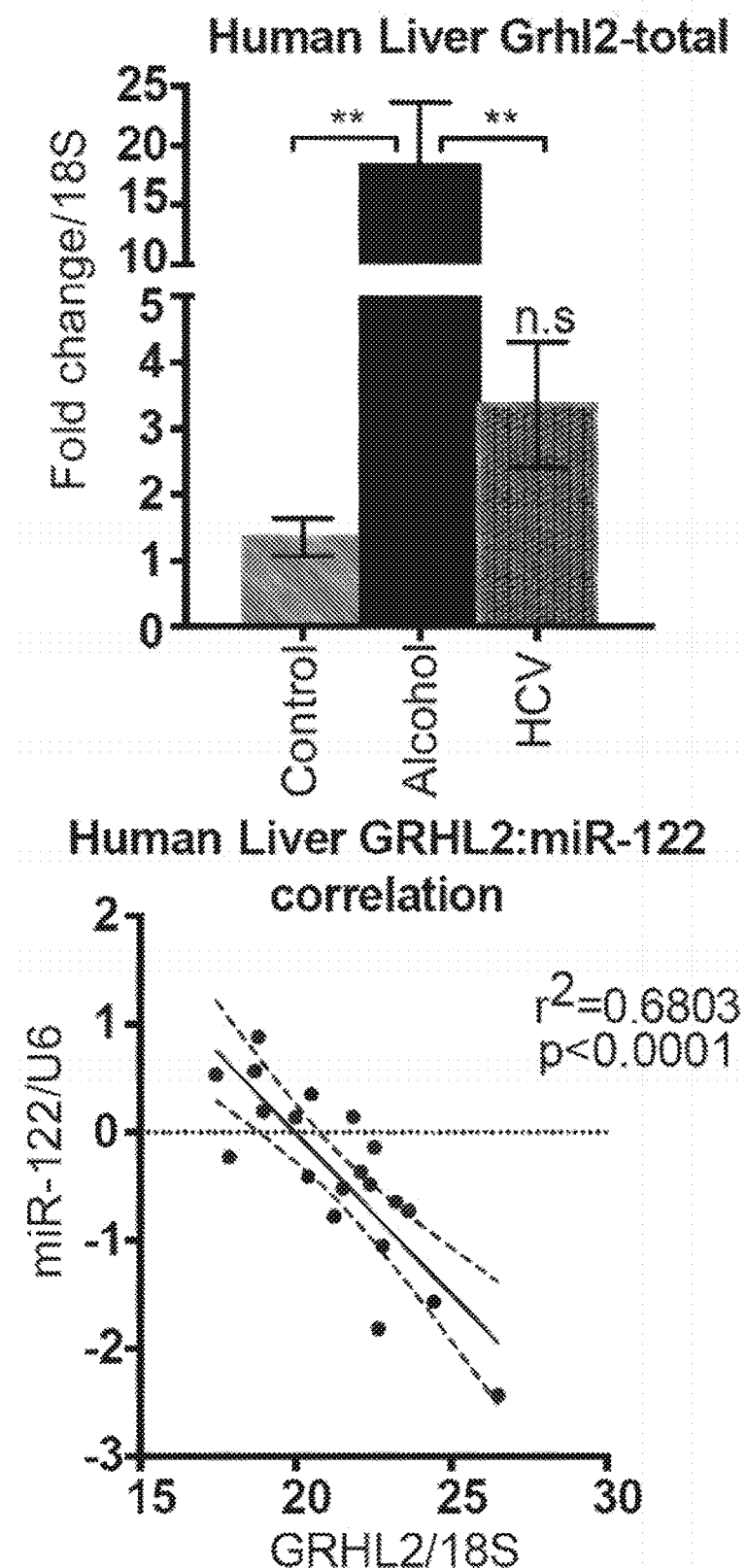

Using in silico analysis, a conserved grainyhead dimer binding site approximately 300 bps upstream of the miR-122 transcription start site (TSS) was identified, (FIG. 12D). Chromatin immunoprecipitation-qPCR was performed on HUH-7 cells and confirmed the putative GRHL binding site in the miR-122 promoter (FIG. 6D). Total liver extracts from alcohol-fed mice showed a modest, but statistically not statistically significant increase in GRHL2 mRNA expression (FIG. 6E). However, robust increases in GRHL2 expression were observed in the livers of alcoholic cirrhosis patients (FIG. 5F) when compared to healthy controls or livers with HCV cirrhosis. Furthermore, this 18-fold increase in GRHL2 demonstrated a significant inverse correlation with miR-122 expression (FIG. 6F, $r^2$=0.6803, P<0.0001) in human alcoholic cirrhotic livers.

Figure 7A:
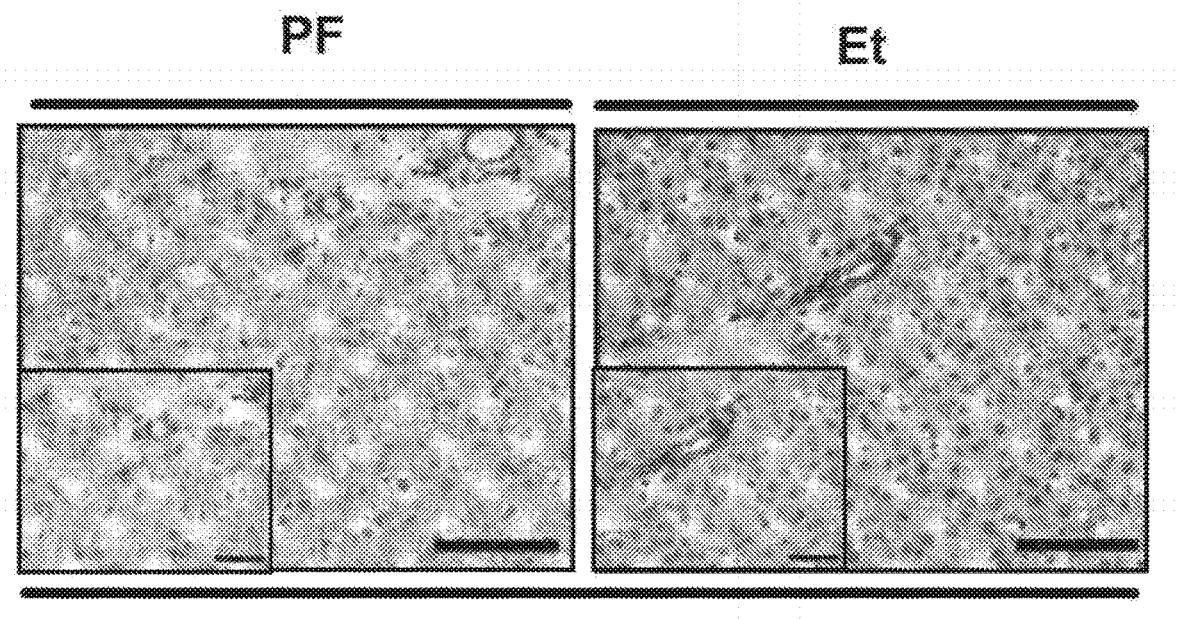
FIGS. 7A-7F show alcohol inhibits miR-122 in hepatocytes via alternatively spliced GRHL2. GRHL2 histology in (FIG. 7A) murine and (FIG. 7B) human livers. Scale bars; full-size=100 μm, inset=50 μm.
Figure 7B:
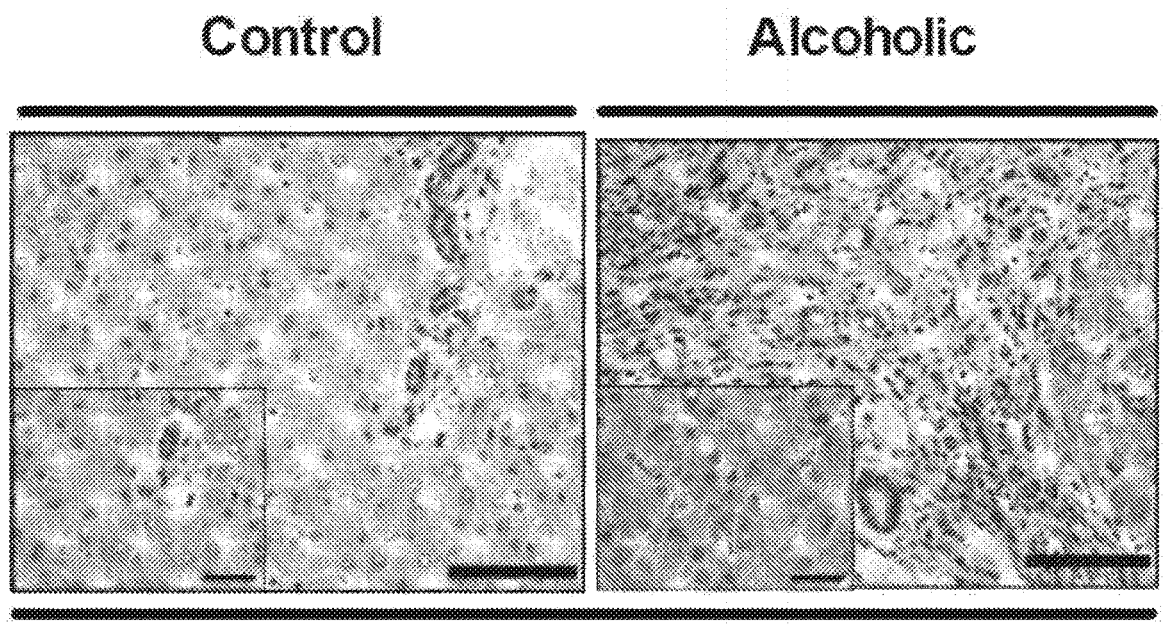
Figure 7C:
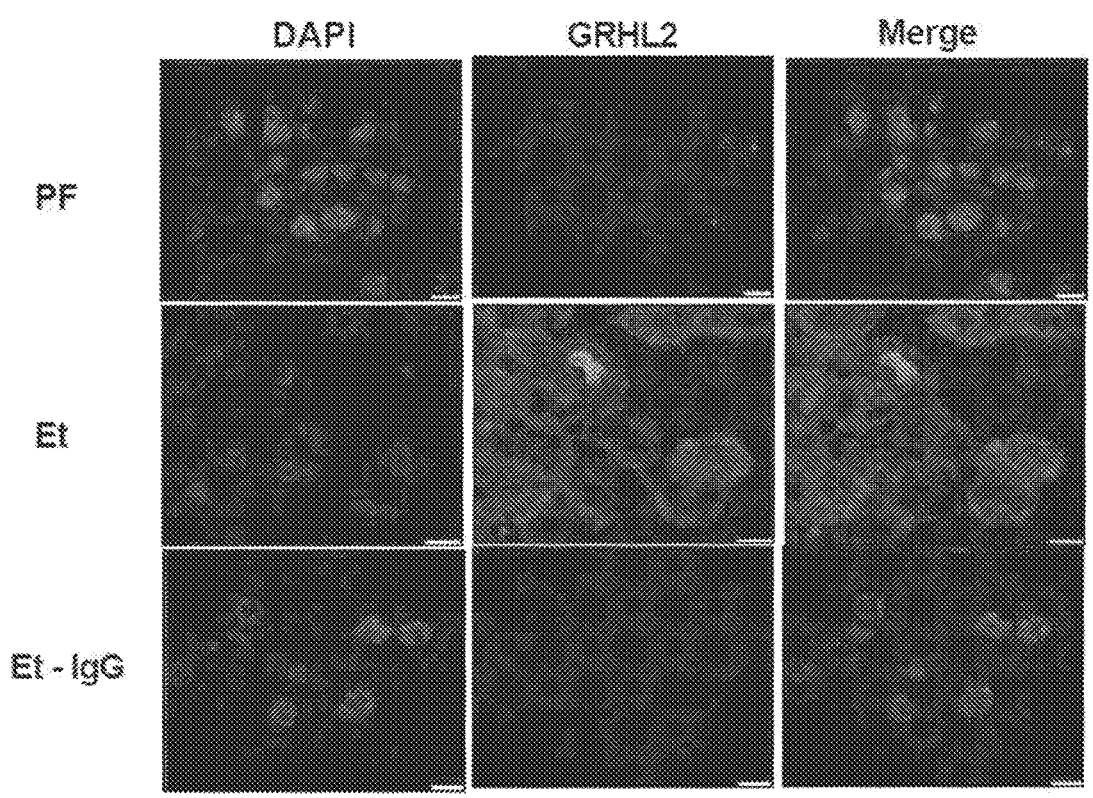
Figure 7D:
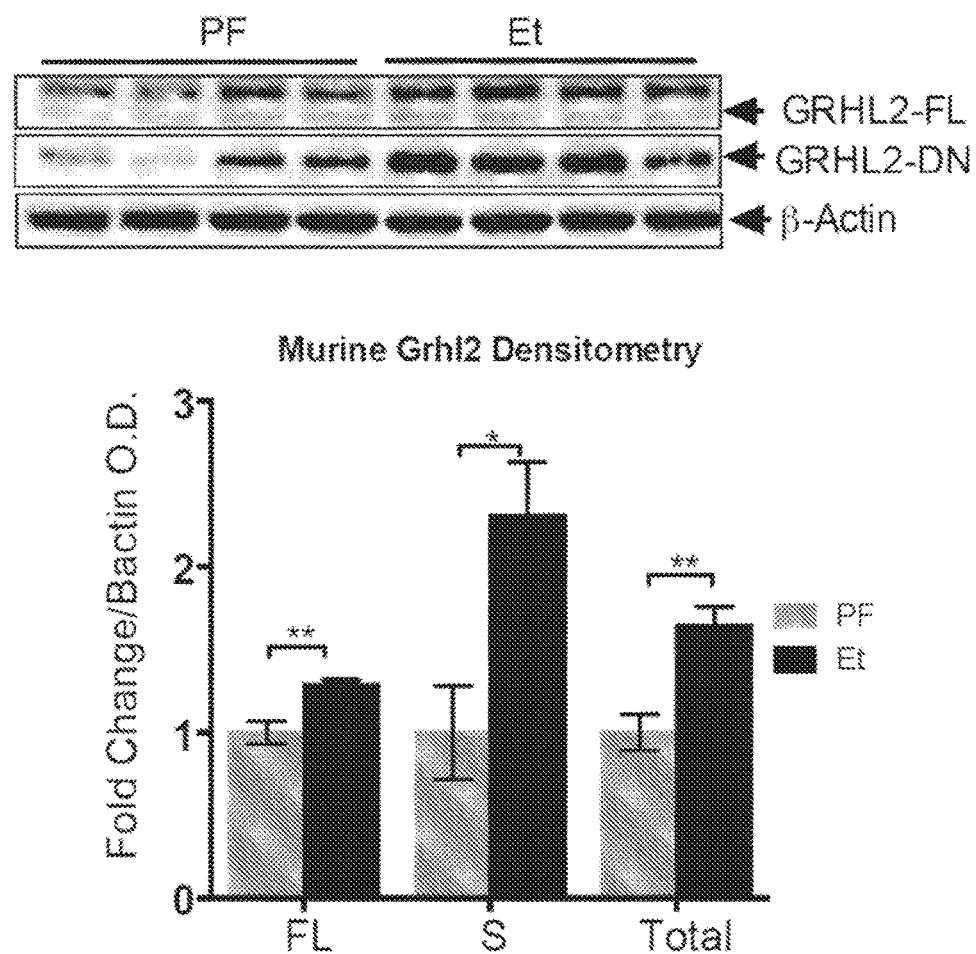
Figure 7E:
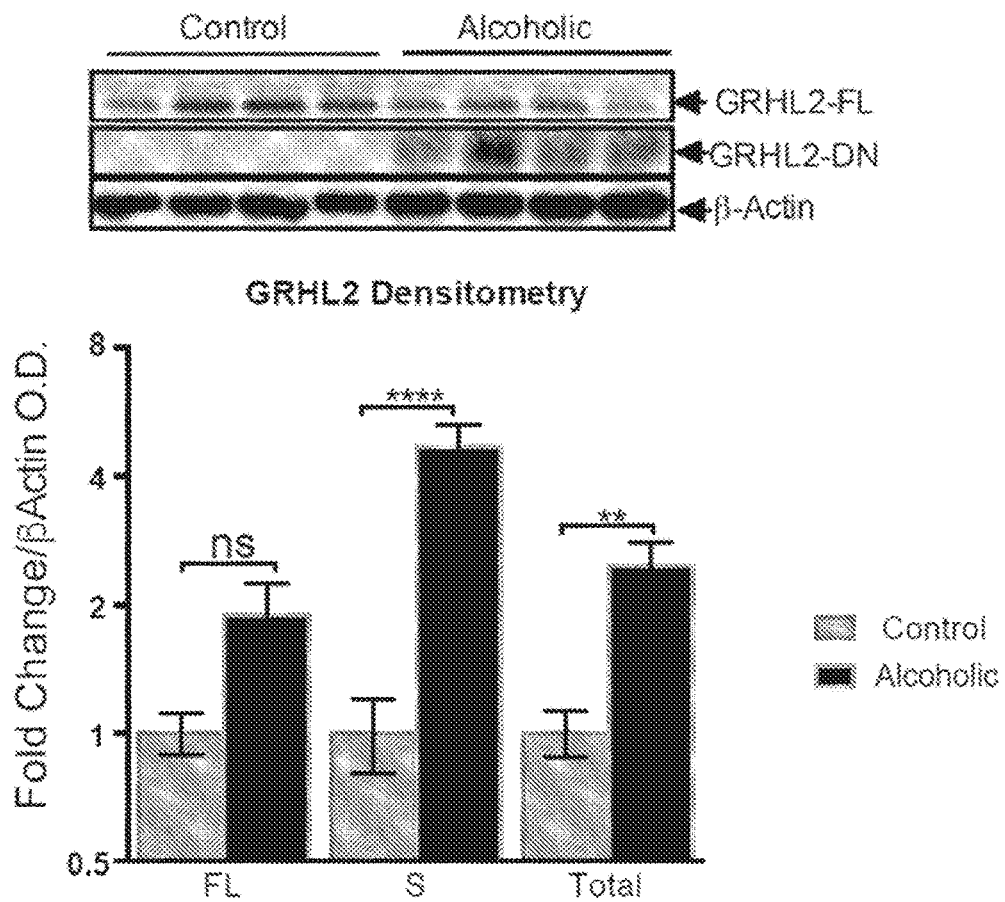
Figure 7F:
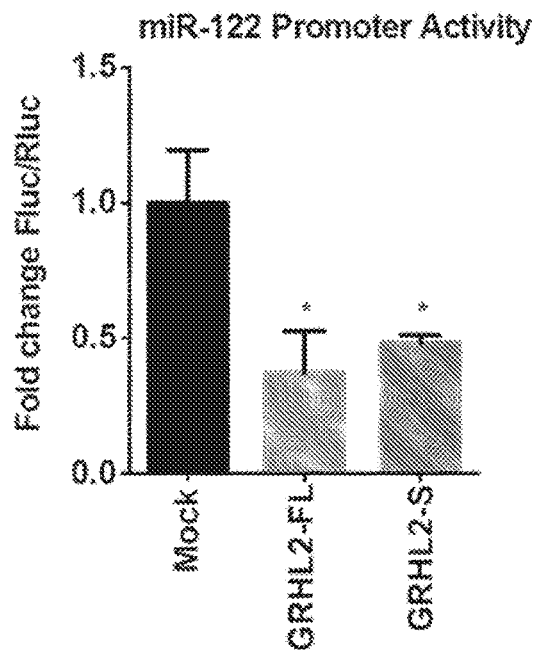
Figure 8:
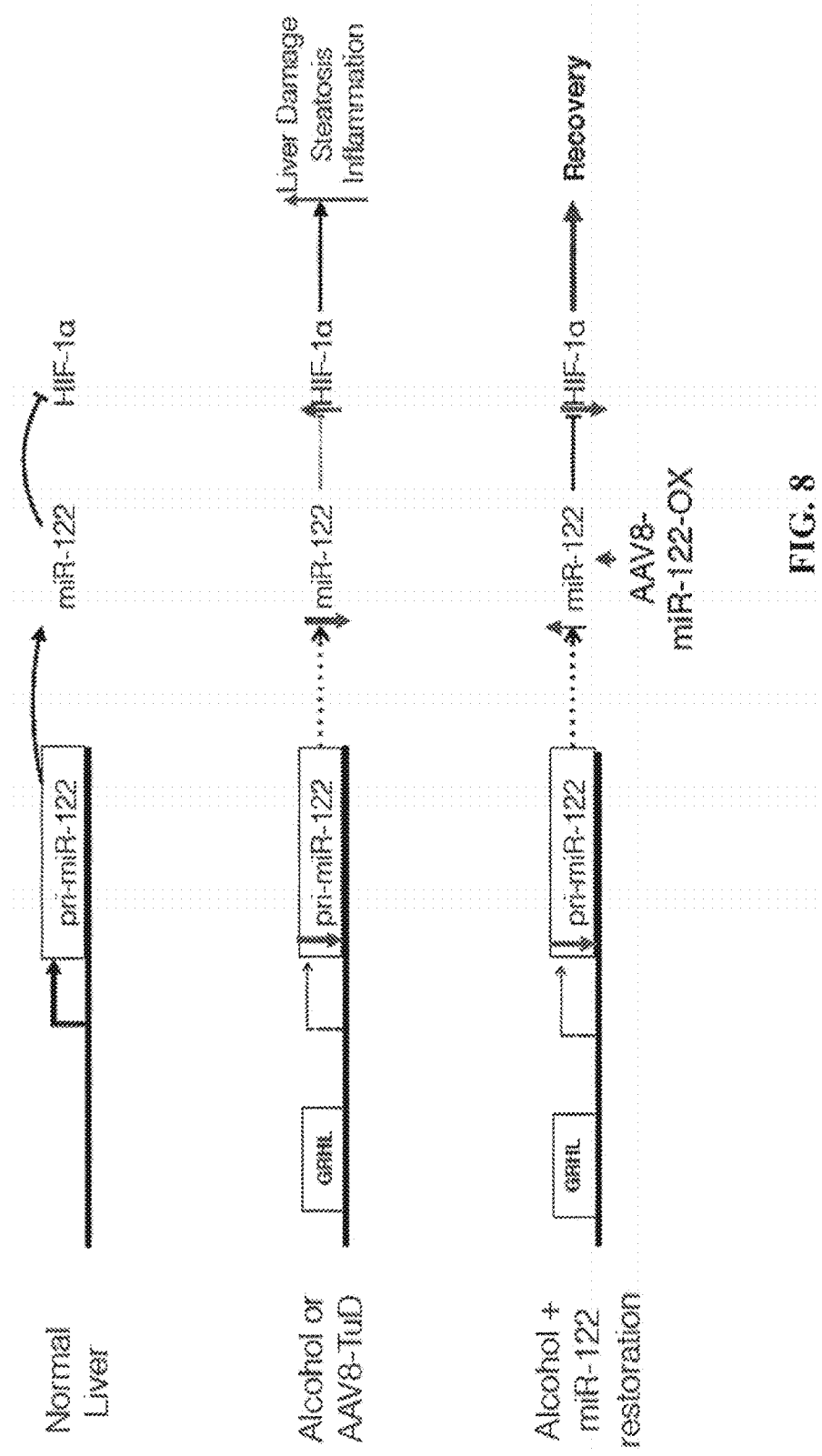
FIG. 8 shows a proposed model. Chronic alcohol increases expression and splicing of GRHL in hepatocytes, inhibiting miR-122 transcription. The decrease in miR-122 increases HIF-1α mRNA driving liver injury, steatosis, inflammation, and fibrosis. Restoration of miR-122 expression leads to decreased HIF-1α expression driving liver recovery.

Immunohistochemistry evaluation revealed that GRLH2 was mostly localized to the biliary epithelium in normal human livers (FIGS. 7A-7C). Increased GRHL2 staining was detected within hepatocytes both in alcohol-fed mice and in livers of alcoholic patients (FIGS. 7A-7C). While, western blot analysis from total livers revealed only a moderate increase in the expression of the 70 kDa GRHL2 (GRHL2-FL) (FIGS. 7D-7E), the levels of the 49 kDa GRHL2 splice variant (GRHL2-S), previously described as a "dominant negative" variant, was significantly increased in both human and murine livers (FIGS. 7D-7E). To dissect the functional relevance of this finding, a luciferase reporter containing the human miR-122 promoter was cotransfected with either the GRHL2-FL or the GRHL2-S isoforms into Huh-7 cells. Results indicate that both the full-length (FL) and spliced variants of GRHL2 potently inhibited miR-122 expression (FIG. 7F). Taken together, data indicate that alcohol regulates miR-122 expression by selectively increasing the spliced form of GRHL2 in hepatocytes (FIG. 8).

Figure 14A:
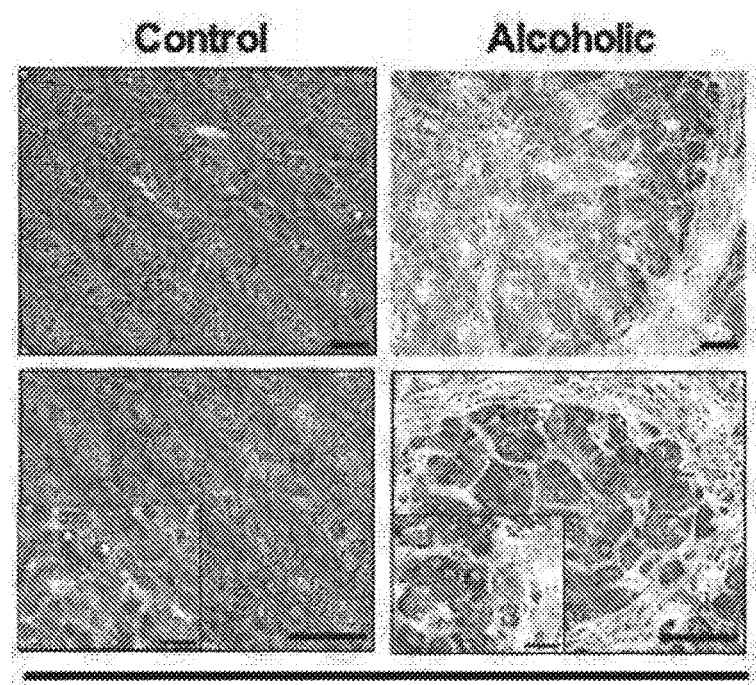
FIGS. 14A-14C show Grainyhead-like 1 and 2 immunohistochemistry. Immunostaining for (FIG. 14A) GRHL1 and (FIG. 14B) GRHL2 in FFPE liver sections from healthy controls and alcoholic cirrhosis patients.
Figure 14B:
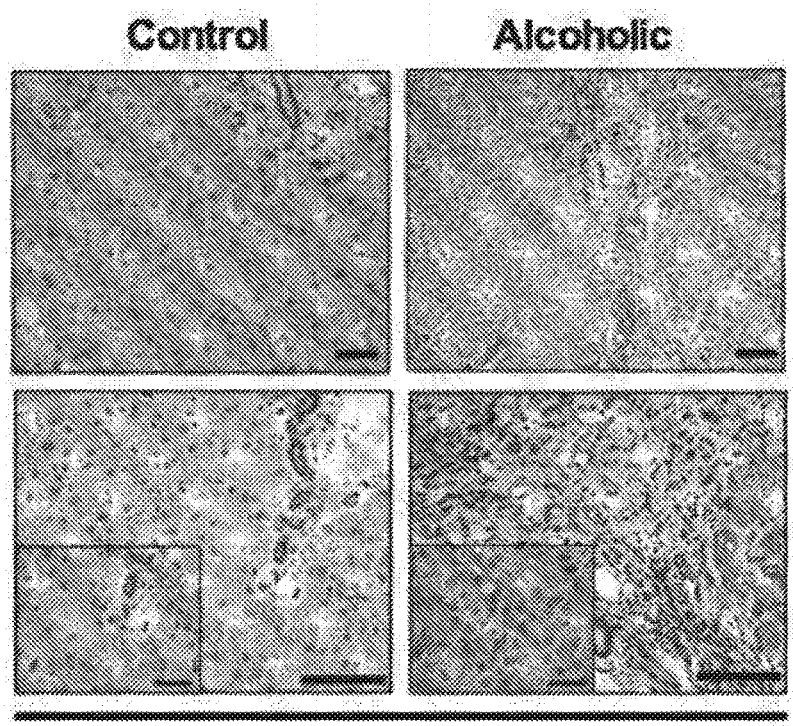
Figure 14C:
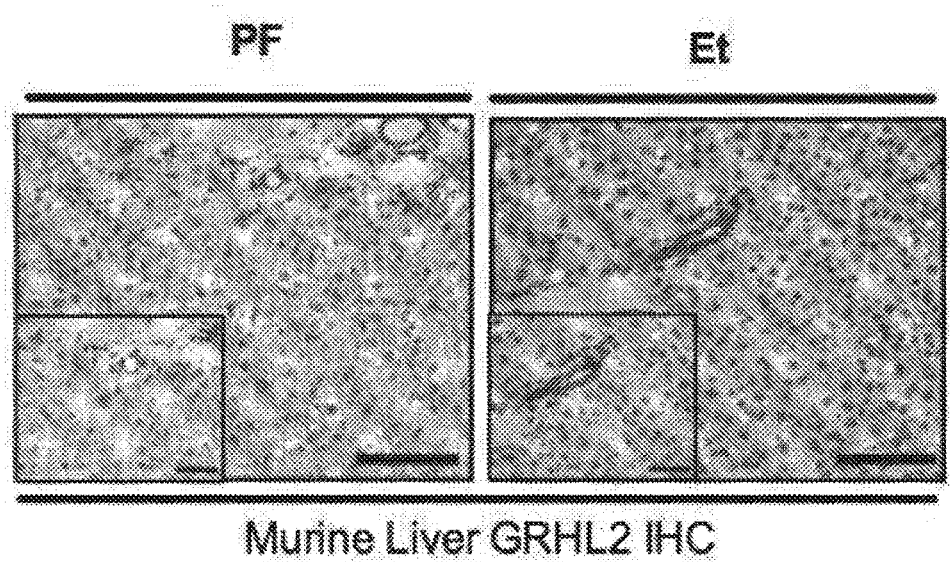

Immunohistochemistry (IHC) revealed that while GRHL1 staining is confined to hepatocytes, no clear change in staining was apparent (FIG. 14A). GRHL2 staining revealed its expression is restricted to the biliary epithelium in healthy controls and pair-fed mice, however, alcoholic cirrhosis patients and alcohol-fed mice had notably increased staining within hepatocytes (FIG. 14B). IHC for GRHL2 of FFPE and immunofluorescence also showed that alcohol-fed mice had increased GRHL2 staining within hepatocytes (FIG. 14C).

Figure 13A:
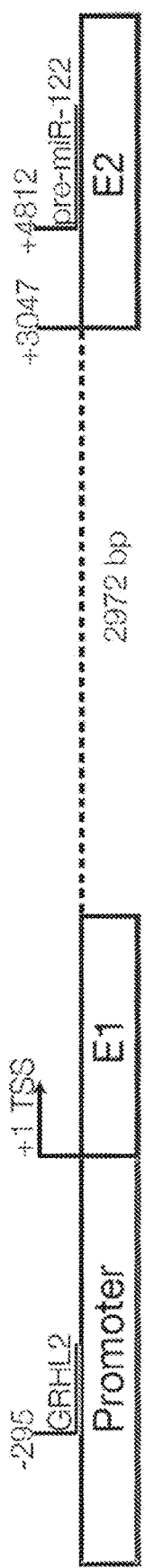
Figure 13B:
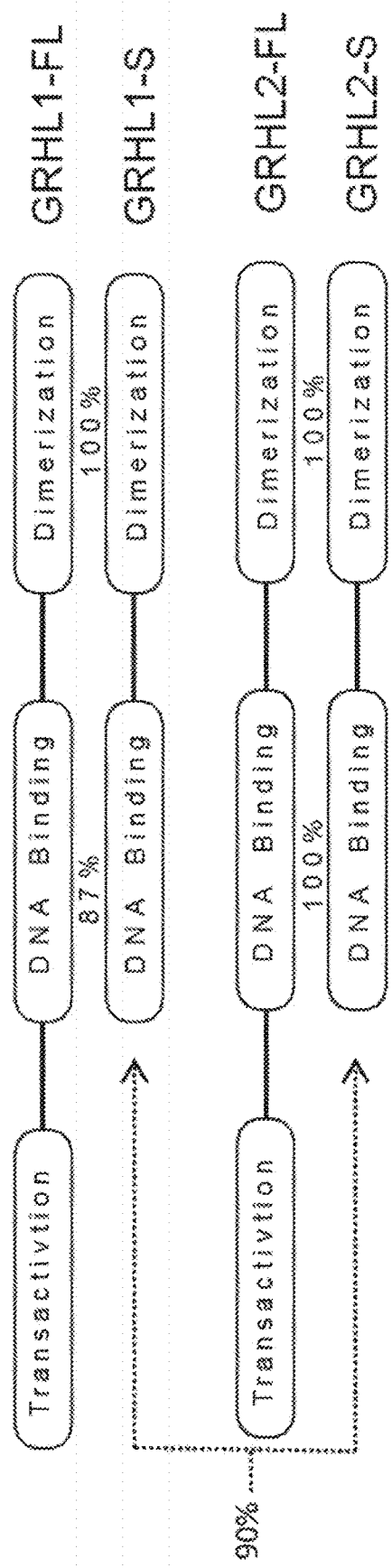
(FIG. 13B) Schematic representation of GRHL1 and GRHL2 full length and spliced protein products, denoting the N-terminal Transactivation domain in the FL variants, the central DNA binding domain, and the C-terminal Dimerization domain. Percentages indicate similarity between indicated domains of the splice variants and full length protein products.
Figure 15A:
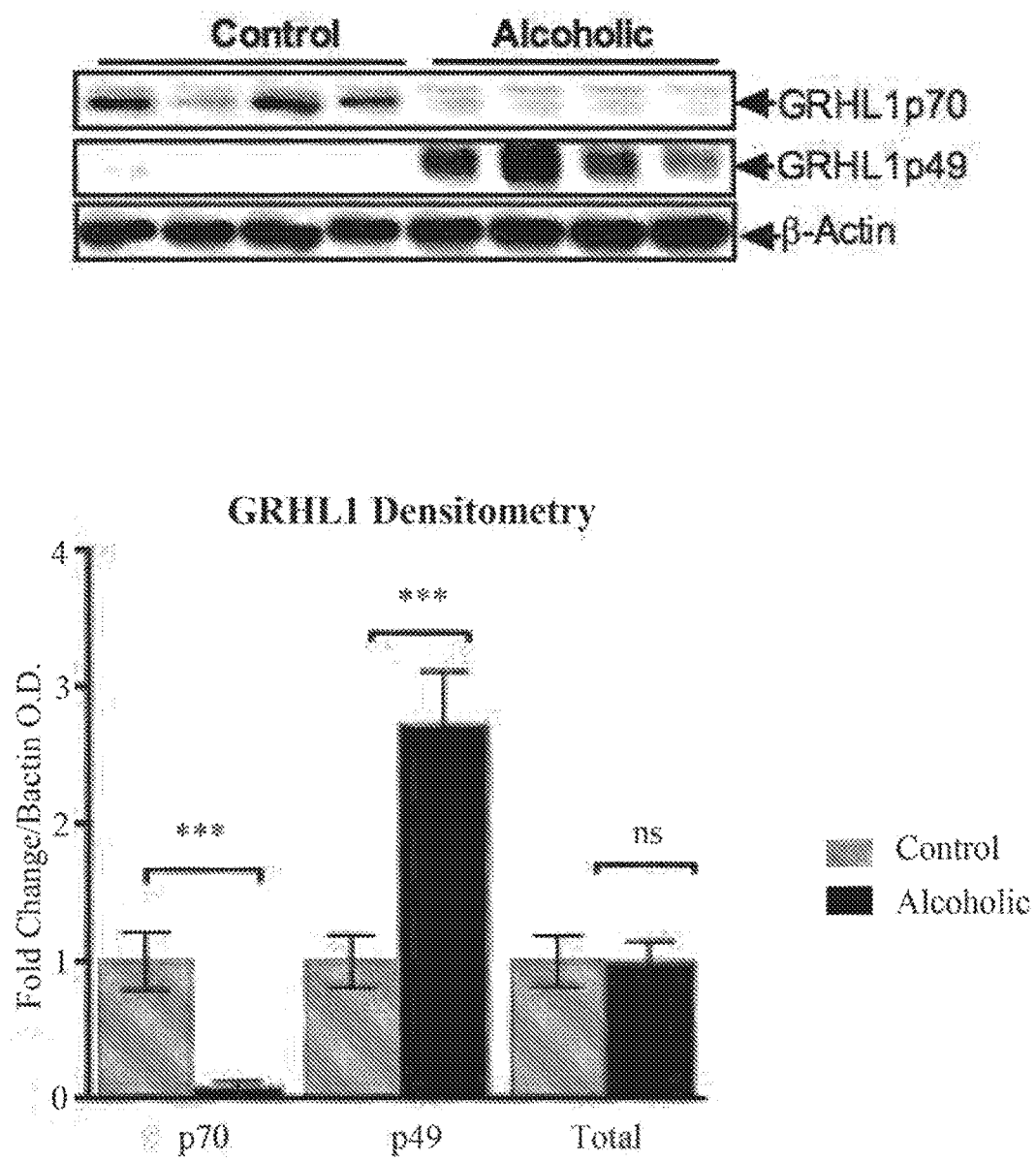
FIGS. 15A-15D show that chronic alcohol induces alternative splicing of GRHL1 and GRHL2. Representative immunoblot for GRHL1 from (FIG. 15A) human (n=5) and (FIG. 15B) murine (n=5) from total liver lysate. Representative immunoblot for GRHL2 from (FIG. 15C) human (n=5) and (FIG. 15D) murine (n=5) from total liver lysate. β-actin was used as a loading control. *P<0.05, P<0.005, *P<0.0005 by Student's t test.
Figure 15B:
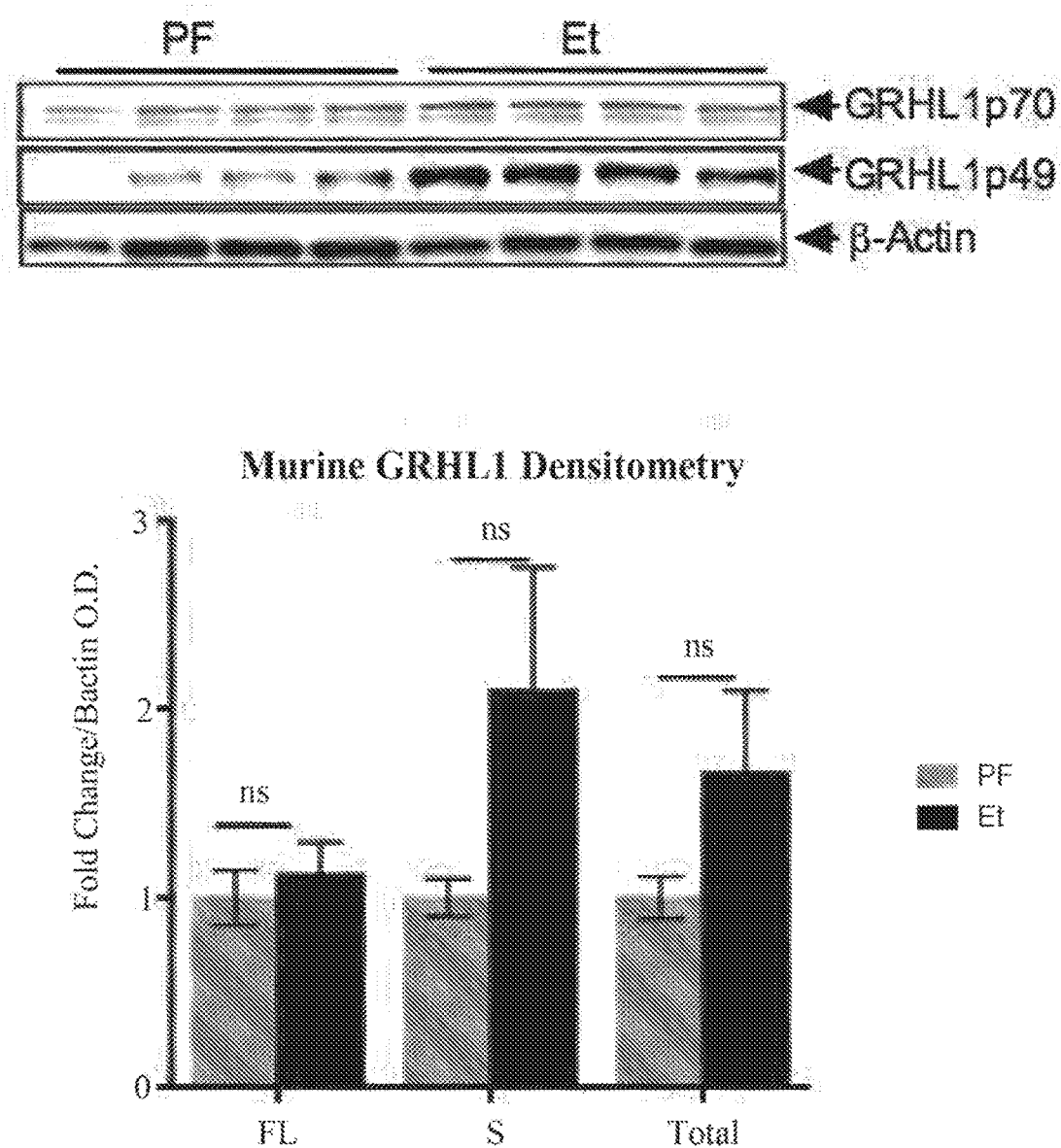
Figure 15C:
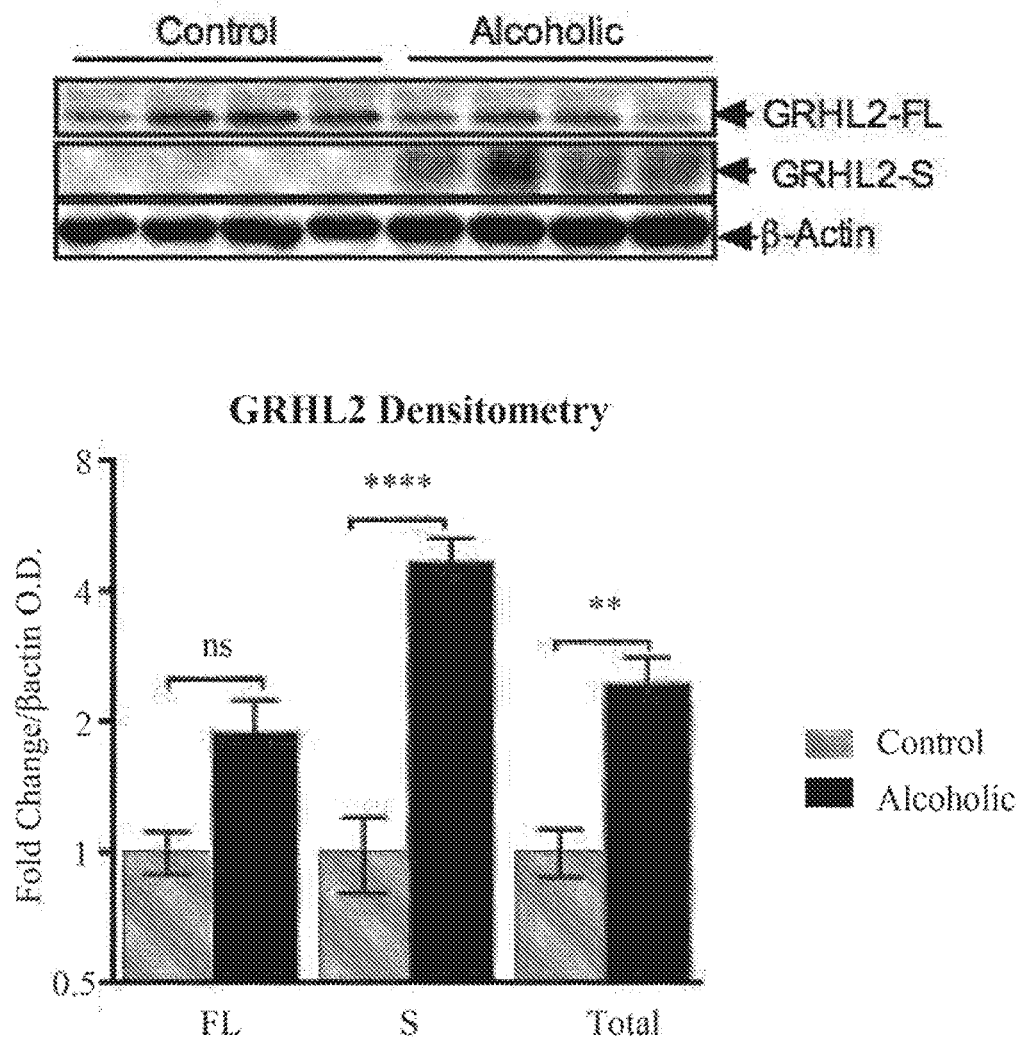
Figure 15D:
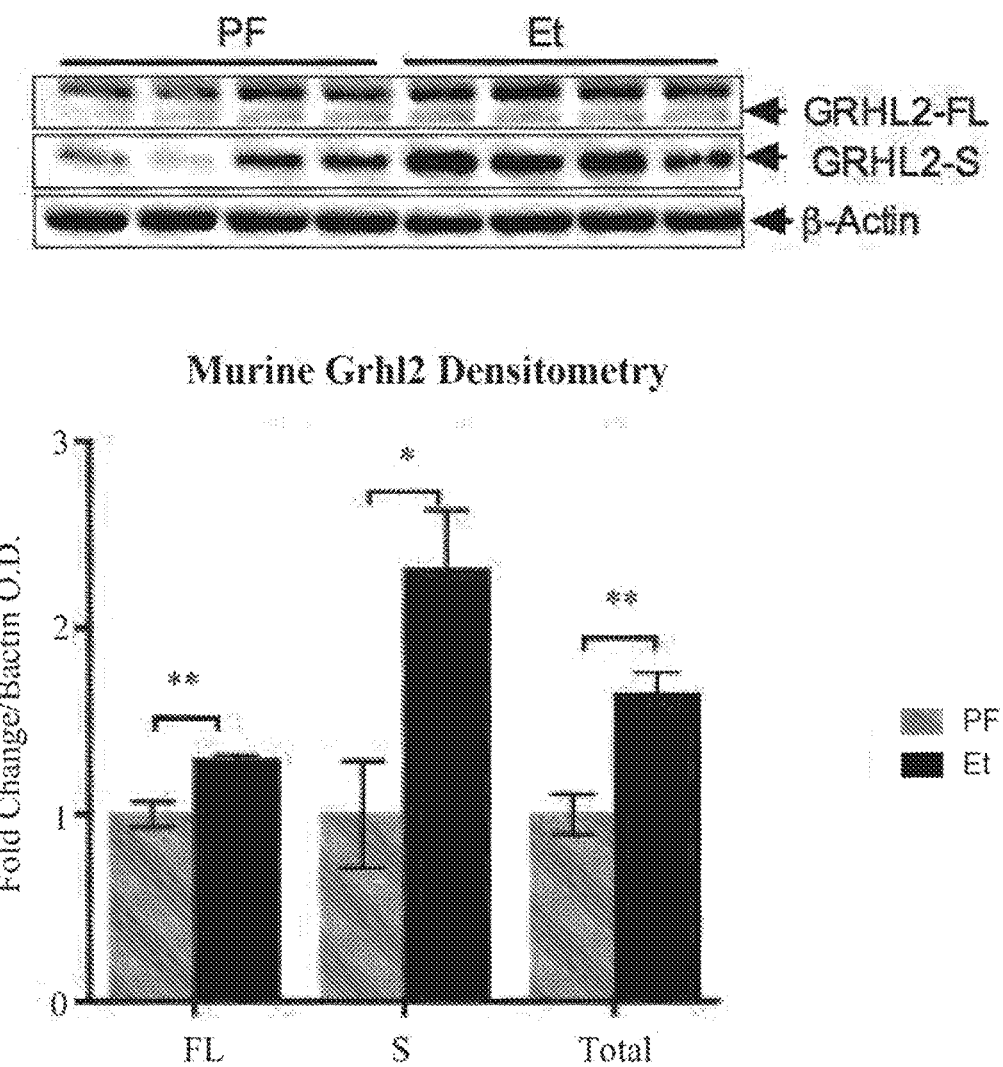

Western blot from total liver lysates revealed that that while GRHL1-FL was decreased in alcoholic patients (FIG. 15A), the expression of the GRHL2-FL was unchanged in either murine or human livers (FIG. 15C). However, expression of the spliced variants of both of GRHL1 and 2, previously described in the literature as dominant-negative isoforms, were significantly increased in both alcohol-fed murine and human alcoholic cirrhosis livers (FIG. 15A-15D). These isoforms, are the result of alternative splicing events in exon 1 characteristic of the Grainyhead-family proteins which result in proteins containing the conserved C-terminal DNA binding and dimerization domains, but lacking N-terminal transactivation domain, thereby inhibiting transcriptional activity at its targeted binding sites (FIG. 13B). Taken together, these results indicate that alcohol increases the spliced or "dominant-negative", variants of GRHL1 and 2 in hepatocytes, allowing them to heterodimerize, and repress miR-122 expression.

To examine the inhibitory effect of the spliced isoforms on miR-122, the promoter region of the human miR-122 gene was cloned into an empty PGL4 luciferase plasmid devoid of an enhancer or promoter. Furthermore, the putative GRHL binding site (FIG. 13A) was mutated, and a truncated promoter which contains the HNF binding sites but is 50 bp downstream of the GRHL site was created. Promoter constructs with either GRHL1-FL, GRHL2-FL, or the GRHL2-S alone and in combination were transfected into HUH-7 cells, which has the highest miR-122 expression of any hepatocyte cell line. Surprisingly, GRHL1, 2, and 2-S alone or in combination all inhibit miR-122 promoter activity equally (FIG. 16A). Furthermore, both the truncated and the reporter with the of mutated putative GRHL binding site not only enhanced baseline promoter activity and only blocked the inhibitory effect of GRHL1-FL, and not of either GRHL2 isoforms (FIG. 16A).

HUH-7 cells, while having high miR-122 expression, their levels are nearly 10-fold lower than primary human hepatocytes. Therefore, to confirm the abovementioned findings, either the GRHL1-FL, 2-FL or 2-S isoforms were transfected independently or in combination into primary human hepatocytes. 48-hours later, total RNA was collected and assayed for pri-miR-122 expression. Oddly, neither GRHL1, GRHL2-FL, or the GRHL2-S inhibited pri-miR-122, while the combination of GRHL1 and GRHL2/GRHL2-S both enhanced expression (FIG. 16B). Taken together these data indicate that alcohol regulates miR-122 expression by selectively increasing the spliced forms of GRHL1 and 2 in hepatocytes.

Materials and Methods

Construction of miR-122 Antagonist and Overexpression Plasmids

The scAAV-anti-miR-122 TuD and scAAV-anti-SCR TuD constructed were made as previously described. The BamHI fragment carrying anti-miR-122 TuD was replaced with the pri-miR-122 sequence amplified from C57/b6 mouse genome DNA to generate scAAV-pri-miR-122 construct (pri-miR-122F, GCGGGATCCGACTGCAGTTTCAGC-GTTTGG (SEQ ID NO: 1) and pri-miR-122R, CGCG-GATCCAAAAAAGACTCTAGGGCCCGACTTTACA (SEQ ID NO: 2)).

Construction of miR-122 Promoter Plasmids

The human mir-122 promoter element were made by insertion of a 1.5 kb amplified sequence from human genomic DNA into a PGL4 plasmid.

ChIP

Recombinant human GRHL2 with a GST was expressed in huh-7 cells. Chomamtin immunoprecipitation was performed according to manufacturer instructions (17-295 Millipore). Briefly, nuclear lysates were sonicated using Biorupter (Diagenode). Sheared chromatin was incubated over night at 4° C. with either Rabbit IgG (sc-2027, Santa Cruz Biotechnology) or Anti-GST (ab19256, Abcam) antibody. The following day, pulldown of the antibody-chromatin complex was performed using Biorad Protein A Surebeads. DNA purification was performed using QIAquick PCR Purification Kit (28104, Quiagen). qPCR was performed using primers specific for the putative GRHL2 human miR-122 promoter locus.

Animal Use

Mice were gradually acclimated to a Lieber-DeCarli liquid diet with 5% ethanol (vol/vol) over a period of 1 week, then maintained on the 5% diet for 4 weeks. Consumption was recorded daily and isocaloric amounts of a control diet (in which dextran-maltose replaced calories from ethanol) were dispensed to pair-fed (PF) animals. Weights were recorded weekly. Wild-type (WT) mice (C57/Bl6), Alb-Cre, and HIF-1flox/flox mice were purchased from Jackson Laboratories (Bar Harbor, Me.). Mice were treated by tail vein injection with AAV vectors at $6 \times 10^{11}$ genome copies/mouse or approximately $3 \times 10^{13}$ genome copies/kg.

Detection of pri-miR-122

Total liver cDNA was generated as stated above. Taqman Primer and probes specific for mmu-pri-miR-122-FAM, hsa-pri-miR-122-FAM were purchased from Applied Biosystems. Human-GAPDH-Hex (applied Biosystems), or mouse-GAPDH-Hex (Bio-Rad), were multiplexed with target genes for normalization.

MiRNA Analysis

Reverse transcription (30 min-16° C.; 30 min-42° C.; 5 min-85° C.) was performed in Eppendorf Mastercycler (Eppendorf, N.Y., USA) using 10 ng RNA, TaqMan primers and miRNA Reverse Transcription Kit (APPLIED BIOSYSTEMS) followed by quantitative RT- in CFX96 (Bio-Rad) using TaqMan Universal Probes Master Mix (Biorad). All tissue results were normalized to snoRNA202, or U6 expression based on Normfinder (moma.dk/normfinder-software) results. miR-122-FAM, U6-FAM, and sno202-FAM primer sets were purchased from Applied Biosystems.

Confocal Microscopy—Immunofluorescence.

Confocal images were processed as previously described. Primary hepatocytes were fixed, permeabilized and stained O/N with either anti-GRHL2 (Atlas antibodies, HPA004820), or normal Rabbit IgG sc-2027 (Santa Cruz Biotechnology). Actin was stained using ActinGreen 488 anti-ReadyProbes Reagent #R37110 (Molecular Probes). Secondary antibody used was anti-rabbit Alexa Fluor 594 #A-21207 (Molecular Probes). Images were acquired using Leica TCS SP5 II Laser Scanning Confocal Microscope.

Statistical Analysis

Statistical significance was determined using two-tailed t-test; ANOVA and Dunnett's multiple comparison post-test were used to compare the means of multiple groups. Outliers were determined using ROUT method and a q of 1%. Data are shown as mean±SEM and were considered statistically significant at $P<0.05$. GraphPad Prism 6.02 (GraphPad Software Inc.) was used for analysis.

Isolation of Primary Mouse Hepatocytes and LMNCs

Anesthetized animals were perfused by way of portal vein with saline solution, followed by enzymatic digestion, as previously described. The hepatocytes were separated by centrifugation, and LMNCs were purified by centrifugation in Percoll gradient followed by CD45+ microbead selection using MACS LS columns (MACS).

In vitro experiments. Primary hepatocytes were cultured in low-glucose DMEM supplemented with 10% fetal bovine serum, 1% Anti-Anti, 1% insulin, transferrin, selenium solution. Primary hepatocytes were seeded in 6-well collagen-coated plates (Biocoat, Becton Dickinson). Before starting stimulation experiments, hepatocytes were rested for 4 hours.

Biochemical Assays and Cytokines

Serum alanine aminotransferase (ALT) levels were determined using a commercially available reagent (Advanced Diagnostics Inc) as described. Liver triglycerides were extracted using a 5% NP-40 lysis solution buffer. Triglycerides were quantified using a commercially available kit (Wako Chemicals) followed normalization to protein amount by BCA protein assay (Pierce).

ELISA

Cytokine levels were monitored in liver whole cell lysates diluted in assay diluent following manufacturer instructions. MCP-1 and TNFα were measured by use of specific anti-mouse ELISA from BioLegend. IL-1β was measured by use of specific anti-mouse ELISA (R&D Systems) that recognizes pro-IL-1β and cleaved IL-1β.

EMSA

The DNA binding activity of HIF-1α was assessed by electrophoretic mobility shift assay as described previously. Briefly, nuclear protein extract from liver (5 µg) was incubated with 50,000 cpm $\gamma^{32}$P-labeled HIF-1α consensus oligonucleotide at room temperature for 30 min. All reactions were run on a 4% polyacrylamide gel, and the dried gel was exposed to an X-ray film at −80° C. for different times. For the cold competition reaction, a 20-fold excess of same, unlabeled, double-stranded oligonucleotide was added to the reaction mixture before adding the labeled oligonucleotide probe.

RNA Extraction and Real-Time PCR

Total RNA was extracted using the Quiagen miRNeasy kit (Quiagen) according to the manufacturer's instructions. Briefly, tissue samples were lysed in QIAzol Lysis reagent (Qiagen), homogenized with stainless steel beads in Tissue-Lyser II (Qiagen) followed by miRNA isolation following manufacturer's instructions and DNase 1 Digest. RNA was quantified using Nanodrop 2000 (Thermo Scientific). Complementary DNA (cDNA) synthesis was performed by reverse transcription of 1 µg total RNA using the iScript Reverse Transcription Supermix (BIO-RAD). Real-time quantitative PCR was performed using Bio-Rad iTaq Universal SYBR Green Supermix and a CFX96 real-time detection system (Bio-Rad Laboratories). Primers were synthesized by IDT, Inc. The primer sequences are listed in Table 2 below. Relative gene expression was calculated by the comparative cycle threshold (Ct) method. The expression level of target genes was normalized to the house-keeping gene, 18S rRNA, in each sample and the fold-change in the target gene expression between experimental groups was expressed as a ratio. Melt-curve analysis was used to confirm the authenticity of the PCR products.

Western Blot Analysis

Whole cell lysates, nuclear and cytoplasmic extracts were prepared from mouse livers as described previously. All westerns were performed under reducing conditions using tris-glycine buffer system and blotted to nitrocellulose membranes. Proteins of interest were detected by immunoblotting with specific primary antibodies against; GRHL2 (Atlas antibodies, HPA004820), beta-actin-HRP (ab9482; Abcam). Respective horseradish peroxidase-labeled secondary antibodies were from Santacruz Biotechonology. The specific immunoreactive bands of interest were detected by chemiluminescence (Biorad) The immunoreactive bands were quantified by densitometric analysis using an UVP System (Bio-Rad Laboratories, Hercules, Calif.).

Histopathological Analysis

Sections of formalin-fixed, paraffin-embedded livers were stained with hematoxylin and eosin (H&E), or Sirius Red and assessed for histological features of steatosis, inflammatory cell invasion, and fibrosis. The H&E and Sirius Red stained sections were independently examined by a 2 pathologists in a blinded manner. Immunohistochemistry staining for GRHL2 (Atlas antibodies, HPA004820) were performed on formalin-fixed, paraffin-embedded livers according to the manufacturer's instructions. ImageJ (NIH) was used for image analysis.

TABLE 1

Demographic and patient data from human samples.

|  | Alcoholic Patients | Hepatitis C Patients |
|---|---|---|
| N | 10 | 12 |
| Age, years | 51 (39-66) | 56 (41-69) |
| Sex, Male/Total | 9/10 | 6/12 |
| Race | White (10/10) | White (9/12), Black (1/12), Hispanic (1/12), American Indian or Alaskan (1/12) |
| MELD | 31 (22-40) | 28 (12-39) |
| Prothrombin Time (INR) | 2.49 (1.50-3.24) | 2.1 (1.23-3.18) |
| Total Bilirubin (mg/dl) | 5.15 (1.50-20.60) | 3.70 (1.50-42.20) |
| Creatinine | 2.13 (1.01-4.04) | 1.29 (0.63-5.34) |
| AST, IU/L | 41.50 (30.00-1425.00) | 80.00 (40.00-286.00) |
| ALP, IU/L | 163.50 (84.00-326.00) | 105.00 (60.00-219.00) |
| Albumin, g/dL | 3.30 (2.70-4.70) | 2.70 (2.00-3.60) |
| Years since abstinence | 0.67 (0.083-2) | 12 (4-20) |
| Months since last drink | 8.00 (1-24) | 0 (0-240) |
| Collection type | Transplant (10/10) | Transplant (10/10) |
| Primary diagnosis | Alcoholic cirrhosis (10/10) | Chronic active hepatitis, type C (10/10) |
| Hepatitis A, IgG+/Total available | 4/10 | 7/10 |
| Hepatitis B core, IgG+/Total available | 0/10 | 4/11 |
| Hepatitis B surface, IgG+/Total available | 2/10 | 4/11 |
| Hepatitis C, IgG+/Total available | 0/10 | 12/12 |
| HIV 1 and 2, IgG+/Total available | 1/10 | 0/10 |
| CMV, IgG+/Total available | 5/10 | 11/12 |
| EBV, IgG+/Total available | 10/10 | 12/12 |
| Pathology report: Evidence of Dysplasia | 0/10 | 0/10 |

TABLE 2

Primers used, all are listed in 5' to 3'.

| Gene | Forward Primer-5'-3' | SEQ ID NO: | Reverse primer-5'-3' | SEQ ID NO: |
|---|---|---|---|---|
| mTNFα | CACCACCATCAAGGACTCAA | 3 | AGGCAACCTGACCACTCTCC | 17 |
| mMCP-1 | CAGGTCCCTGTCATGCTTCT | 4 | CAGGTCCCTGTCATGCTTCT | 18 |
| mActa2 | GTCCCAGACATCAGGGAGTAA | 5 | TCGGATACTTCAGCGTCAGGA | 19 |
| mTGFβ | ATTCCTGGCGTTACCTTG | 6 | CTGTATTCCGTCTCCTTGGTT | 20 |
| mCollagen1a1 | GCTCCTCTTAGGGGCCAT | 7 | CCACGTCTCACCATTGGG | 21 |
| mHIF1α | CAAGATCTCGGCGAAGCAA | 8 | GGTGAGCCTCATAACAGAAGCTTT | 22 |
| mHNF4 | AGCTCGAGGCTCCGTAGTGTTT | 9 | GAAAATGTGCAGGTGTTGACCA | 23 |
| mF4/80 | TGCATCTAGCAATGGACAGC | 10 | GCCTTCTGGATCCATTTGAA | 24 |

TABLE 2-continued

Primers used, all are listed in 5' to 3'.

| Gene | Forward Primer- 5'-3' | SEQ ID NO: | Reverse primer- 5'-3' | SEQ ID NO: |
|---|---|---|---|---|
| mCD68 | CCCACAGGGCAG CACAGTGGAC | 11 | TCCACAGCAGAA GCTTTGGCCC | 25 |
| mIL-1B | CTTTGAAGTTGA CGGACCC | 12 | TGAGTGATACTG CCTGCCTG | 26 |
| mHNF6 | TTCCAGCGCATG TCGGCGCTC | 13 | GGTACTAGTCCG TGGTTCTTC | 27 |
| mPPAR-γ | GGAAGACCACTC GCATTCCTT | 14 | TCGCACTTTGGT ATTCTTGGAG | 28 |
| m/h18s | GTAACCCGTTGA ACCCCATT | 15 | CCATCCAATCGG TAGTAGCG | 29 |
| hGRHL2 | GAAAGTCCAGTT TCACCAGAGG | 16 | GGCACTAAGGCC ACTAGTCTTTT | 30 |

What is claimed is:

1. A method for treating a liver-associated disease, the method comprising: administering to a subject having or suspected of having a liver-associated disease an effective amount of a recombinant adeno-associated virus (rAAV) comprising a transgene encoding miR-122, wherein the transgene encoding miR-122 comprises a sequence represented by SEQ ID NO: 1 or SEQ ID NO: 2, and wherein the liver-associated disease is alcoholic liver disease (ALD), cirrhosis, hepatocellular carcinoma (HCC), or fibrosis of the liver.

2. The method of claim 1, wherein the rAAV comprises a liver-trophic capsid protein.

3. The method of claim 1, wherein the method further comprises inhibiting hypoxia-inducible factor 1α (HIF-1 α) expression in a hepatocyte of the subject.

4. The method of claim 1, wherein the rAAV comprises an AAV2, AAV3, AAV3b, AAV7, AAV8, or AAV9 capsid protein.

5. The method of claim 1, wherein the subject is a mammal.

6. The method of claim 5, wherein the mammal is a human.

7. The method of claim 3, wherein the hepatocyte is a parenchymal hepatocyte, non-parenchymal hepatocyte, sinusoidal endothelial cell, Kupffer cell, hepatic stellate cell, or intrahepatic lymphocyte.

8. The method of claim 1, wherein the transgene encoding miR-122 comprises a sequence represented by SEQ ID NO: 1.

9. The method of claim 1, wherein the transgene encoding miR-122 comprises a sequence represented by SEQ ID NO: 2.

10. The method of claim 1, wherein the transgene encoding miR-122 is flanked by adeno-associated virus (AAV) inverted terminal repeats (ITRs).

* * * * *